(12) United States Patent
Schraga

(10) Patent No.: US 10,463,803 B2
(45) Date of Patent: Nov. 5, 2019

(54) PEN NEEDLE WITH QUICK RELEASE AND/OR REMOVAL SYSTEM

(75) Inventor: Steven Schraga, Surfside, FL (US)

(73) Assignee: STAT MEDICAL DEVICES, INC., North Miami, FL (US)

( * ) Notice: Subject to any disclaimer, the term of this patent is extended or adjusted under 35 U.S.C. 154(b) by 325 days.

(21) Appl. No.: 13/291,584

(22) Filed: Nov. 8, 2011

(65) Prior Publication Data

US 2012/0123334 A1 May 17, 2012

Related U.S. Application Data

(60) Provisional application No. 61/412,986, filed on Nov. 12, 2010.

(51) Int. Cl.
*A61M 5/32* (2006.01)
*A61M 5/50* (2006.01)

(52) U.S. Cl.
CPC ........ *A61M 5/3202* (2013.01); *A61M 5/3213* (2013.01); *A61M 5/50* (2013.01); *A61M 5/5086* (2013.01)

(58) Field of Classification Search
CPC .. A61M 5/347; A61M 5/3293; A61M 5/3202; A61M 5/343; A61M 2005/2488; A61M 5/3213; A61M 5/3216; A61M 5/34; A61M 5/348; A61M 5/346; A61M 5/32; A61M 2005/3206; A61M 2039/1016
USPC ........ 604/111, 239, 240, 110, 187, 241–243, 604/198, 181, 232
See application file for complete search history.

(56) References Cited

U.S. PATENT DOCUMENTS

| 4,490,142 | A | * | 12/1984 | Silvern | .................... 604/241 |
| 4,568,336 | A | * | 2/1986 | Cooper | .................. A61M 5/00 604/201 |
| 4,894,055 | A | | 1/1990 | Sudnak | |
| 4,909,792 | A | | 3/1990 | Norelli | |

(Continued)

FOREIGN PATENT DOCUMENTS

| WO | 99/08742 | 2/1999 |
| WO | 00/69501 | 11/2000 |
| WO | WO 2008/077706 | 7/2008 |

OTHER PUBLICATIONS

"Usage Instructions for NovoLog Mix", FlexPen 70/30, , pp. 2.

*Primary Examiner* — Nathan R Price
*Assistant Examiner* — Weng Lee
(74) *Attorney, Agent, or Firm* — Thomas Horstemeyer, LLP

(57) ABSTRACT

An injection device tip includes a body configured to be removably connected to an injection device. A needle has a first portion projecting out from the body and a second portion projecting into a space within the body. The body includes at least one of; at least one slot separating flexible portions which can be deflected outwardly to cause release of an engagement between the body and a proximal end of the injection device, at least one slot separating flexible portions which can be deflected outwardly to cause release of a thread engagement, at least one frangible connection arranged on the body, at least one indicator arrangement on the body which provides a visual indication that the pen needle has been previously used, and at least one spacing separating two generally semi-circular or generally semi-cylindrical flexible portions which can be deflected outwardly.

19 Claims, 48 Drawing Sheets

(56) References Cited

U.S. PATENT DOCUMENTS

| | | | | |
|---|---|---|---|---|
| 4,927,019 A | * | 5/1990 | Haber | A61M 5/002 206/365 |
| 4,973,318 A | | 11/1990 | Holm et al. | |
| 5,205,833 A | * | 4/1993 | Harsh et al. | 604/240 |
| 5,226,894 A | * | 7/1993 | Haber | A61M 5/24 604/198 |
| 5,242,401 A | | 9/1993 | Colsky | |
| 5,242,416 A | | 9/1993 | Hutson | |
| 5,383,857 A | * | 1/1995 | Levitov | A61M 5/3271 604/110 |
| 5,389,085 A | | 2/1995 | D'Alessio et al. | |
| 5,419,773 A | | 5/1995 | Rupp | |
| 5,454,828 A | | 10/1995 | Schraga | |
| 5,591,138 A | | 1/1997 | Vaillancourt | |
| 5,593,387 A | | 1/1997 | Rupp | |
| 5,611,786 A | * | 3/1997 | Kirchhofer | A61M 5/348 604/232 |
| 5,624,405 A | * | 4/1997 | Futagawa | A61M 5/28 604/187 |
| 5,968,021 A | * | 10/1999 | Ejlersen | A61M 5/3213 206/365 |
| 5,980,488 A | | 11/1999 | Thorne | |
| 6,117,108 A | | 9/2000 | Woehr et al. | |
| 6,149,630 A | * | 11/2000 | Robinson | A61M 5/3243 604/110 |
| D445,602 S | | 7/2001 | Woehr et al. | |
| 6,287,278 B1 | | 9/2001 | Woehr et al. | |
| 6,379,333 B1 | | 4/2002 | Brimhall et al. | |
| 6,391,003 B1 | | 5/2002 | Lesch, Jr. | |
| 6,460,234 B1 | | 10/2002 | Gianchandani | |
| 6,470,754 B1 | | 10/2002 | Gianchandani | |
| 6,616,630 B1 | | 9/2003 | Woehr et al. | |
| 6,652,490 B2 | | 11/2003 | Howell | |
| 6,749,588 B1 | | 6/2004 | Howell et al. | |
| 6,855,129 B2 | | 2/2005 | Jensen et al. | |
| 7,125,397 B2 | | 10/2006 | Woehr et al. | |
| 7,214,211 B2 | | 5/2007 | Woehr et al. | |
| 7,264,613 B2 | | 9/2007 | Woehr et al. | |
| 7,462,168 B2 | * | 12/2008 | Stonehouse | A61M 5/326 604/192 |
| 7,540,858 B2 | | 6/2009 | DiBiasi | |
| 7,553,293 B2 | | 6/2009 | Jensen et al. | |
| 7,871,397 B2 | | 1/2011 | Schraga | |
| 7,988,678 B2 | * | 8/2011 | Monson et al. | 604/240 |
| 8,235,950 B2 | * | 8/2012 | Emmott et al. | 604/192 |
| 9,039,047 B2 | * | 5/2015 | Imai | A61J 1/2089 285/402 |
| 2002/0004648 A1 | | 1/2002 | Larsen et al. | |
| 2002/0133122 A1 | | 9/2002 | Giambattista et al. | |
| 2003/0014018 A1 | | 1/2003 | Giambattista et al. | |
| 2003/0105431 A1 | | 6/2003 | Howell | |
| 2003/0195471 A1 | | 6/2003 | Howell | |
| 2004/0116856 A1 | | 6/2004 | Woehr et al. | |
| 2004/0186434 A1 | | 9/2004 | Harding et al. | |
| 2004/0204681 A1 | | 10/2004 | Thoresen et al. | |
| 2004/0220532 A1 | * | 11/2004 | Caizza | A61M 5/3216 604/264 |
| 2004/0236284 A1 | | 11/2004 | Hoste et al. | |
| 2004/0236288 A1 | | 11/2004 | Howell | |
| 2005/0004532 A1 | | 1/2005 | Woehr et al. | |
| 2005/0038392 A1 | | 2/2005 | DeSalvo | |
| 2005/0080378 A1 | | 4/2005 | Cindrich et al. | |
| 2005/0107748 A1 | | 5/2005 | Thorne et al. | |
| 2005/0277881 A1 | | 12/2005 | Sibbitt | |
| 2005/0277895 A1 | * | 12/2005 | Giambattista et al. | 604/198 |
| 2005/0283115 A1 | | 12/2005 | Giambattista et al. | |
| 2006/0229652 A1 | | 10/2006 | Iio et al. | |
| 2006/0264828 A1 | | 11/2006 | Woehr et al. | |
| 2007/0049868 A1 | | 3/2007 | Woehr et al. | |
| 2007/0083159 A1 | | 4/2007 | Woehr et al. | |
| 2007/0088283 A1 | * | 4/2007 | Hongo | A61M 5/344 604/187 |
| 2007/0100297 A1 | | 5/2007 | Woehr et al. | |
| 2007/0129689 A1 | | 6/2007 | Woehr et al. | |
| 2007/0203458 A1 | | 8/2007 | Tsubota | |
| 2007/0255225 A1 | * | 11/2007 | Alchas | A61M 5/3202 604/192 |
| 2008/0108951 A1 | | 5/2008 | Jerde et al. | |
| 2008/0154192 A1 | | 6/2008 | Schraga | |
| 2008/0177237 A1 | * | 7/2008 | Stonehouse | A61M 5/326 604/263 |
| 2008/0177238 A1 | | 7/2008 | Follman et al. | |
| 2009/0069753 A1 | | 3/2009 | Ruan et al. | |
| 2010/0114035 A1 | * | 5/2010 | Schubert | A61B 5/1444 604/198 |
| 2010/0211014 A1 | * | 8/2010 | Klint et al. | 604/173 |
| 2010/0292654 A1 | | 11/2010 | Schraga | |
| 2011/0022001 A1 | | 1/2011 | Wei | |
| 2011/0077615 A1 | | 3/2011 | Schraga | |
| 2011/0106016 A1 | | 5/2011 | Wei | |
| 2011/0118667 A1 | | 5/2011 | Zaiken et al. | |
| 2011/0160675 A1 | | 6/2011 | Ruan et al. | |
| 2013/0211345 A1 | * | 8/2013 | Jugl | A61M 5/2466 604/240 |

\* cited by examiner

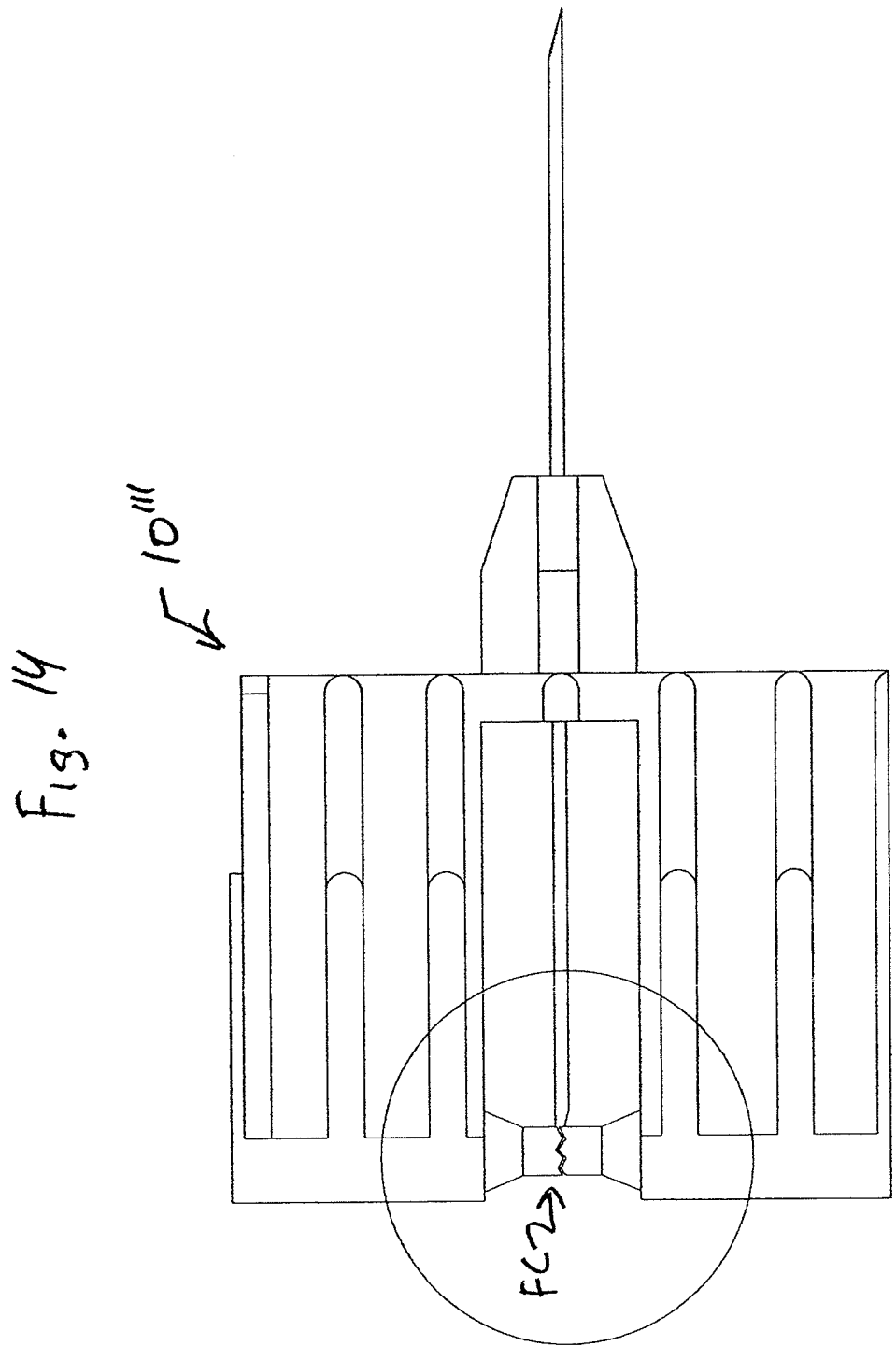

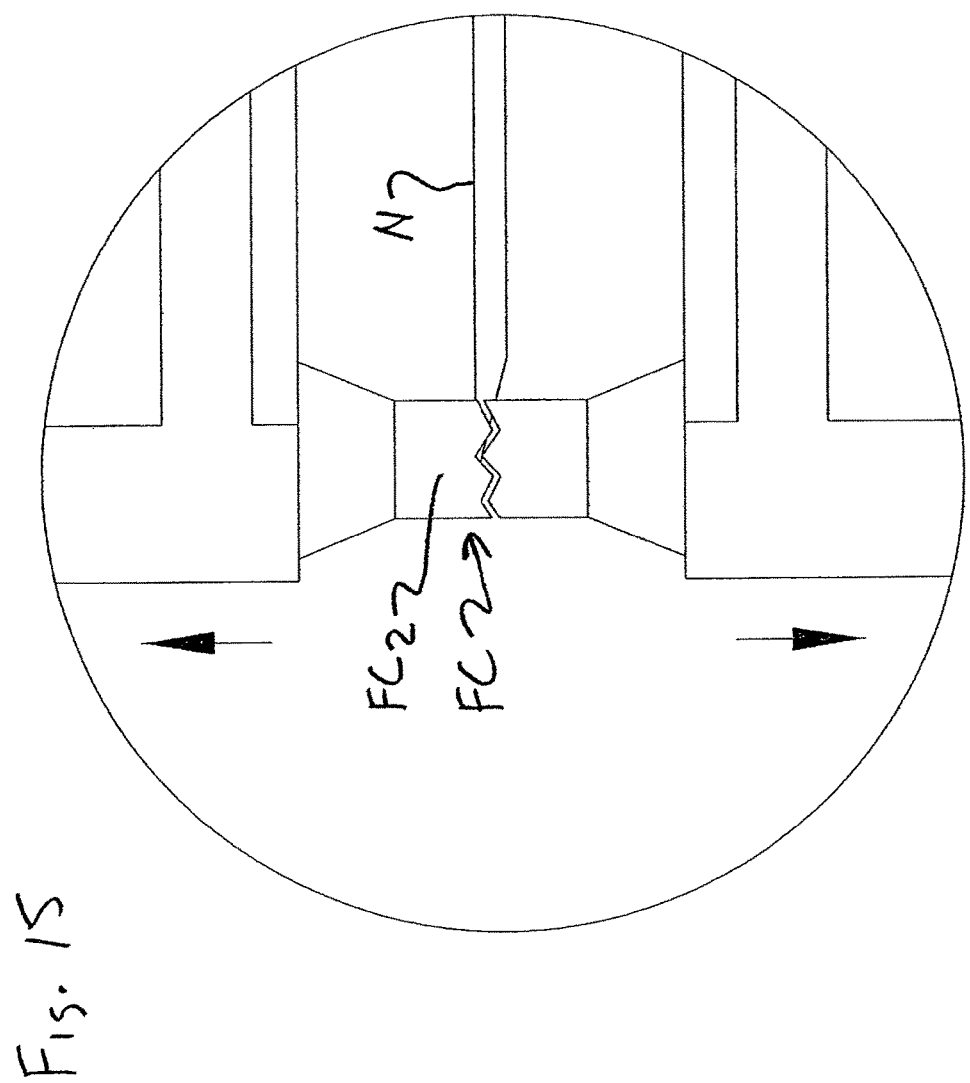

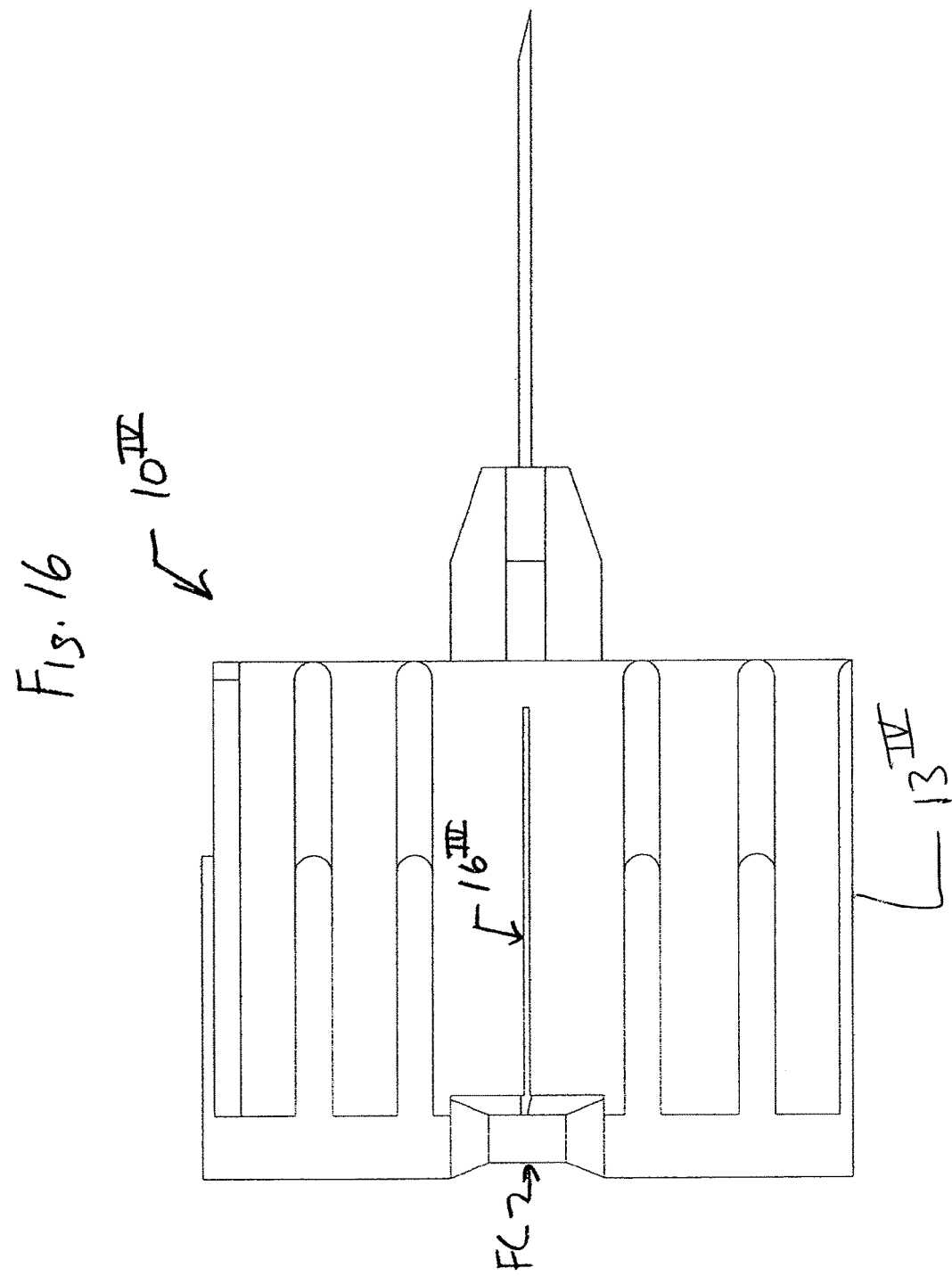

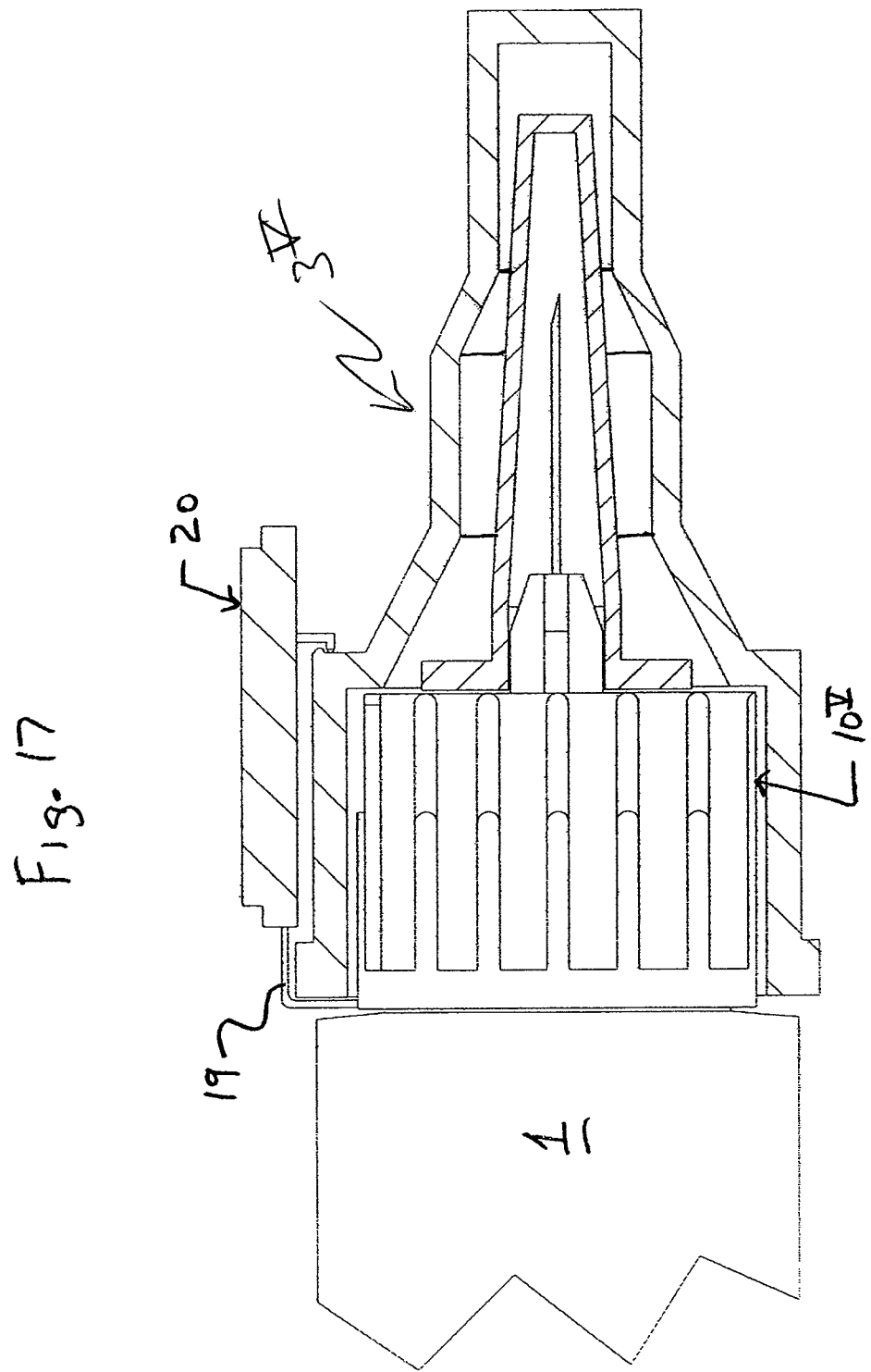

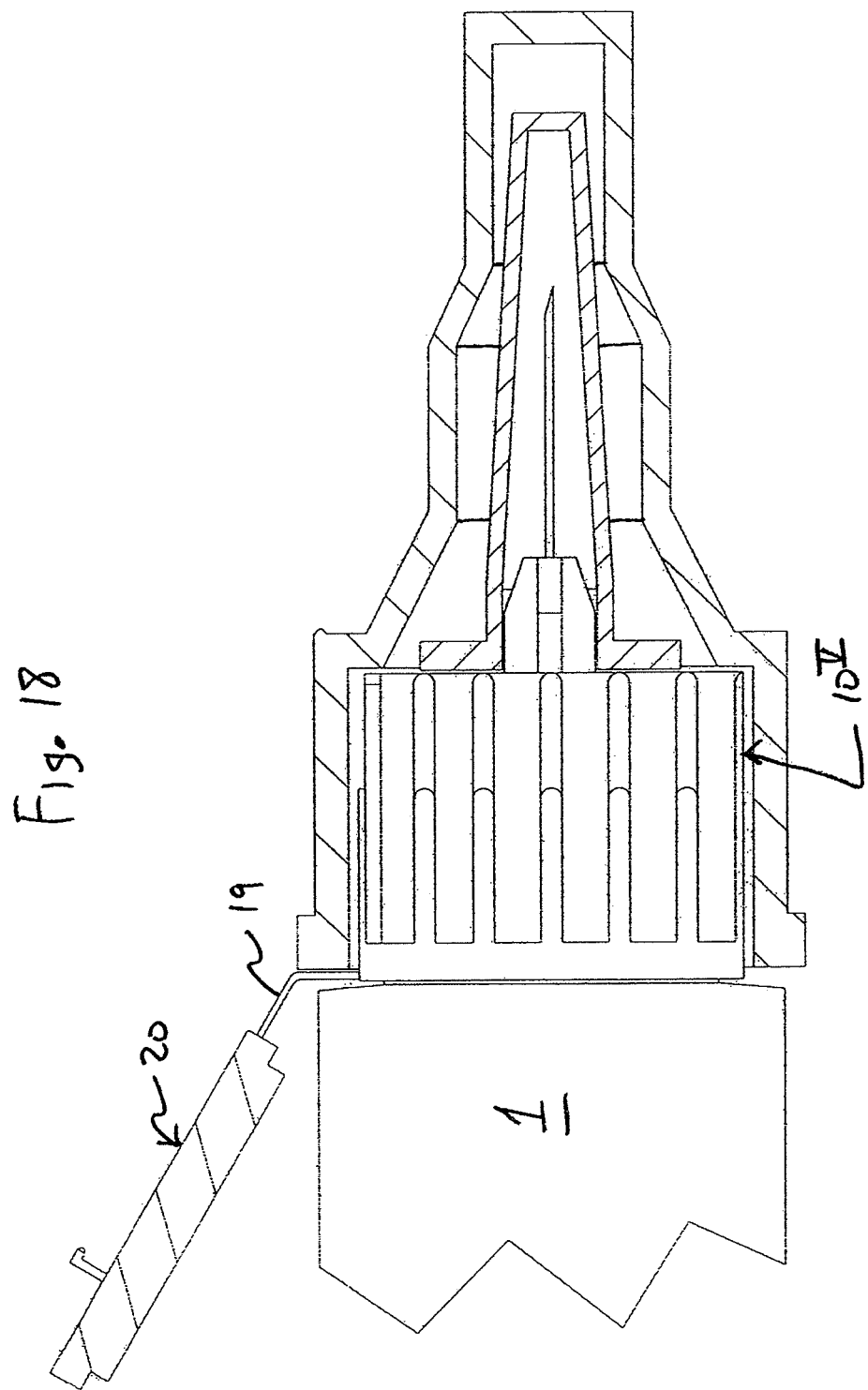

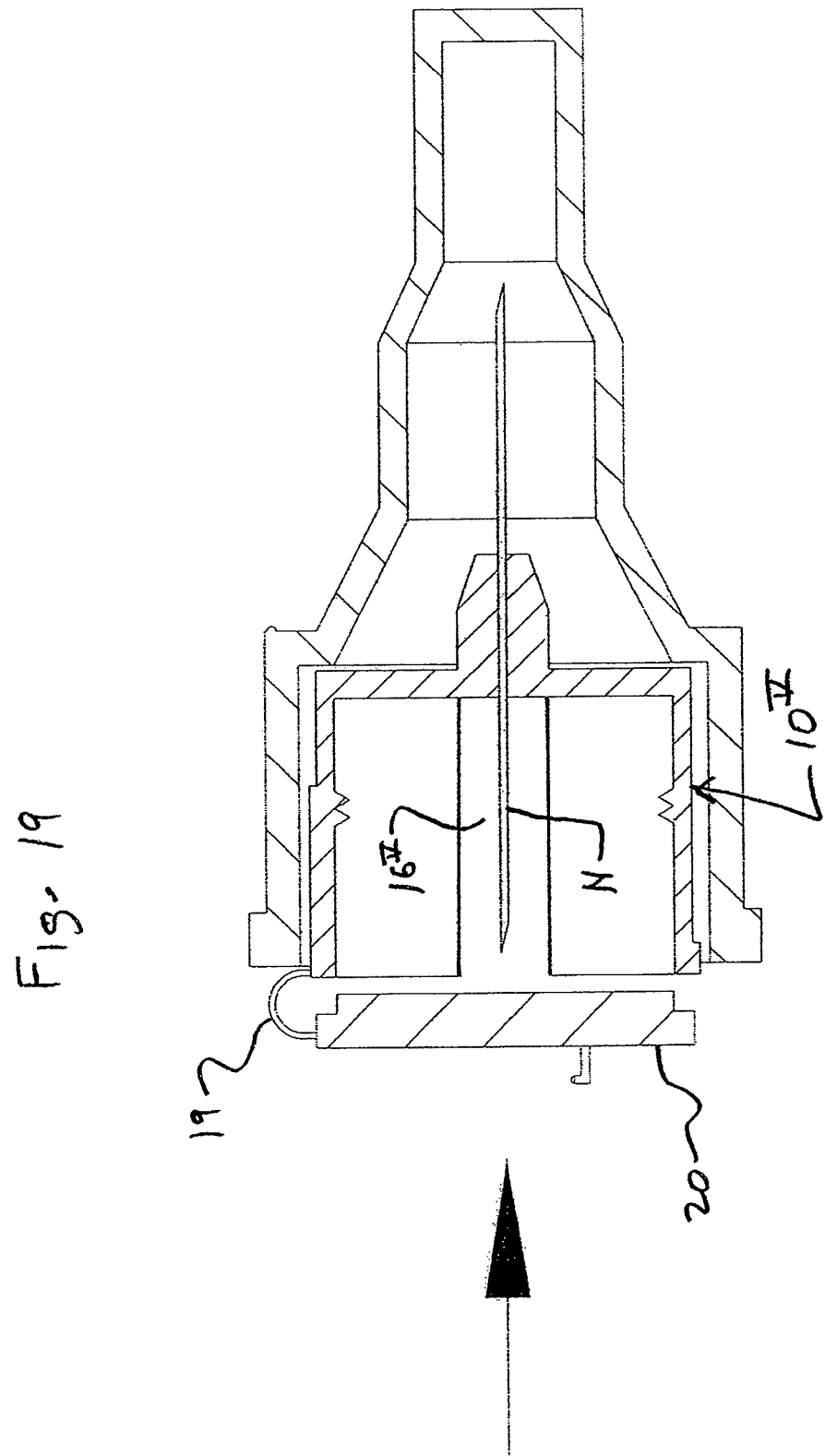

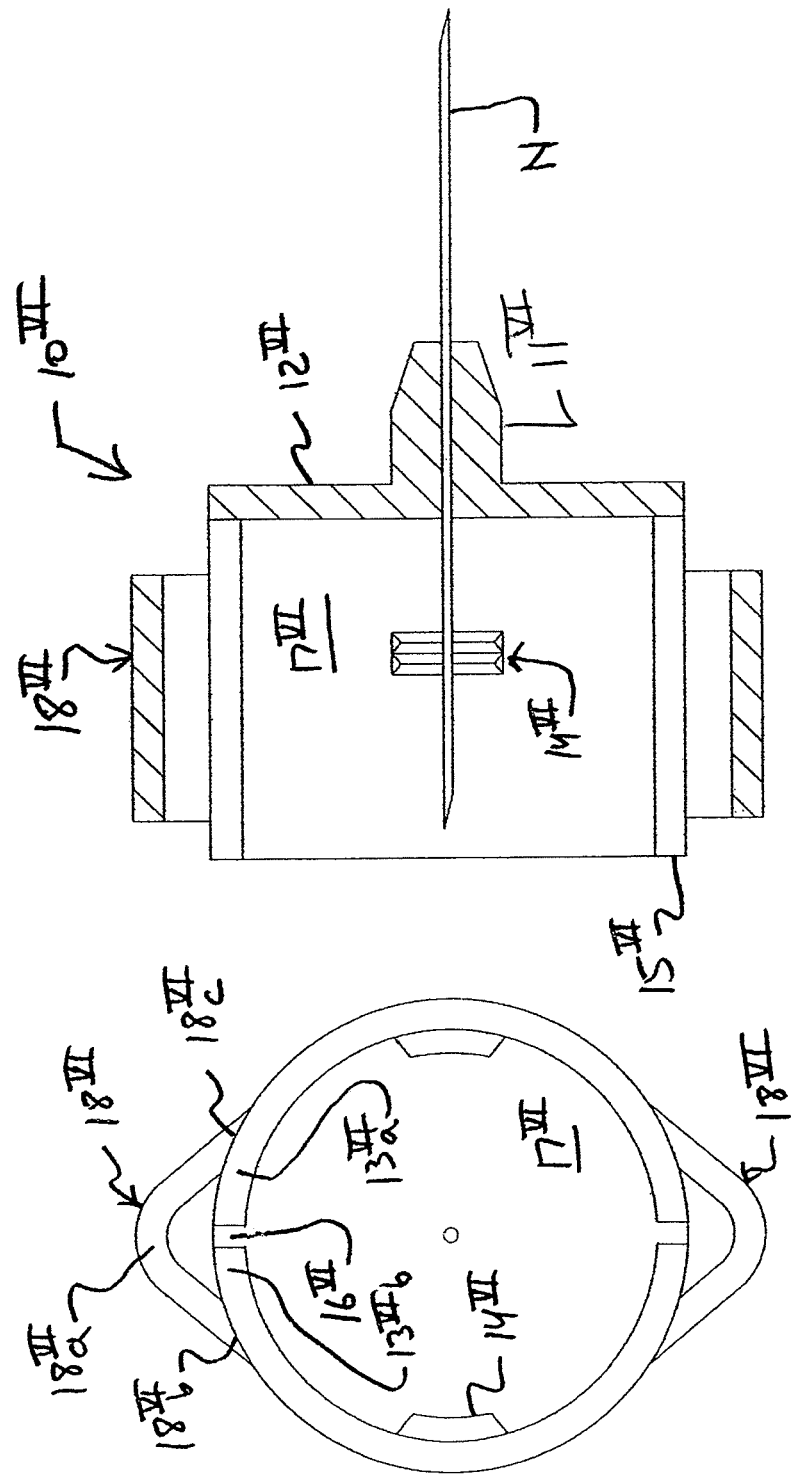

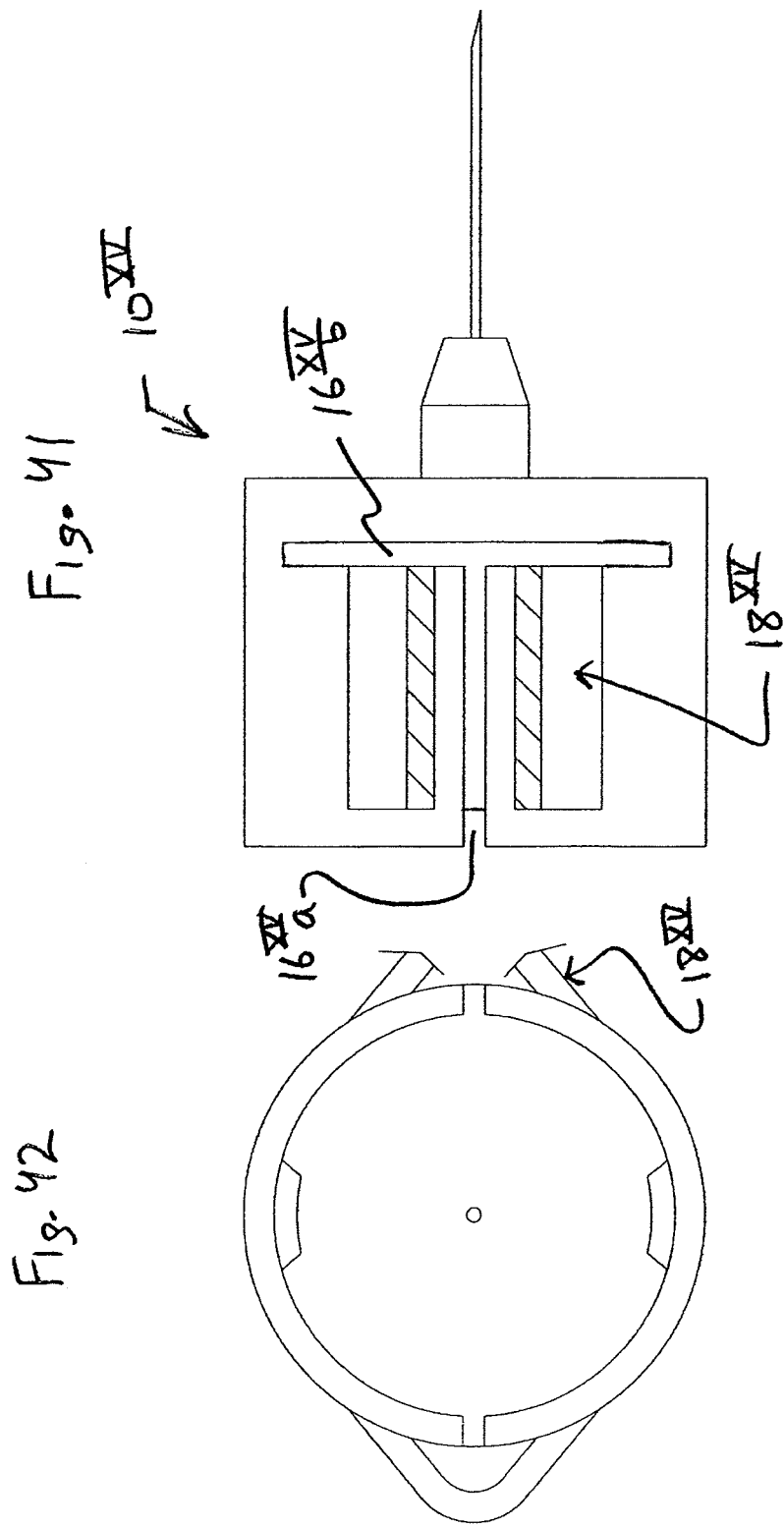

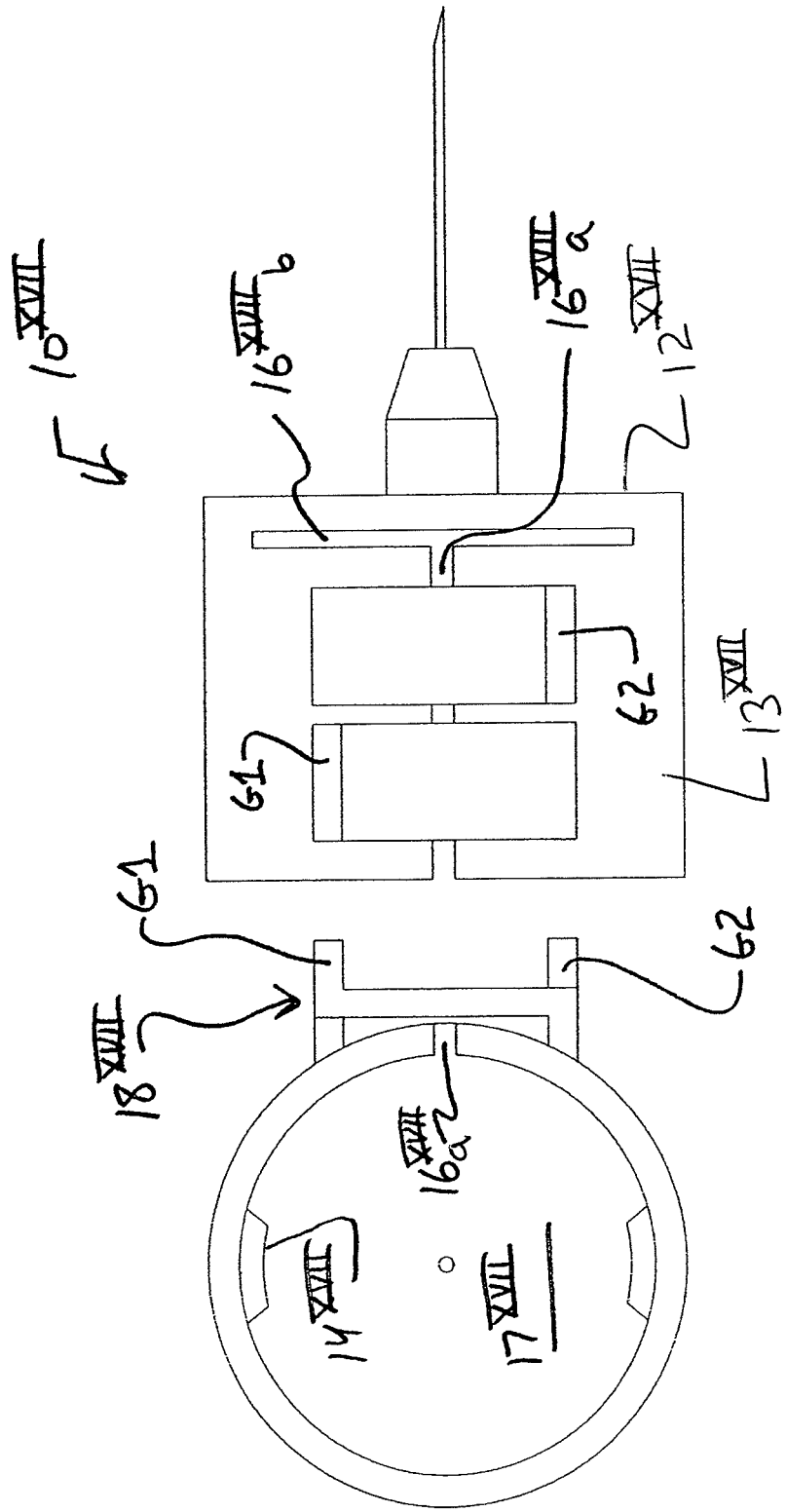

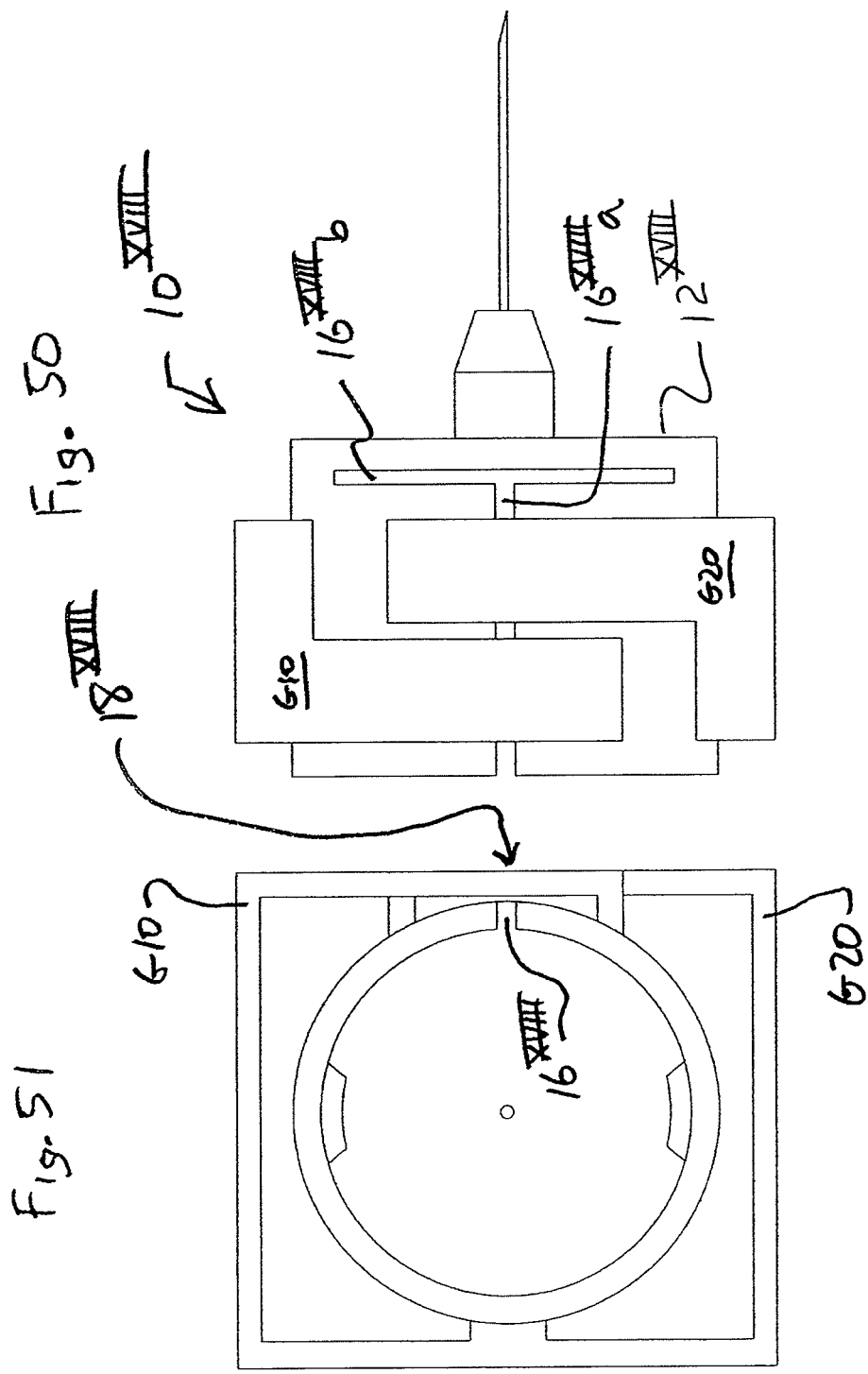

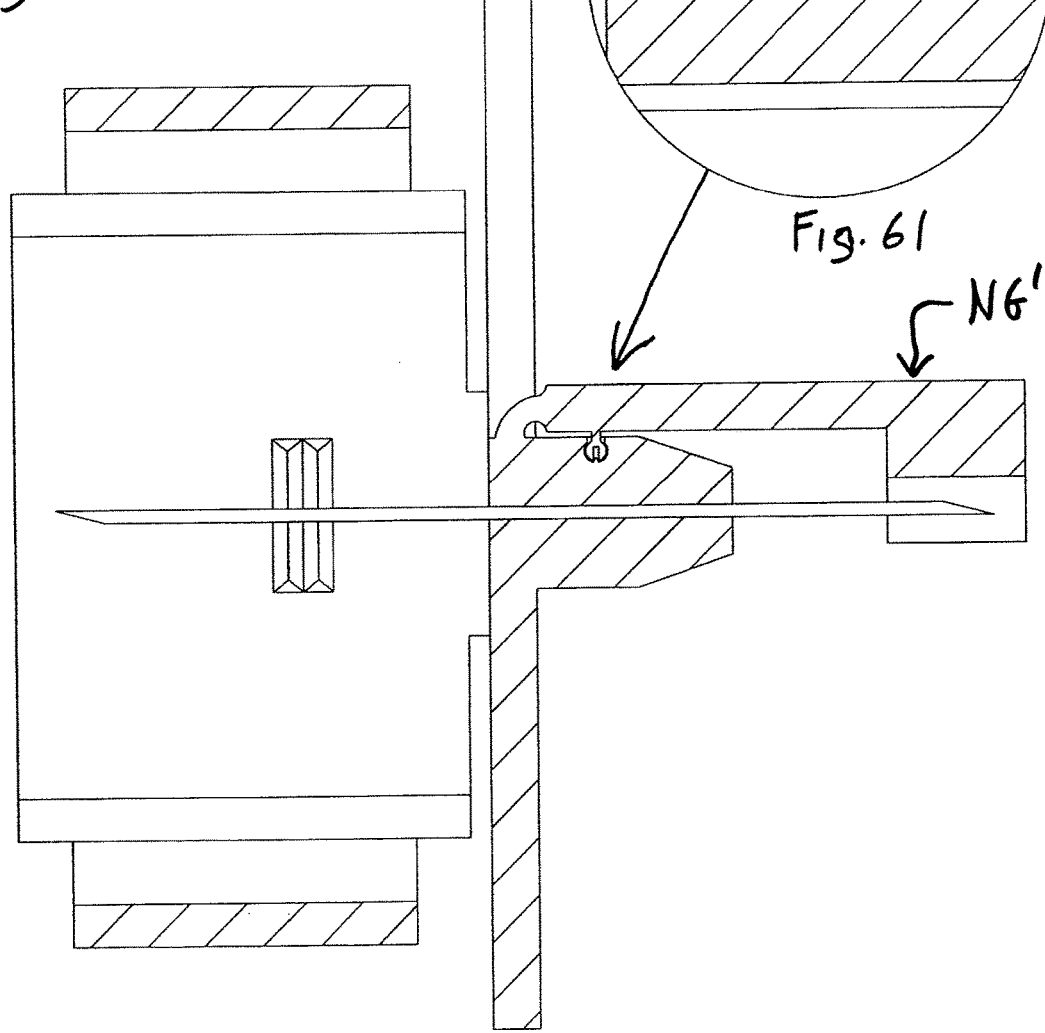

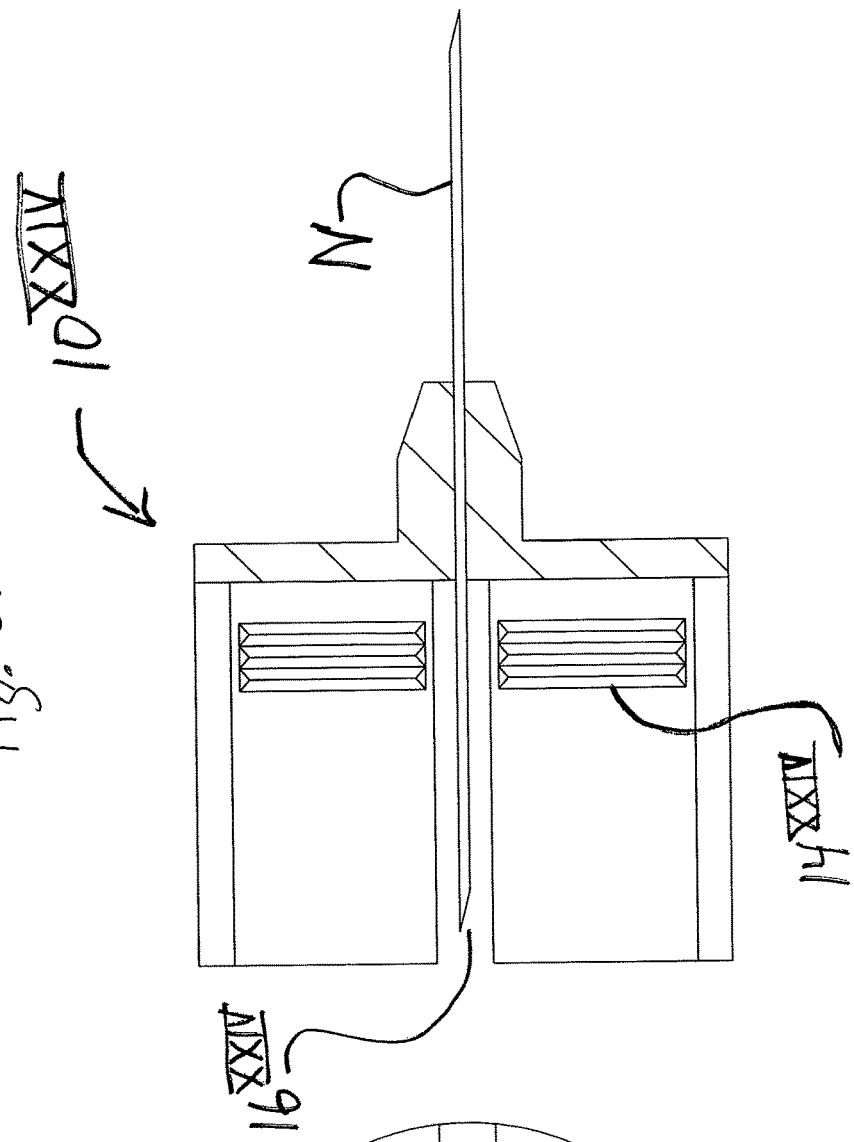

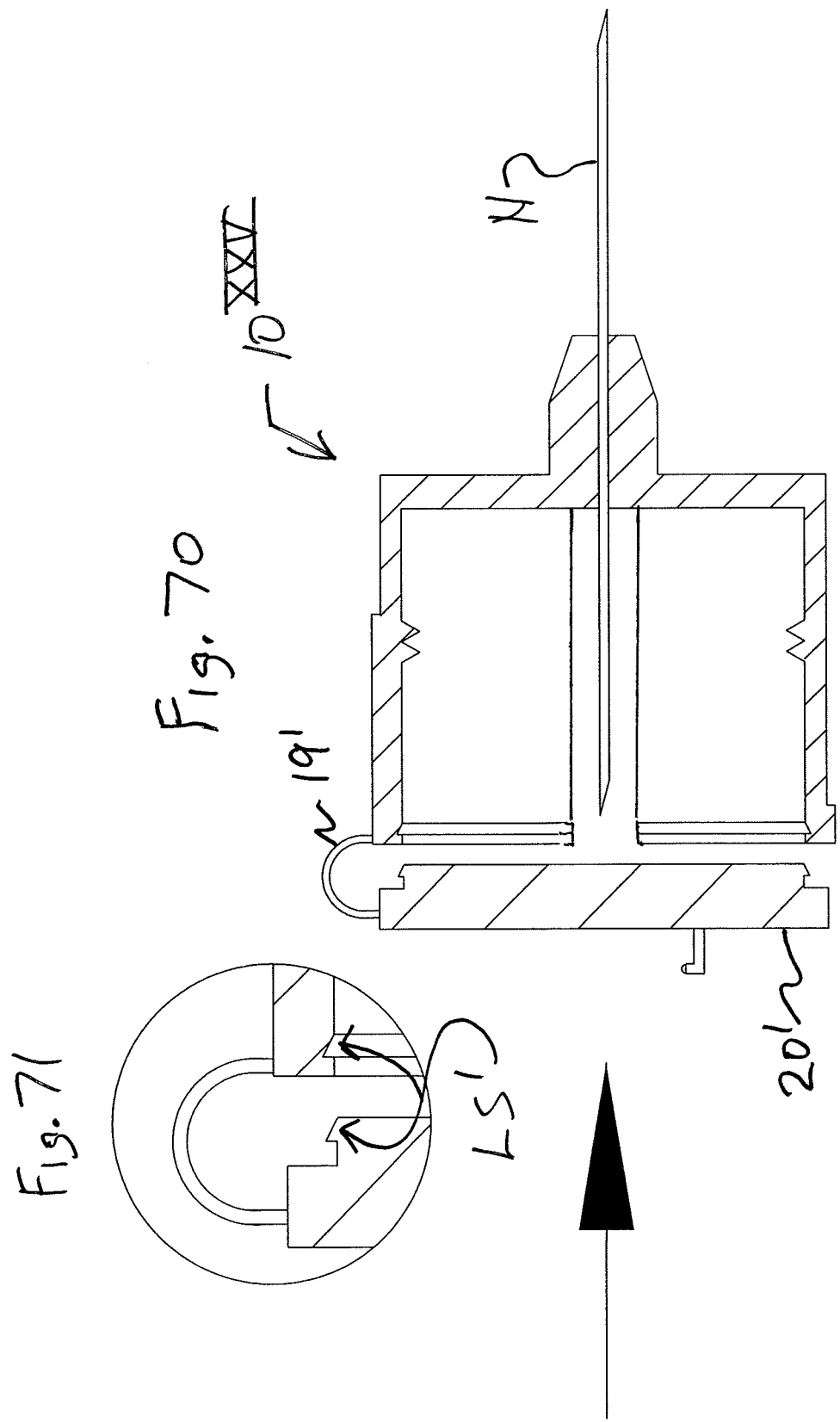

PEN NEEDLE WITH QUICK RELEASE AND/OR REMOVAL SYSTEM

CROSS-REFERENCE TO RELATED APPLICATIONS

The instant application is a U.S. non-provisional Application based on U.S. provisional application No. 61/412,986, filed Nov. 12, 2010, the disclosure of which is hereby expressly incorporated by reference hereto in its entirety.

BACKGROUND OF THE INVENTION

1. Field of the Invention

This invention relates generally to pen injection devices, e.g., pre-loaded syringes, such are utilized for injection of medicament into the body tissues of human and animal patients. More specifically, this invention relates to a removable pen needle which is more easily removed from the pen injection device. The pen needle can preferably include an arrangement that allows the pen needle to be installed axially without requiring it to be rotated and to also be removed axially without requiring it to be rotated.

This invention also relates to a method of using pen needles for pen injection devices wherein the pen needle is configured to be used with conventional the pen injection device.

This invention also relates to a method of using pen injection devices more safely, i.e., reducing the chance that the user will be pricked when handling and/or attempting to remove the pen needle from the pen injection device.

2. Discussion of Background Information

U.S. Pat. No. 4,973,318, the disclosure of which is hereby expressly incorporated by reference in its entirety, discloses a device or disposable syringe includes first and second housing elements which are coupled together for rotation without axial movement therebetween. The first housing element receives a cartridge of a solution to be injected, and mounts a liquid outlet needle at its front end. A piston rod is disposed in the second housing element to move axially therein, and this piston rod includes a rod element and a nut element. The rod element is coupled to the first housing element to move axially therein without relative rotation therewith, and the nut element is threaded to the rod element for telescoping movement therewith and is configured to move axially in the second housing element without relative rotation therein. A pressure receiving element is mounted on the nut element. The housing, rod, nut and pressure receiving elements cooperate such that relative rotation between the housing elements in a selected direction causes relative rotation between the nut and rod elements and thereby increases the effective length of the piston rod and causes the pressure receiving element to extend from the second housing element. A protective cap is removably mounted over the first housing element and is configured to abut second housing element while mounted in place on the first housing element. This protective cap is engaged with the first housing element such that rotation of the cap with respect to the second housing element causes rotation of the first housing element with respect to the second housing element.

This type of device or syringe is shown in FIGS. 1 and 2 of U.S. 2010/0292654 (U.S. Ser. No. 12/779,472) to SCHRAGA filed on May 13, 2010, the disclosure of which is hereby expressly incorporated by reference in its entirety, wherein the pre-loaded syringe 1 has a proximal threaded end 2 which is configured to accept a needle tip assembly consisting of a needle tip 5, a needle tip cover, and a needle cover. A user installs the needle tip assembly 5 onto the end 2, after removing the assembly from its individual package, onto the threaded proximal end 2 by simply sliding it onto the end 2 axially. Because internal threads of the needle tip 5 are mounted to radially deflectable members, installation over threads of the end 2 occurs with a ratchet effect. This installation is made safe by the covers which ensure that the user will not be pricked by the needle N. Once installed, the user can remove the needle tip cover by simply sliding it off axially. Next, the user can remove the needle cover to expose the needle N. The pen needle device is then made ready for use in providing an injection to the user. After injection, the user will typically remove the needle tip 5 and discard the same. To accomplish the removal, the user will typically reinstall the needle tip cover and rotate it to cause the needle tip to unthread from the threaded end 2 (some users may even install the needle cover prior to installing the cover). Once removed, however, it is still possible to reinstall the used needle tip 5 by simply repeating the steps noted above. Unless the user discards the needle tip 5, it is possible that she or other users will not remember or know that it has already been used. That is, there is nothing to prevent reuse of the needle tip 5 should someone attempt to reinstall the needle tip onto the end 2. Furthermore, if the user is unable to locate the covers (i.e., if they have become lost), he/she must then attempt to grip the needle tip 5 in order to unthread it from the end 2. As is apparent, this action can be risky because the user can possibly inadvertently be pricked by the needle N either in attempting to properly grip the needle tip 5, in the action of rotating it to the point it is removed, or even in the handling of the needle tip 5 after it has been removed and prior to being properly discarded. Still further, if the needle tip 5 is not properly discarded (such as being correctly placed in a sharps container), others may come in contact with the needle tip 5 and possibly become injured thereby.

It is therefore desirable to provide a pen needle system which is safer and/or easier to use compared to the conventional devices discussed above and/or which does not have one or more of the above-noted disadvantageous.

SUMMARY OF THE INVENTION

According to one non-limiting embodiment of the invention, there is provided an injection device tip comprising a body configured to be removably connected to an injection device. A needle has a first portion projecting out from the body and a second portion projecting into a space within the body. The body at least one of has at least one slot separating flexible portions which can be deflected outwardly to cause release of an engagement between the body and a proximal end of the injection device, has at least one slot separating flexible portions which can be deflected outwardly to cause release of a thread engagement, has at least one frangible connection arranged on the body, has at least one indicator arrangement on the body which provides a visual indication that the pen needle has been previously used, and has at least one spacing separating two generally semi-circular or generally semi-cylindrical flexible portions which can be deflected outwardly.

According to one non-limiting embodiment of the invention, the tip may further comprise a main outer cover structured and arranged to receive therein or substantially cover the body and the first portion of the needle.

According to one non-limiting embodiment of the invention, the body may comprise at least one internal thread section or partial thread section for engaging an external thread of the proximal end of the injection device.

According to one non-limiting embodiment of the invention, once installed, the tip is capable of threadably engaging with the proximal end of the injection device.

According to one non-limiting embodiment of the invention, the body comprises at least one partial internal thread section for engaging an external thread of the proximal end of the injection device.

According to one non-limiting embodiment of the invention, the body comprises at least two oppositely arranged partial internal thread sections for engaging an external thread of the proximal end of the injection device.

According to one non-limiting embodiment of the invention, the body further includes at least one grippable projection which can be deflected inwardly to cause release of an engagement between the body and a proximal end of the injection device.

According to one non-limiting embodiment of the invention, the body has a generally oval shaped cross-section at least in an area of the body located closer to a rear end of the body than to a front end of the body.

According to one non-limiting embodiment of the invention, the body includes flexible semi-cylindrical wall portions which can be deflected outwardly to cause release of an engagement between the body and a proximal end of the injection device and is generally circular in shape.

According to one non-limiting embodiment of the invention, the body includes flexible semi-cylindrical wall portions which can be deflected outwardly to cause release of an engagement between the body and a proximal end of the injection device and is generally non-circular in shape.

According to one non-limiting embodiment of the invention, the body includes at least one gripping or flexible portion arranged radially outside an imaginary circle defined by a generally cylindrical rear edge of the body.

According to one non-limiting embodiment of the invention, the body includes the two oppositely arranged gripping or flexible portions arranged outside an imaginary circle defined by a generally cylindrical rear edge of the body.

According to one non-limiting embodiment of the invention, the tip further comprises a safety shield adapted to cover the needle.

According to one non-limiting embodiment of the invention, the tip further comprises a safety shield movably mounted to the body and being adapted to cover the needle.

According to one non-limiting embodiment of the invention, the tip further comprises a safety shield movably mounted to the proximal end of the body.

According to one non-limiting embodiment of the invention, the tip further comprises a safety shield of the type described in U.S. 2010/0292654.

According to one non-limiting embodiment of the invention, there is provided a method of removing the tip of any one of the herein described features, wherein the method comprises installing the tip onto a proximal end of an injection device axially and without rotation and removing the tip after applying a squeezing force to opposite sides of the body.

According to one non-limiting embodiment of the invention, there is provided a method of removing the tip of any one of the herein described features, wherein the method comprises installing the tip onto a proximal end of an injection device and removing the tip axially and without rotation after applying a squeezing force to opposite sides of the body.

According to one non-limiting embodiment of the invention, there is provided a method of removing the tip of any one of the herein described features, wherein the method comprises installing the tip onto a proximal end of an injection device axially and without rotation and removing the tip axially and without rotation after applying a squeezing force to opposite sides of the body.

According to one non-limiting embodiment of the invention, there is provided a pre-filled injection device comprising at least one feature of the tip shown in at least one drawing of the instant application.

According to one non-limiting embodiment of the invention, there is provided an injection device tip comprising a one-piece body configured to be removably connected to an injection device and a needle having a first portion projecting out from a front wall of the body and a second portion projecting into a space within the body. The body at least one of has at least one slot separating flexible portions which can be deflected outwardly to cause release of an engagement between the body and a proximal end of the injection device, has at least one slot separating flexible portions which can be deflected outwardly to cause release of a thread engagement, has at least one frangible connection arranged on the body, has at least one indicator arrangement on the body which provides a visual indication that the pen needle has been previously used, and has at least one spacing separating two generally semi-circular or generally semi-cylindrical flexible portions which can be deflected outwardly.

According to one non-limiting embodiment of the invention, there is provided an injection device tip comprising a body configured to be removably connected to an injection device and comprising at least one semi-cylindrical wall defining an internal space and a needle having a first portion projecting out from a front wall of the body and a second portion projecting into the internal space. The body at least one of has at least one slot separating flexible portions which can be deflected outwardly to cause release of an engagement between the body and a proximal end of the injection device, has at least one slot separating flexible portions which can be deflected outwardly to cause release of a thread engagement, has at least one frangible connection arranged on the body, has at least one indicator arrangement on the body which provides a visual indication that the pen needle has been previously used, and has at least one spacing separating two generally semi-circular or generally semi-cylindrical flexible portions which can be deflected outwardly.

According to one non-limiting embodiment of the invention, there is provided an injection device tip comprising a body configured to be removably connected to an injection device and comprising at least one semi-cylindrical wall defining an internal space, a needle having a first portion projecting out from a front wall of the body and a second portion projecting into the internal space, and a device structured and arranged to prevent a user from being pricked by the second portion. The device is at least one of coupled to the body via a living hinge, movable from an original position to a position covering the second portion, movable parallel to an axis of the needle, movable between unlocked position and a locked position, and an axially movable needle shield that has at least a portion that moved within the internal space.

Other exemplary embodiments and advantages of the present invention may be ascertained by reviewing the present disclosure and the accompanying drawing.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein:

FIG. 14 shows the pen needle of FIG. 11 with a broken frangible section;

FIG. 15 shows an enlarged portion of FIG. 14;

FIG. 16 shows a side view of a fifth non-limiting embodiment of a pen needle or tip assembly in according to the invention. This embodiment is similar to that of FIG. 11 except that it uses narrower slots in the body;

FIG. 17 shows a sixth non-limiting embodiment of a pen needle or tip assembly during installation in according to the invention. This embodiment is similar to that of FIG. 3 except that it uses a closable rear cap on the body. The rear cap is shown retained in an initial position;

FIG. 18 shows the installed pen needle of FIG. 17 with a the rear cap disconnected from the outer cap;

FIG. 19 shows the en needle of FIG. 17 removed from the injection device and with the outer cap installed thereon and with the rear cap moving to close off a rear open end of the pen needle;

FIGS. 20-22 show a seventh non-limiting embodiment of a pen needle or tip assembly in according to the invention. FIG. 20 shows a side cross-section view of the pen needle. FIG. 21 shows a rear end view of the pen needle shown in FIG. 20. FIG. 22 shows the view of FIG. 21 when the pen needle experiences radial and/or circumferential expansion;

FIG. 23 shows a side cross-section view of the pen needle. FIG. 23 shows a rear end view of the pen needle shown in FIG. 22;

FIG. 25 shows a side cross-section view of the pen needle. FIG. 26 shows a rear end view of the pen needle shown in FIG. 25;

FIG. 27 shows a side cross-section view of the pen needle. FIG. 28 shows a rear end view of the pen needle shown in FIG. 27;

FIG. 29 shows a side cross-section view of the pen needle. FIG. 30 shows a rear end view of the pen needle shown in FIG. 29;

FIG. 31 shows a side cross-section view of the pen needle. FIG. 32 shows a rear end view of the pen needle shown in FIG. 31;

FIG. 33 shows a side cross-section view of the pen needle. FIG. 34 shows a rear end view of the pen needle shown in FIG. 33;

FIG. 35 shows a side cross-section view of the pen needle. FIG. 36 shows a rear end view of the pen needle shown in FIG. 35;

FIG. 37 shows a side cross-section view of the pen needle. FIG. 38 shows a rear end view of the pen needle shown in FIG. 37;

FIGS. 39-42 show another non-limiting embodiment of a pen needle or tip assembly in according to the invention. FIG. 39 shows a side cross-section view of the pen needle. FIG. 40 shows a rear end view of the pen needle shown in FIG. 39. FIG. 41 shows a partial side cross-section view of the pen needle of FIG. 39 rotated 90 degrees. FIG. 42 shows a rear end view of the pen needle shown in FIG. 41;

FIG. 43 shows a side cross-section view of the pen needle. FIG. 44 shows a rear end view of the pen needle shown in FIG. 43. FIG. 45 shows a partial side cross-section view of the pen needle of FIG. 43 rotated 90 degrees. FIG. 46 shows a rear end view of the pen needle shown in FIG. 45;

FIGS. 47-49 show another non-limiting embodiment of a pen needle or tip assembly in according to the invention. FIG. 47 shows a side cross-section view of the pen needle. FIG. 48 shows a rear end view of the pen needle shown in FIG. 47. FIG. 49 shows the view of FIG. 48 when the pen needle experiences radial and/or circumferential expansion;

FIGS. 50-52 show another non-limiting embodiment of a pen needle or tip assembly in according to the invention. FIG. 50 shows a side cross-section view of the pen needle. FIG. 51 shows a rear end view of the pen needle shown in FIG. 50. FIG. 52 shows the view of FIG. 51 when the pen needle experiences radial and/or circumferential expansion;

FIG. 53 shows a side cross-section view of the pen needle. FIG. 54 shows a rear end view of the pen needle shown in FIG. 53;

FIG. 55 shows a side cross-section view of the pen needle. FIG. 56 shows a rear end view of the pen needle shown in FIG. 55;

FIG. 57 shows a side view of the pen needle. FIG. 58 shows a side cross-section view of the pen needle. FIG. 59 shows a rear end view of the pen needle shown in FIG. 58;

FIGS. 60 and 61 show another non-limiting embodiment of a pen needle or tip assembly in according to the invention. FIG. 60 shows a side cross-section view of the pen needle with the needle guard in a locked covering position. FIG. 61 shows an enlarged view of a portion of FIG. 60;

FIG. 62 shows a side view of the outer cover. FIG. 63 shows a cross-section of FIG. 63 rotated 90 degrees;

FIG. 64 shows a side cross-section view of the inner cover. FIG. 65 shows a rear end view of FIG. 64;

FIG. 66 shows a side cross-section view of the pen needle. FIG. 67 shows a rear end view of FIG. 66;

FIGS. 68 and 69 show another non-limiting embodiment of a pen needle or tip assembly in according to the invention. FIG. 68 shows a side cross-section view of the pen needle. FIG. 69 shows a rear end view of FIG. 68;

FIGS. 70 and 71 show another non-limiting embodiment of a pen needle or tip assembly in according to the invention. FIG. 70 shows a side cross-section view of the pen needle. FIG. 71 shows an enlarged view of a portion of FIG. 70; FIG. 72 shows a side cross-section view of the pen needle with the back cap oriented towards a closed and unlocked initial position. FIG. 73 shows the back cap oriented towards a closed and locked post-use position.

DETAILED DESCRIPTION OF THE INVENTION

Figure 1:
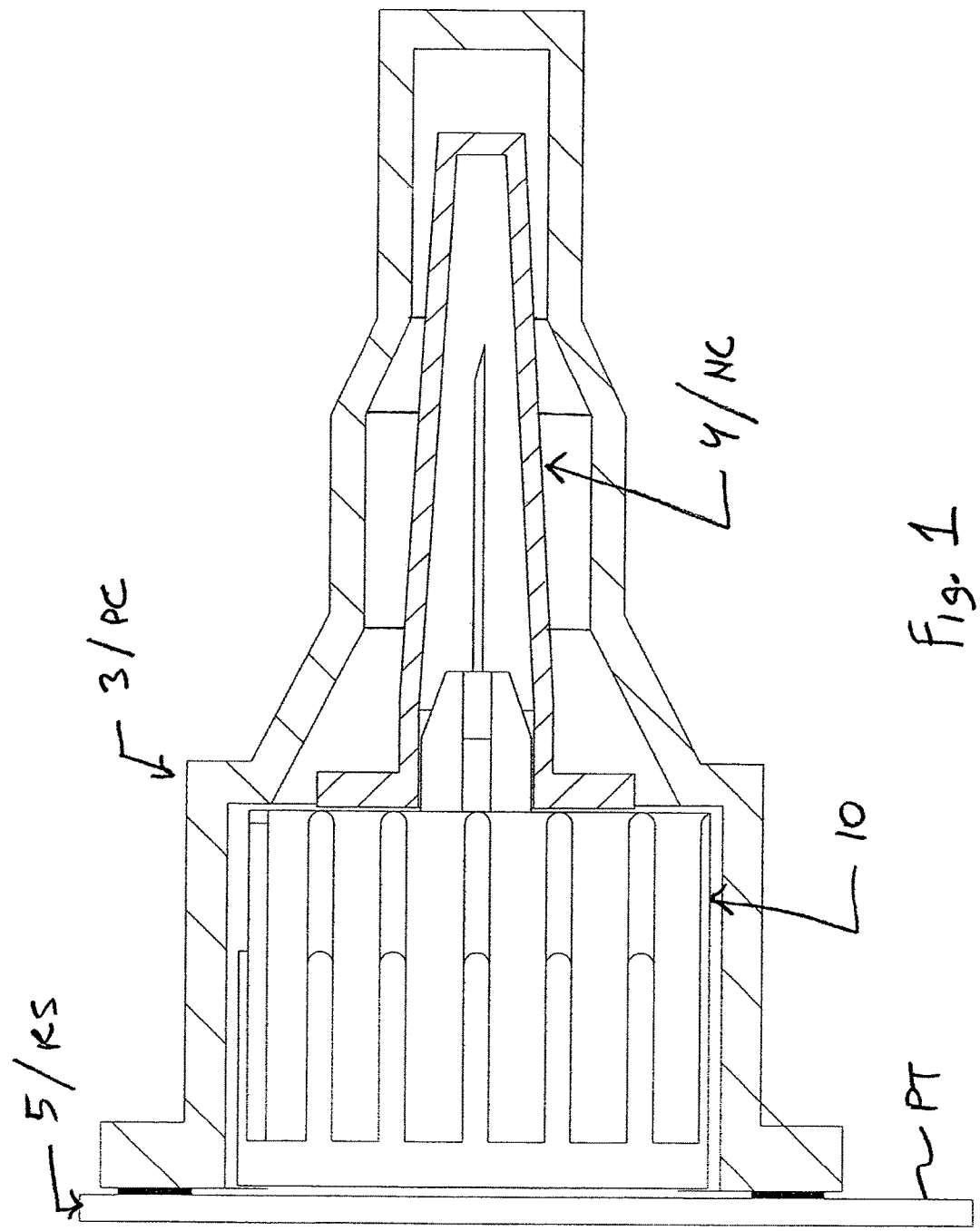
FIG. 1 shows an enlarged side view of a packaged tip assembly utilizing a known outer main protective cover whose rear end is closed off by a known removable seal having a pull tab as well as a known needle cover. A pen needle in accordance with one embodiment of the invention is arranged within the main protective cover.

Referring now to the drawings and first to FIGS. 1-8 which show a first embodiment of a needle tip assembly in each of a packaged configuration (FIG. 1), an installing or installed configuration (FIG. 2), and other states or configurations that will be described in detail.

The needle tip assembly includes a needle tip cap 3 or protective cover PC having various generally cylindrical portions with different diameters, a needle cap NC or 4, and a needle tip or pen needle 10. The proximal end of the needle tip cap 3 is closed while the distal end is open and includes a circumferential flange. The proximal end of the needle cap 4 is similarly closed while the distal end is open and includes a circumferential flange. Both types of caps 3 and 4 are generally known and can be of any type conventional or otherwise.

Figure 2:
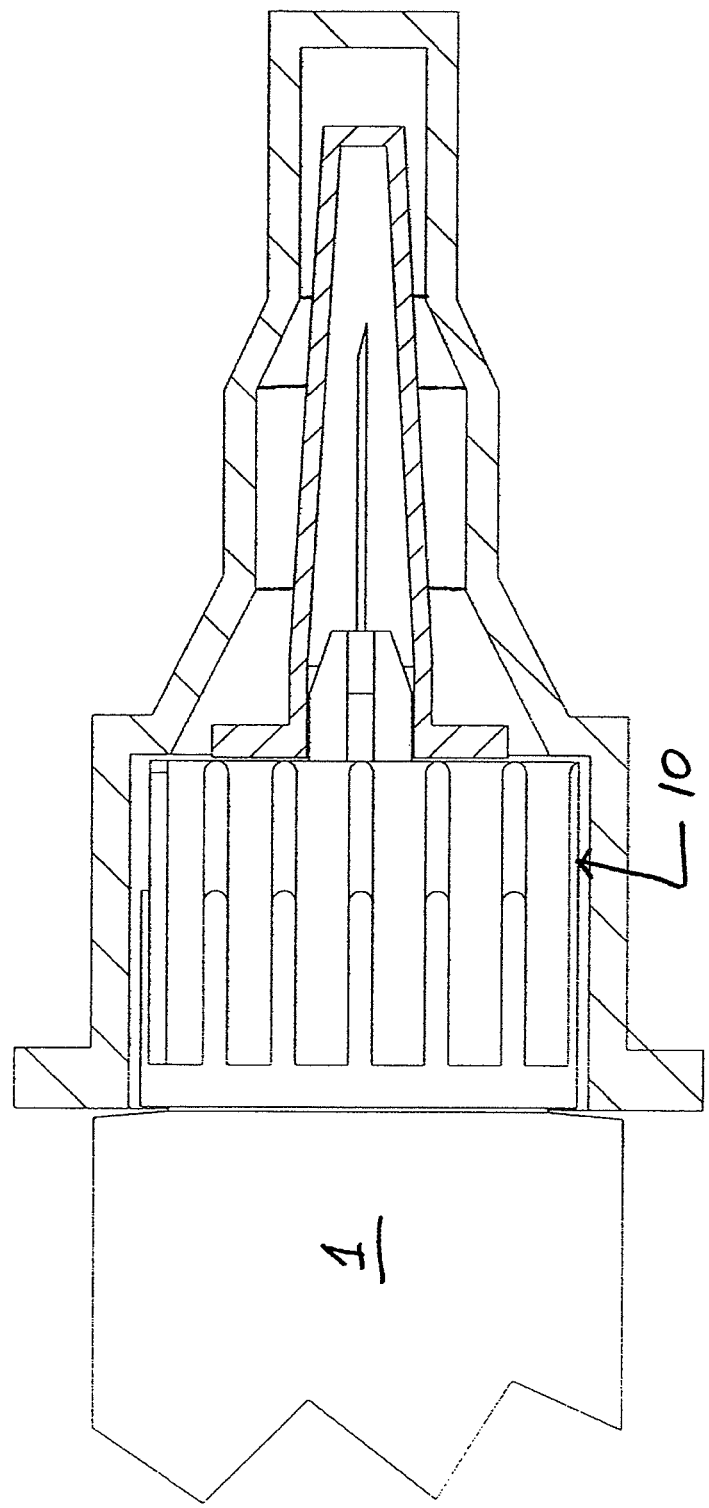
FIG. 2 shows how the pen needle of the invention can be installed on a known pre-loaded injection device.
Figure 3:
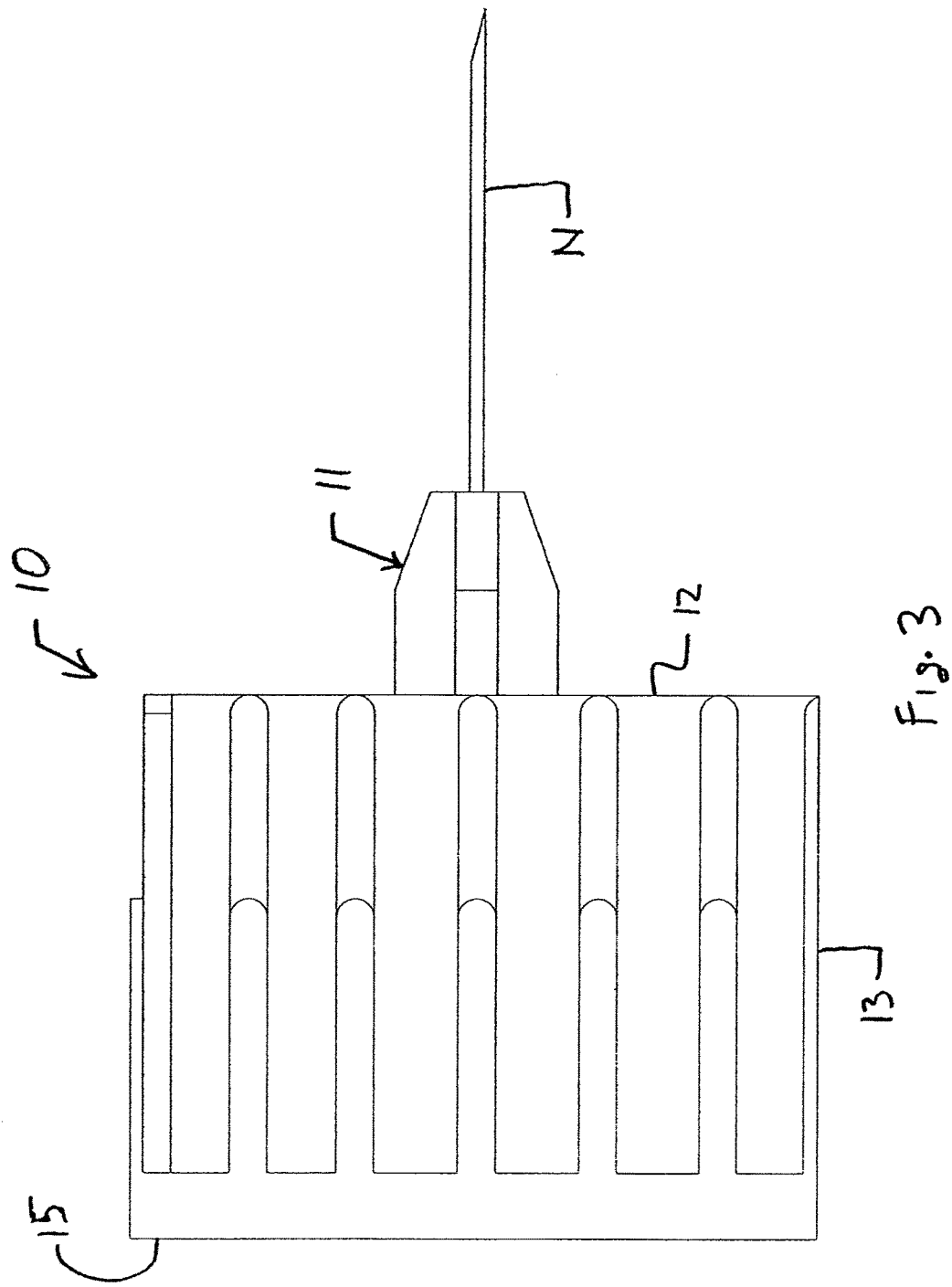
FIG. 3 shows side view of a first non-limiting embodiment of a pen needle or tip assembly according to the invention.
Figure 4:
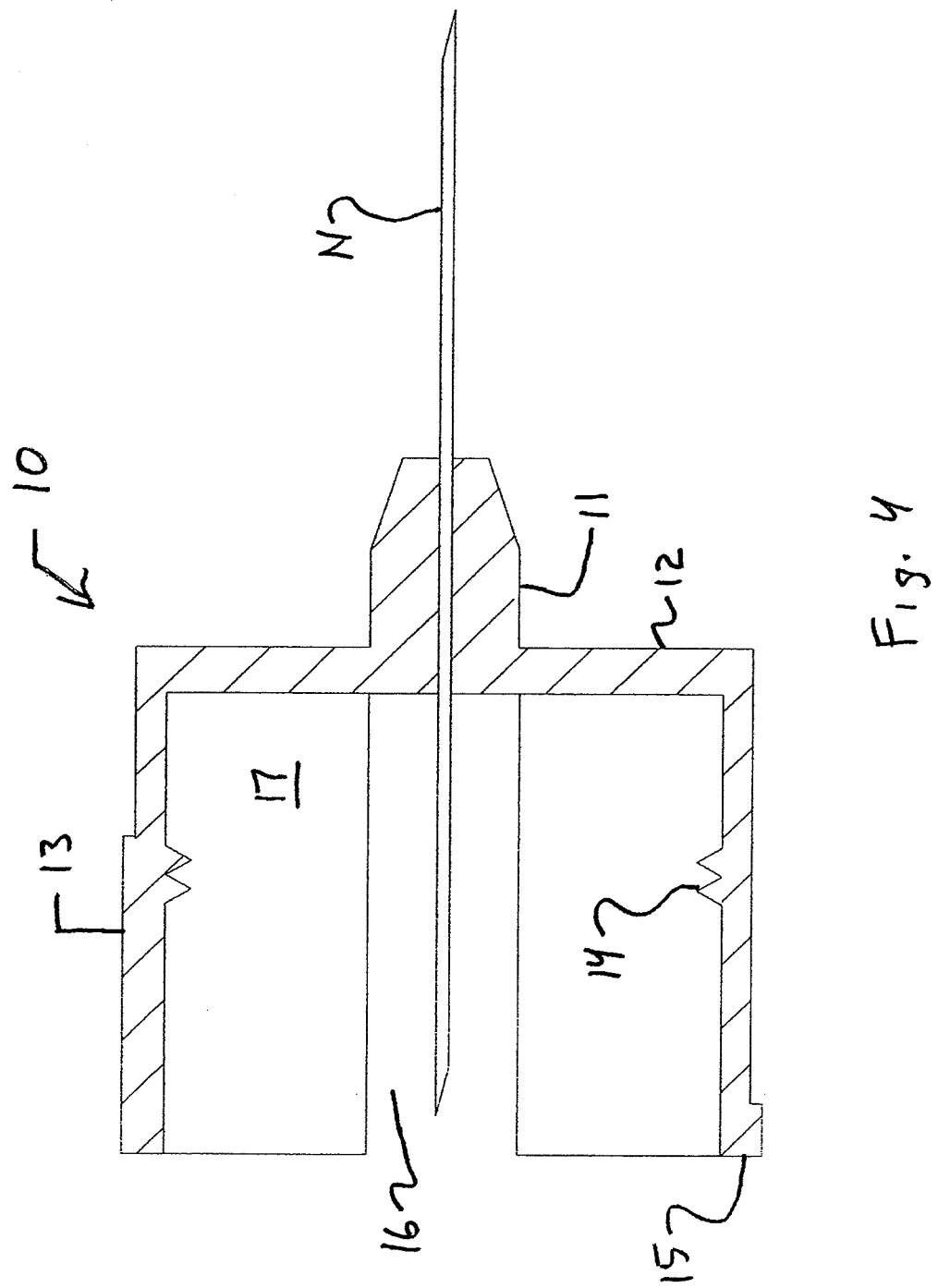
FIG. 4 shows a cross-section view of FIG. 3. The hollow double-ended needle is not shown in cross-section.
Figure 5:
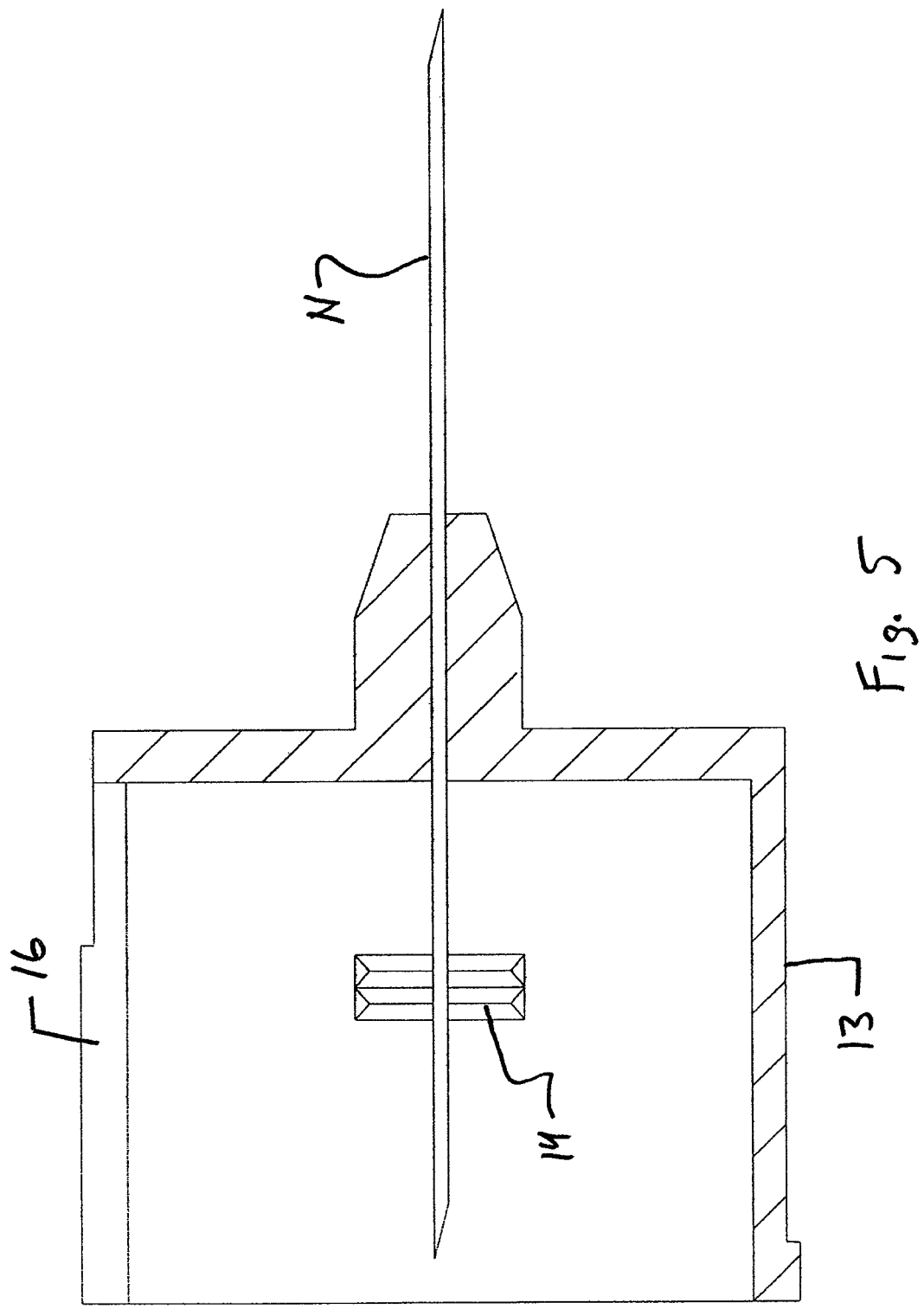
FIG. 5 shows the cross-section view of FIG. 4 rotated 90 degrees.
Figure 6:
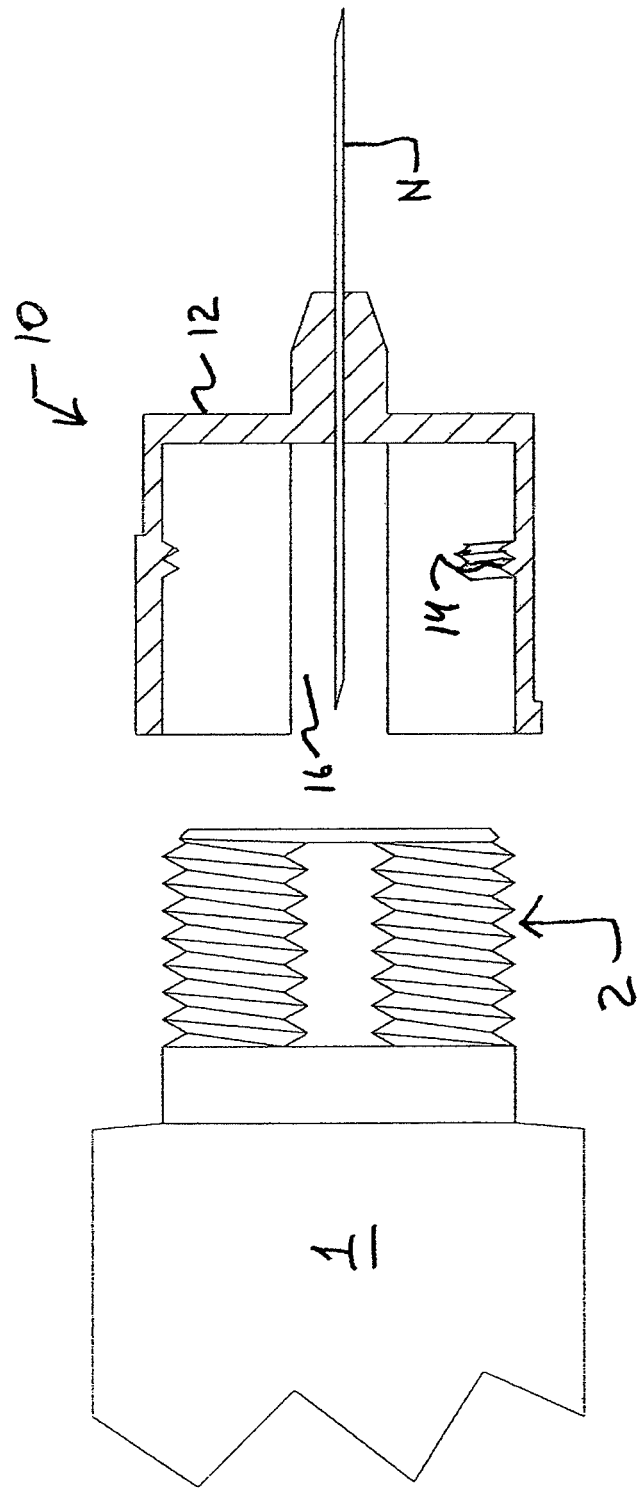
FIG. 6 shows the pen needle of FIG. 4 before being installed on an injection device.
Figure 7:
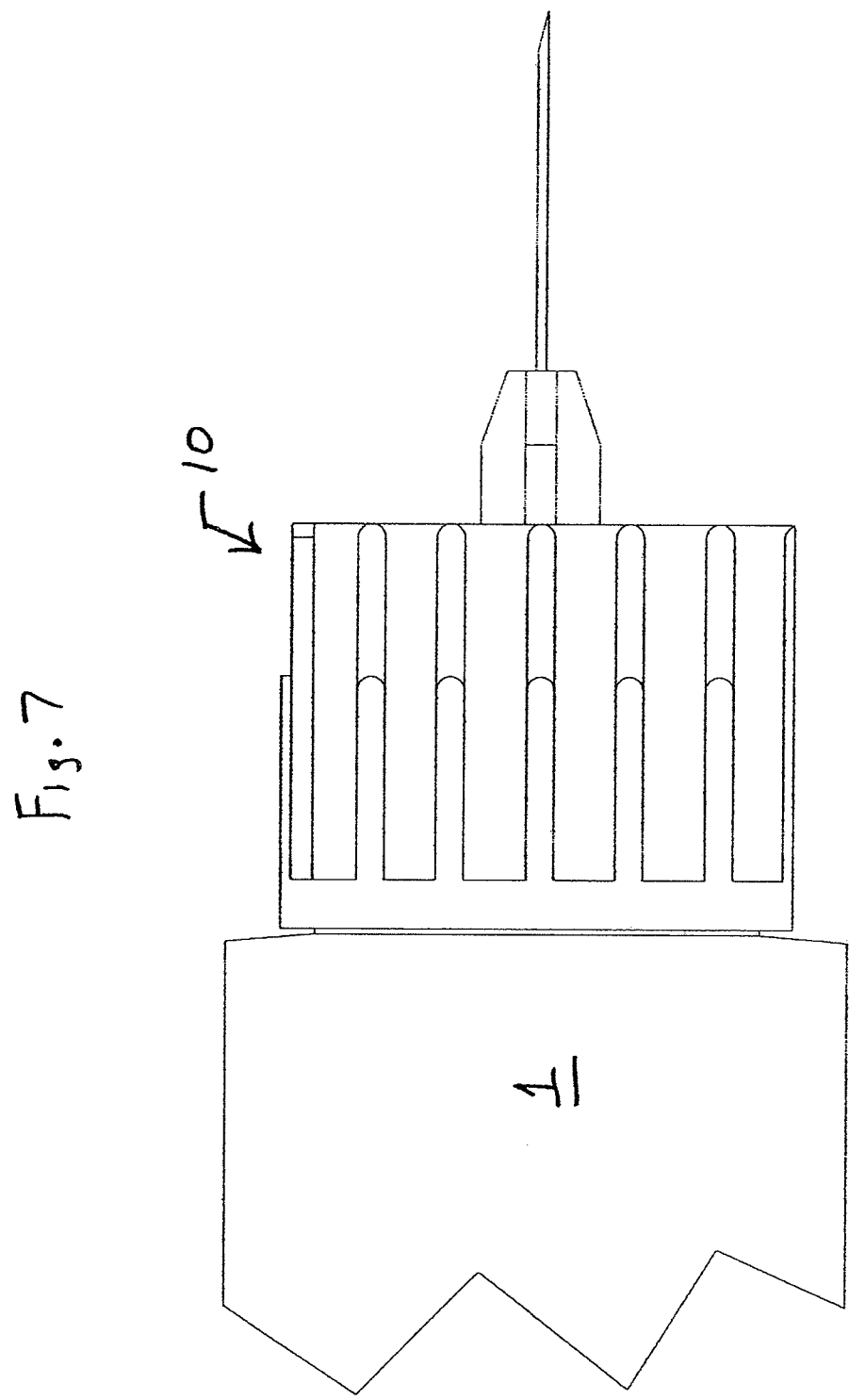
FIG. 7 shows the pen needle of FIG. 3 installed on an injection device.
Figure 8:
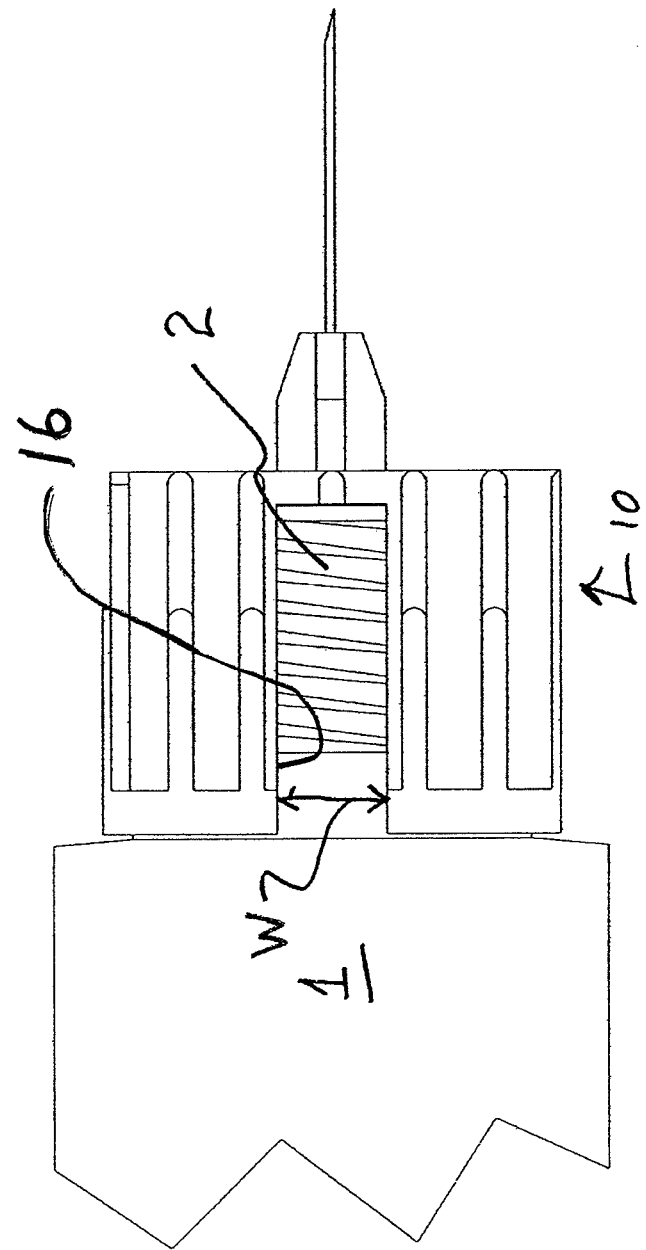
FIG. 8 shows the view of FIG. 7 rotated 90 degrees.

As shown in FIGS. 3-5, the proximal end of the needle tip 10 includes a needle N while the distal end 15 is open and includes an interior space or opening 17 which is sized to allow the needle tip 10 to be mounted onto the threaded proximal end 2 of the pen needle device 1 (see FIG. 2 or FIGS. 6 and 7). The pen needle 10 also includes a proximal hub 11, a wall 12, a generally cylindrical sidewall 13, one or more thread sections 14, and at least one sidewall slot 16. In embodiments, the slot 16 extends all the way from the distal end 15 to the distal end of the wall 12 (see FIG. 4). The slot 16 allows the sidewall 13 to deflect inwardly or outwardly so that the thread sections 14 can engage with the thread section 2 in, e.g., two ways. One way relates to the typical threaded connection. That is, when, during installation or removal, the pen needle 10 is rotated relative to the section 2 of the injection device 1, the thread sections 14 engage with the threads 2 so that rotation in one direction causes the pen needle 10 to move towards the injection device 1 (during installation) and rotation in another direction causes the pen needle 10 to move away from the injection device 1 (during removal). Another way relates to how the pen needle 10 can be slid or pulled off or on axially and without rotation relative to the section 2. Because the slot 16 allows the sidewall 13 (or sufficiently weakens it) to expand radially, exerting a sufficient pulling force on the pen needle 10 relative to the device 1 can cause the thread sections 14 to disengage from the threads 2 of the device 1 without significantly damaging or causing shearing of the thread sections 14 and/or the threads 2. The effect is more in the nature of a ratchet effect with the thread sections 14 moving towards and away from the threads 2 as the pen needle 10 is pushed or pulled axially.

In embodiments, the width W (see FIG. 8) of the slot 16 is sufficient to allow viewing of the thread 2 and can be between about 1 mm and about 5 mm, and preferably between about 2 mm and about 3 mm. In embodiments, the width W of slot 16 can be any whole number value in "mm" between 1 mm and 5 mm. In embodiments, the width W of the slot 16 is sufficient to allow viewing of all the thread 2 length (or at least a proximal part of the threads up to the wall 12) and also to provide a visual indication that the pen needle 10 is fully installed on the device 1.

In the instant embodiment, prior the needle tip assembly (see FIG. 1) being installed onto the threaded proximal end 2, a user removes the material 5 or RS by pulling on the pull tab PT. Then, the user slides the assembly of FIG. 1 (with the material 5 removed) onto the proximal end 2, i.e., by axially sliding it on or by threading it on as shown in FIG. 2. Unlike many prior art pen needles, the embodiment of FIGS. 1-8 provides that installation can occur without threading-on of the pen needle 10. Moreover, removal can also occur without threading-on of the pen needle 10 owing to the ability of the side wall 13 to deflect which allows the thread sections 14 to move in an out (or deflect) relative to the threads of the section 2. Prior to use, the caps 3 and 4 are removed so that the injection device resembles the configuration of FIGS. 7 and 8.

Once the injection device with the installed needle tip assembly has been used to perform an injection, the needle tip 10 can be removed in the following ways: one could simply grip the needle tip 10 in the area of the sidewall 13 and unthread it from the threaded proximal end 2. This is risky, of course, because the user can be inadvertently be pricked by the exposed needle N; one could also re-install the needle cap 4 and then grip the needle tip 10 in the area of the sidewall 13 and unthread it from the threaded proximal end 2; one could re-install both the needle cap 4 and the needle tip cap 3, and then grip the needle tip cap 3 in the area just in front of the distal flange and thereafter unthread the entire needle tip assembly thereby causing the needle tip 10 to become unthreaded from the threaded proximal end 2; one could re-install only the needle tip cap 3, and then grip the needle tip cap 3 in the area just in front of the distal flange and thereafter unthread the needle tip assembly (without the cap 4) thereby causing the needle tip 10 to become unthreaded from the threaded proximal end 2. Preferably, however, one can install only the cap 4 (or not) and then grip the sidewall 13 in an area of the wall 12 and then slide the pen needle 10 off axially—without rotating it. This can occur because the slot 16 in the sidewall 13 allows the thread sections 14 to move radially outwardly as the pen needle 10 is moved axially. All of these ways are contemplated by the invention, but the first way is the least desirable.

Figure 9:
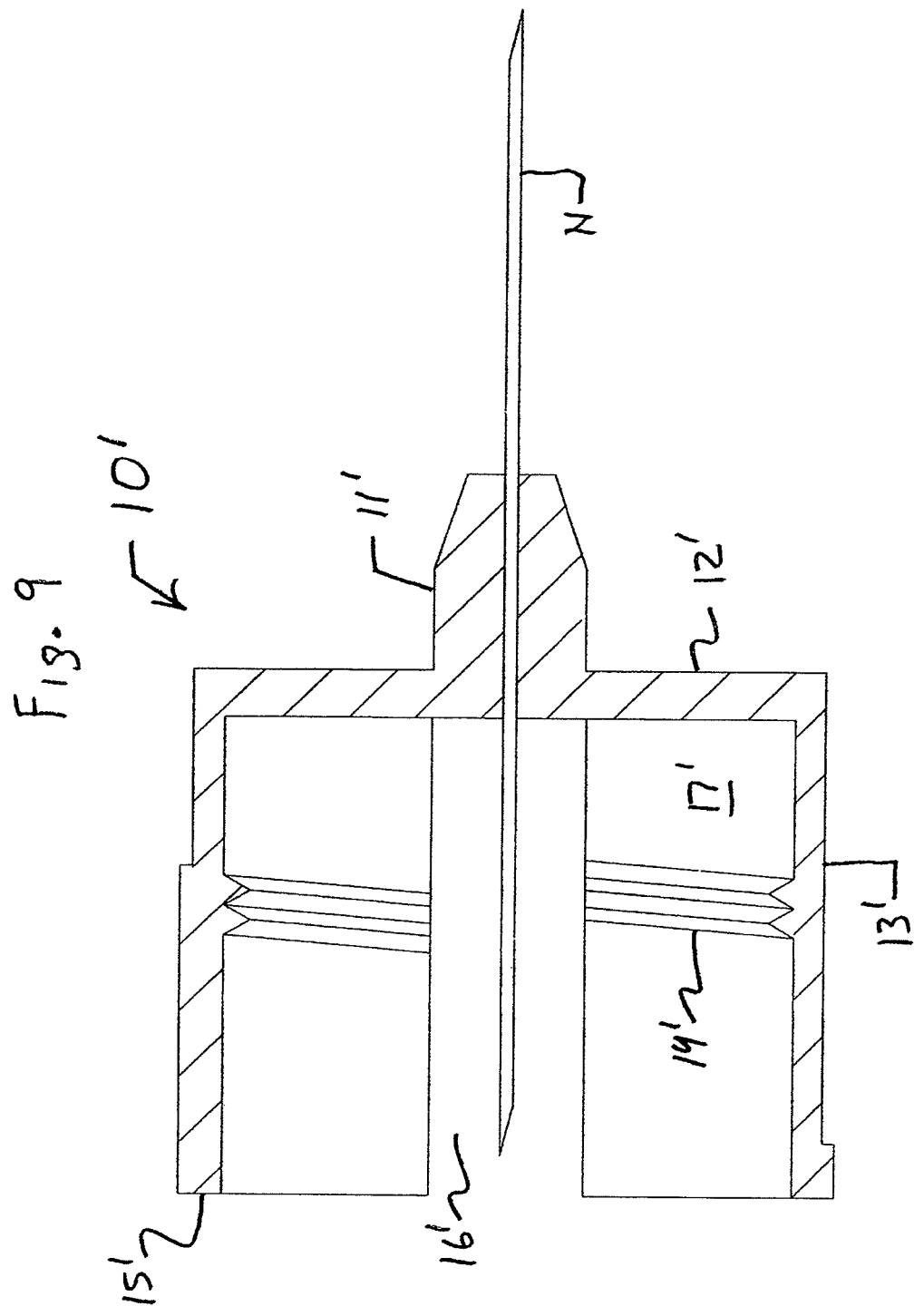
FIG. 9 shows a side cross-section view of a second non-limiting embodiment of a pen needle or tip assembly in according to the invention. This embodiment is similar to that of FIG. 3 except that it uses a nearly full internal thread and that is interrupted by a slot.

FIG. 9 shows another embodiment of a pen needle 10'. As with the previous embodiment, the proximal end of the needle tip 10' includes a needle N while the distal end 15' is open, includes an inner needle (or inner portion of double-ended needle) in fluid communication with needle N, and includes an interior space or opening 17' which is sized to allow the needle tip 10' to be mounted onto the threaded proximal end 2 of the pen needle device 1 (see FIG. 2 or FIGS. 6 and 7). The pen needle 10' also includes a proximal hub 11', a wall 12', a generally cylindrical sidewall 13', and a continuous thread section 14 which is interrupted by at least one sidewall slot 16'. In embodiments, the slot 16' extends all the way from the distal end 15' to the distal end of the wall 12' (see FIG. 9). The slot 16' allows the sidewall 13' to deflect inwardly or outwardly so that the thread section 14' can engage with the thread section 2 in that the pen needle 10' can more easily (i.e., with less friction) be threaded on and threaded off. This embodiment can also otherwise utilize features similar to that shown in FIG. 1 such as features 3, 4 and 5.

Figure 10:
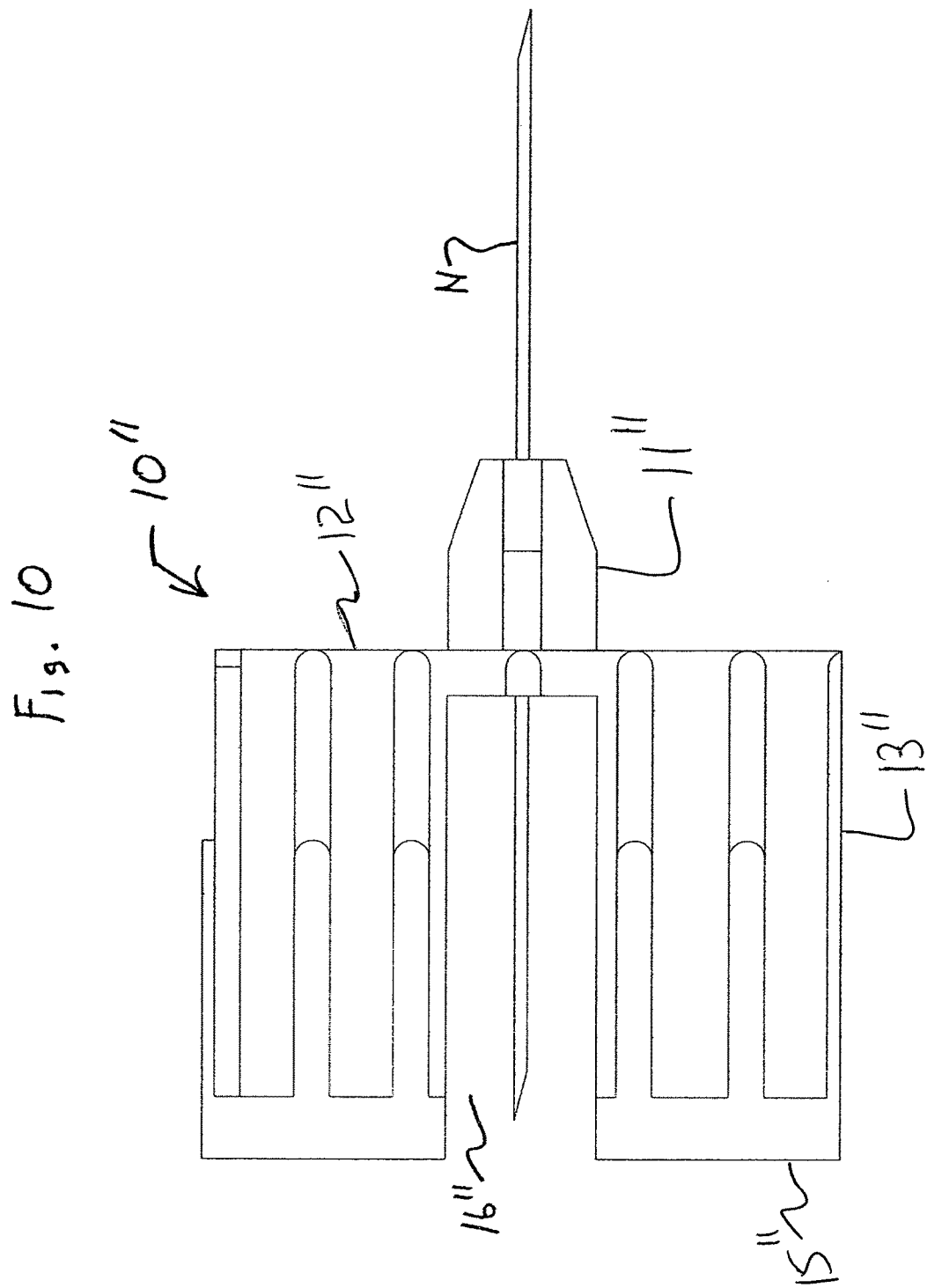
FIG. 10 shows a side view of a third non-limiting embodiment of a pen needle or tip assembly in according to the invention. This embodiment is similar to that of FIG. 3 except that it uses two oppositely arranged slots in or on the body.
Figure 11:
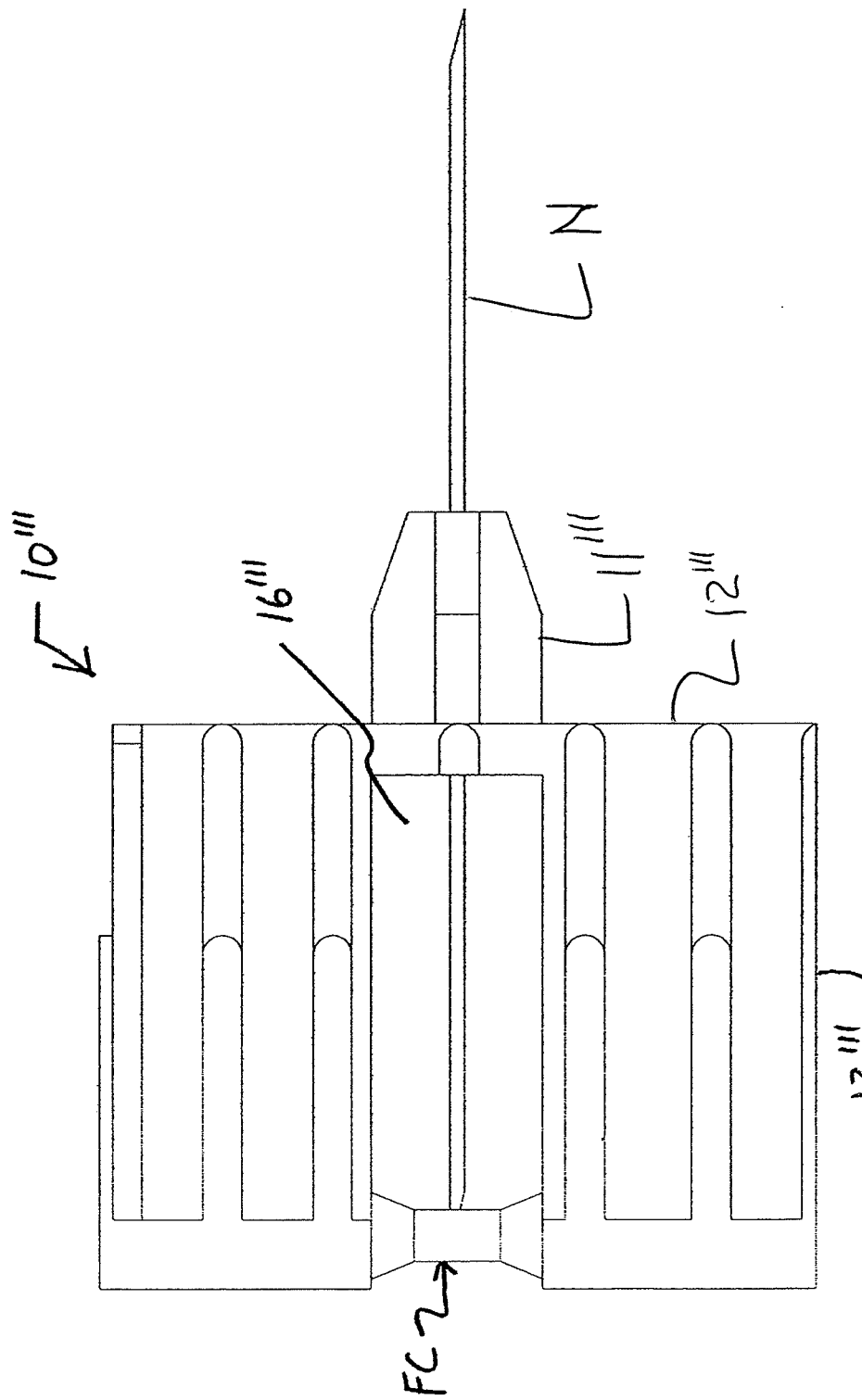
FIG. 11 shows a side view of a fourth non-limiting embodiment of a pen needle or tip assembly in according to the invention. This embodiment is similar to that of FIG. 10 except that it uses frangible connections arranged in the slots in the body.
Figure 12:
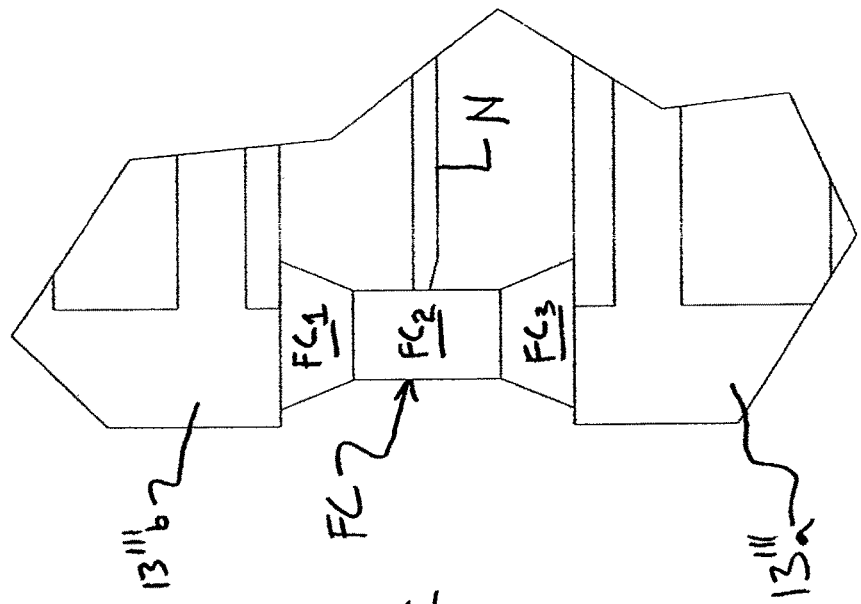
FIG. 12 shows an enlarged side view of a portion of the pen needle shown in FIG. 11.
Figure 13:
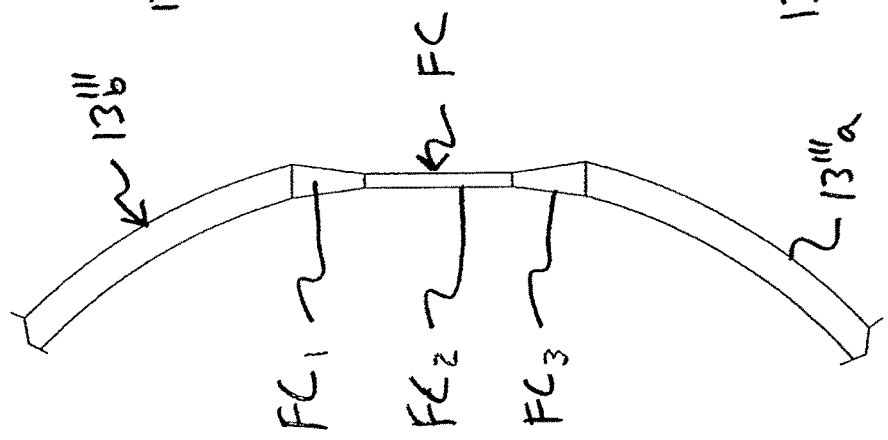
FIG. 13 shows a rear view of a portion of FIG. 12.

FIG. 10 shows another embodiment of a pen needle 10". As with the previous embodiment, the proximal end of the needle tip 10" includes a needle N while the distal end 15" is open and includes an interior space or opening 17" which is sized to allow the needle tip 10" to be mounted onto the threaded proximal end 2 of the pen needle device 1 (see FIG. 2 or FIGS. 6 and 7). The pen needle 10" also includes a proximal hub 11", a wall 12", a generally cylindrical sidewall 13", and a continuous thread section (not shown) which is interrupted by plural, and preferably two, three, four, five or six, generally equally spaced (circumferentially or angularly) sidewall slot 16". In embodiments, the slots 16" each extend all the way from the distal end 15" to the distal end of the wall 12' (see FIG. 10). The slot 16" allow the sidewall 13" to deflect inwardly or outwardly so that the thread sections can engage with the thread section 2 in, e.g., two ways, as noted in the previous embodiment. This embodiment can also otherwise utilize features similar to that shown in FIG. 1 such as features 3, 4 and 5.

FIGS. 11-15 show another embodiment of a pen needle 10'''. As with the previous embodiment, the proximal end of the needle tip 10''' includes a needle N while the distal end 15''' is open and includes an interior space or opening which is sized to allow the needle tip 10''' to be mounted onto the threaded proximal end 2 of the pen needle device 1 (see FIG. 2 or FIGS. 6 and 7). The pen needle 10''' also includes a proximal hub 11''', a wall 12''', a generally cylindrical sidewall 13''', and a thread section (not shown but either a continuous one like FIG. 9 or relatively short thread sections like those shown in FIG. 5) which is interrupted by or arranged between or arranged on one side of, at least one sidewall slot 16'''. In embodiments, the slot 16''' extends all the way from the distal end 15''' to the distal end of the wall 12''' (see FIG. 11). Unlike previous embodiments, however, this embodiment utilize one or more breakable or fracturable connecting sections FC. Once the section(s) FC is broken (see FIGS. 14 and 15), the slot 16''' allows the sidewall 13''' to deflect inwardly or outwardly so that the thread section can engage with the thread section 2 in that the pen needle 10''' can more easily slide axially off threaded section 2. This embodiment can also otherwise utilize features similar to that shown in FIG. 1 such as features 3, 4 and 5.

FIGS. 12-15 show the generally cylindrical sidewall 13''' in the area of the breakable or fracturable connecting section FC. As is apparent, the section(s) FC is integrally formed with the sidewall 13''' and connects one sidewall portion 13'''a to another sidewall portion 13'''b. Each section(s) FC is made up of a first connecting section $FC_1$, a weaker (in tension) second connecting section $FC_2$ designed or configured to experience the breaking, and a third connecting section $FC_3$, connects one sidewall portion 13'''a to another sidewall portion 13'''b. FIG. 15 shows what happens when the user attempts to slide the pen needle 10''' off the injection device causing the fracture in section $FC_2$. The preferred way to use this embodiment is to thread on the pen needle 10''' and then pull it off axially. The fracture can this provide a visual indication to the user that the pen needle 10''' has been previous used.

FIG. 16 shows another embodiment of a pen needle $10^{IV}$. As with the previous embodiment, the proximal end of the needle tip $10^{IV}$ includes a needle N while the distal end is open and includes an interior space or opening which is sized to allow the needle tip $10^{IV}$ to be mounted onto the threaded proximal end of the pen needle injection device. The pen needle $10^{IV}$ also includes a proximal hub, a wall, a generally cylindrical sidewall $13^{IV}$, and a thread section (not shown but either a continuous one like FIG. 9 or relatively short thread sections like those shown in FIG. 5) which is interrupted by or arranged between or arranged on one side of, at least one sidewall slot $16^{IV}$. In embodiments, the slot $16^{IV}$ extends all the way from the distal end to the distal end of the wall (see FIG. 16). Like a previous embodiment, this embodiment utilize one or more breakable or fracturable connecting sections FC. The \section(s) FC, however, is arranged essentially at the distal end and in an area of the sidewall $13^{IV}$ that is significantly wider than a majority of the narrower slot $16^{IV}$. This embodiment can otherwise function in the same way as the previous embodiment and can also otherwise utilize features similar to that shown in FIG. 1 such as features 3, 4 and 5.

FIGS. 17-19 show an embodiment of a pen needle $10^V$ which utilizes a modified outer cover $3^V$. This embodiment is similar to any of the previous embodiments such as that of FIGS. 1-8 except that the body of the needle tip $10^V$ includes a living hinge 19 connecting the body to a distal end cap or cover 20. In the position shown in FIG. 17, the cover 20 is retained in an initial position. This is ensured with a locking projection being releasably engaging with a locking projection arranged on the cap $3^V$ (see FIG. 17). After the user installs the pen needle $10^V$ on the device as shown in FIG. 17, the user can remove the cover $3^V$ by first disengaging or unlocking the cover 20 therefrom as shown in FIG. 18. The user can then remove the cover $3^V$ and use the injection device to inject a substance. Thereafter, the user can reinstall the cover $3^V$ as shown in FIG. 19 and move the cover 20 to a position closing off the distal end of pen needle $10^V$. Unlike previous embodiments, this embodiment ensures that both needles N are covered allowing the user pen needle to be more safely disposed of. One or more features of this embodiment can be utilized on any of the other embodiments disclosed herein.

Figure 22:
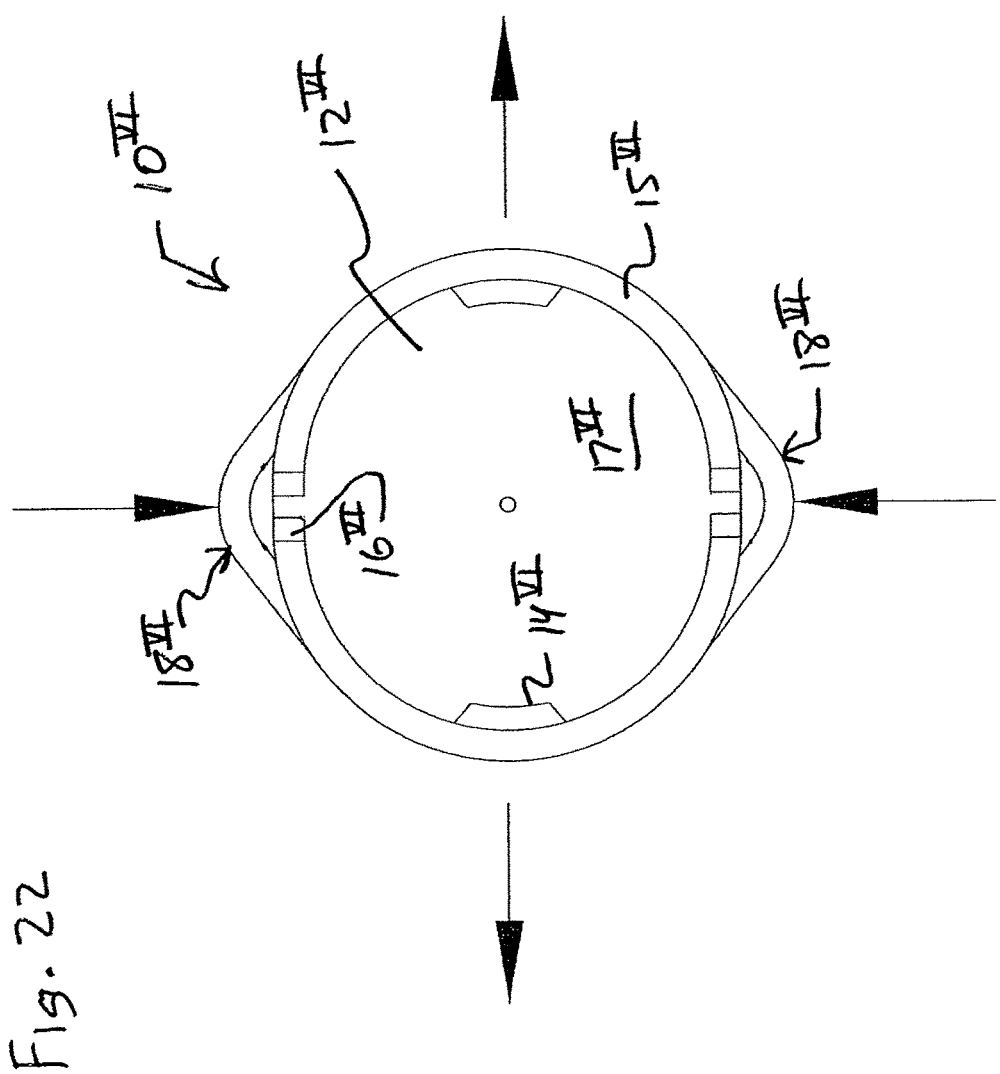

FIGS. 20-22 show another embodiment of a pen needle $10^{VI}$ As with the previous embodiment, the proximal end of the needle tip $10^{VI}$ includes a needle N while the distal end $15^{VI}$ is open and includes an interior space or opening $17^{VI}$ which is sized to allow the needle tip $10^{VI}$ to be mounted onto the threaded proximal end of the pen needle injection device. The pen needle $10^{VI}$ also includes a proximal hub $11^{VI}$, a wall $12^{VI}$, a generally cylindrical sidewall $13^{VI}$, thread sections $14^{VI}$ and plural, and preferably two generally equally spaced (circumferentially or angularly) sidewall slots $16^{VI}$. Each thread section $14^{VI}$ is arranged generally perpendicular to each sidewall slot $16^{VI}$. In embodiments, the slots $16^{VI}$ each extend all the way from the distal end $15^{VI}$ to the distal end of the wall $12^{VI}$ (see FIG. 20). The slots $16^{VI}$ allow the sidewall $13^{VI}$ to deflect outwardly (see FIG. 22) when a user forces integrally formed projecting sections $18^{VI}$ towards each other so that the thread sections can disengage from the thread section 2 to thereby allow the pen needle $10^{VI}$ to be slid off without unthreading or rotation. This embodiment can also otherwise utilize features similar to that shown in FIG. 1 such as features 3, 4 and 5.

FIGS. 21-22 show the generally cylindrical sidewall $13^{VI}$ being integrally formed with sections $18^{VI}$. As is apparent, the section(s) $18^{VI}$ each include a gripping portion $18^{VI}a$ and connecting sections $18^{VI}b$ and $18^{VI}c$ which connect to sidewall portions $13^{VI}a$ and $13^{VI}a$. FIG. 22 shows what happens when the user applies a compressive force (indicated by arrows) to the sections $18^{VI}$ of the needle $10^{VI}$. As is apparent, this causes the sidewalls $13^{VI}$ to enlarge or expand radially and circumferentially (which is facilitated by the slots $16^{VI}$) which results in the slots $16^{VI}$ expanding or becoming wider and threaded sections $14^{VI}$ becoming disengaged from the section 2 of the injection device 1. The sidewall radial expansion shown in FIG. 22 is uneven, however, with the distal end $15^{VI}$ expanding most and with little to no expansion occurring adjacent the wall $12^{VI}$. As a result, each slot $16^{VI}$ assumes a wedge shaped space in FIG. 22 expanding towards the distal end $15^{VI}$.

Figure 23:
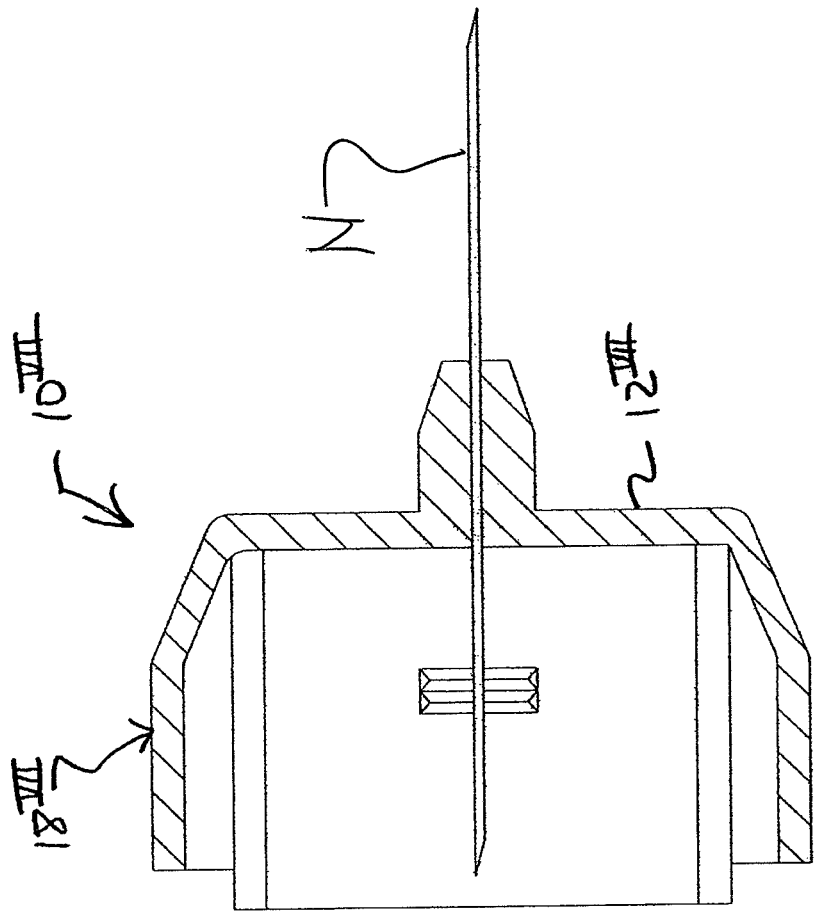
FIGS. 23 and 24 show an eight non-limiting embodiment of a pen needle or tip assembly in according to the invention.
Figure 24:
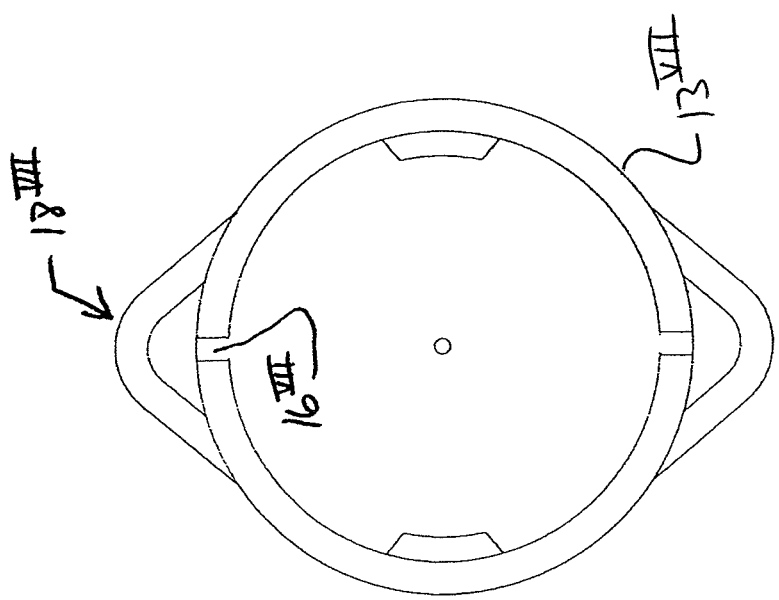

FIGS. 23-24 show another embodiment of a pen needle $10^{VII}$ As with the previous embodiment, the proximal end of the needle tip $10^{VII}$ includes a needle N while the distal end is open and includes an interior space or opening which is sized to allow the needle tip $10^{VII}$ to be mounted onto the threaded proximal end of the injection device. The pen needle $10^{VII}$ also includes a proximal hub, a wall $12^{VII}$, a generally cylindrical sidewall $13^{VII}$, thread sections and plural, and preferably two generally equally spaced (circumferentially or angularly) sidewall slots $16^{VII}$. In embodiments, the slots $16^{VII}$ are relatively narrow and extend all the way from the distal end to the distal end of the wall. The slots $16^{VII}$ allow the sidewall $13^{VII}$ to deflect outwardly (like the previous embodiment) when a user forces integrally formed projecting sections $18^{VII}$ towards each other so that the thread sections can disengage from the thread section 2 to thereby allow the pen needle $10^{VII}$ to be slid off without unthreading or rotation. Unlike the previous embodiment, however, the sections $18^{VII}$ have closed tapered proximal ends instead of being open (compare sections $18^{VI}$ and $18^{VII}$ in FIGS. 20 and 23). This embodiment can also otherwise utilize features similar to that shown in FIG. 1 such as features 3, 4 and 5.

Figure 25:
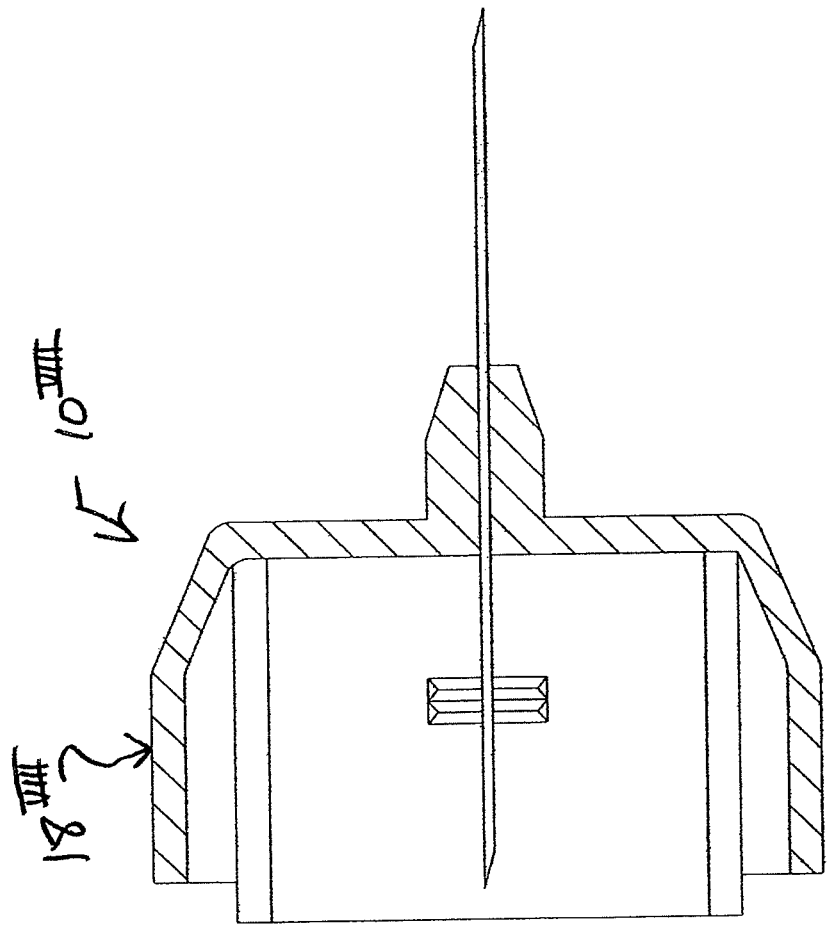
FIGS. 25 and 26 show a ninth non-limiting embodiment of a pen needle or tip assembly in according to the invention.
Figure 26:
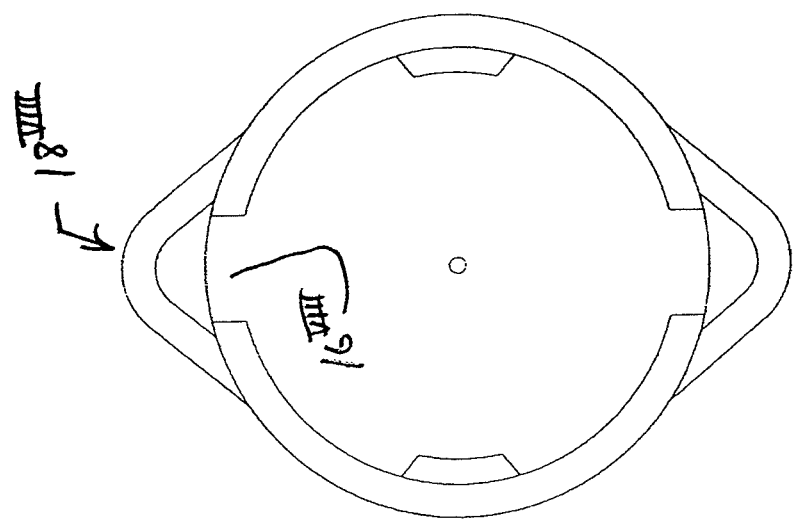

FIGS. 25-26 show another embodiment of a pen needle $10^{VIII}$ As with the previous embodiment, the proximal end of the needle tip $10^{VIII}$ includes a needle N while the distal end is open and includes an interior space or opening which is sized to allow the needle tip $10^{VIII}$ to be mounted onto the threaded proximal end of the injection device. The pen needle $10^{VIII}$ also includes a proximal hub, a wall, a generally cylindrical sidewall, thread sections and plural, and preferably two generally equally spaced (circumferentially or angularly) sidewall slots $16^{VIII}$. In embodiments, the slots $16^{VIII}$ are relatively wide and extend all the way from the distal end to the distal end of the wall. The width of the slots $16^{VIII}$ are configured to allow for a pre-determined compression force requirement. For example, a wider width (whose width can be determined empirically) can be used when users (e.g., very old, very young, or frail users) have less ability to exert a compressive force sufficient to disengage the threaded sections from the threaded proximal end of the injection device. The slots $16^{VIII}$ allow the sidewall to deflect outwardly when a user forces integrally formed projecting sections $18^{VIII}$ towards each other so that the thread sections can disengage from the thread section to thereby allow the pen needle $10^{VIII}$ to be slid off without unthreading or rotation. Like the previous embodiment, the sections $18^{VIII}$ have closed tapered proximal ends. This embodiment can also otherwise utilize features similar to that shown in FIG. 1 such as features 3, 4 and 5.

Figure 27:
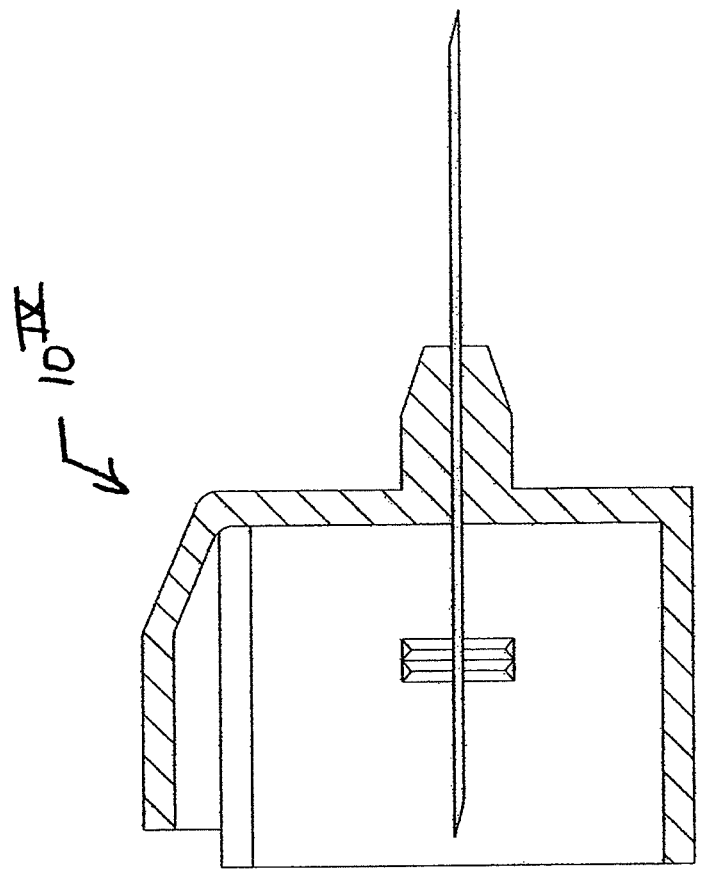
FIGS. 27 and 28 show a tenth non-limiting embodiment of a pen needle or tip assembly in according to the invention.
Figure 28:
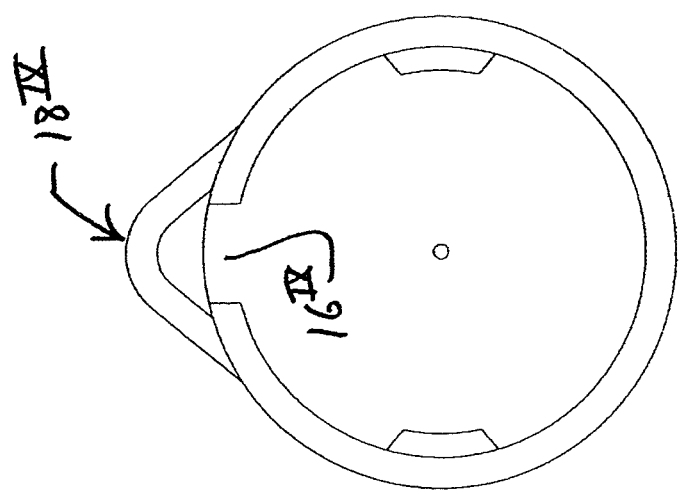

FIGS. 27-28 show another embodiment of a pen needle $10^{IX}$ As with the previous embodiment, the proximal end of the needle tip $10^{IX}$ includes a needle N while the distal end is open and includes an interior space or opening which is sized to allow the needle tip $10^{IX}$ to be mounted onto the threaded proximal end of the injection device. The pen needle $10^{IX}$ also includes a proximal hub, a wall, a generally cylindrical sidewall, thread sections and only one sidewall slot $16^{IX}$. In embodiments, the slot $16^{IX}$ is relatively wide and extend all the way from the distal end to the distal end of the wall. The width of the slot $16^{IX}$ can be configured to allow for a pre-determined compression force requirement. As in previous embodiments, the slot $16^{IX}$ allows the sidewall to deflect outwardly when a user forces the single integrally formed projecting section $18^{IX}$ towards a center axis so that the thread sections can disengage from the thread section to thereby allow the pen needle $10^{IX}$ to be slid off without unthreading or rotation. Like the previous embodiment, the single section $18^{IX}$ has closed tapered proximal end. This embodiment can also otherwise utilize features similar to that shown in FIG. 1 such as features 3, 4 and 5.

Figure 29:
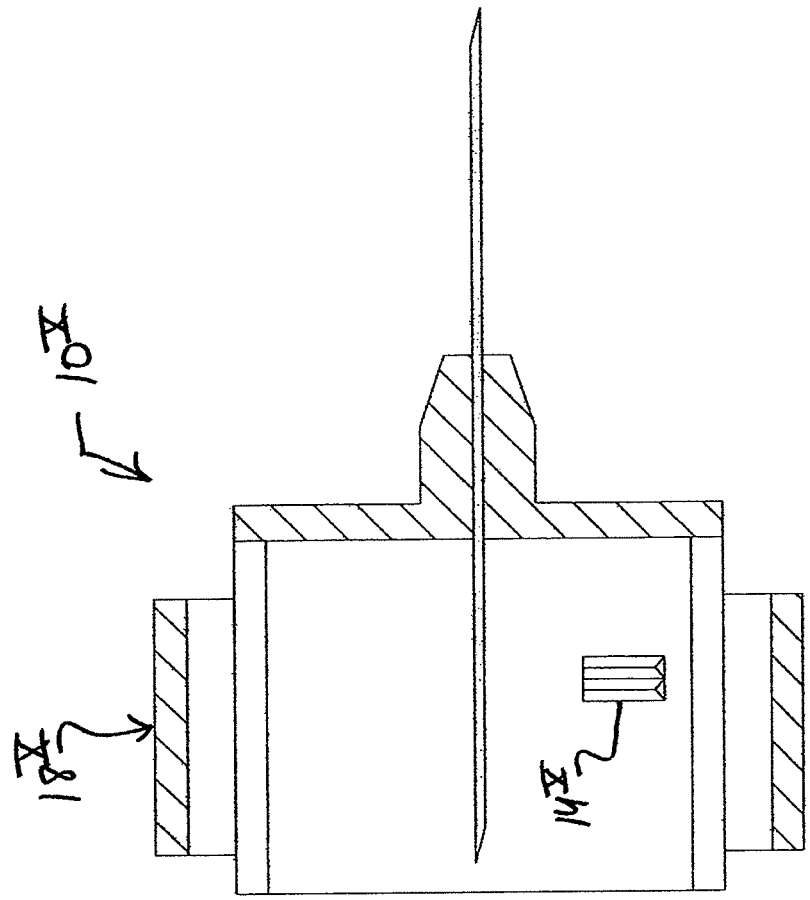
FIGS. 29 and 30 show another non-limiting embodiment of a pen needle or tip assembly in according to the invention.
Figure 30:
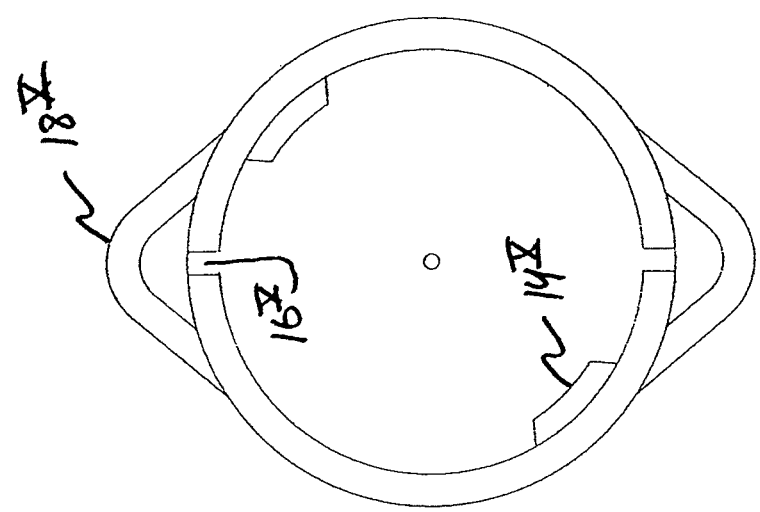

FIGS. 29-30 show another embodiment of a pen needle $10^{X}$ As with the previous embodiment, the proximal end of the needle tip $10^{X}$ includes a needle while the distal end is open and includes an interior space or opening which is sized to allow the needle tip $10^{X}$ to be mounted onto the threaded proximal end of the injection device. The pen needle $10^{X}$ also includes a proximal hub, a wall, a generally cylindrical sidewall, two oppositely arranged thread sections $14^{X}$ and two generally oppositely arranged sidewall slots $16^{X}$. In embodiments, the slots $16^{X}$ are relatively narrow and extend all the way from the distal end to the distal end of the wall. The slots $16^{X}$ allow the sidewall to deflect outwardly when a user forces integrally formed projecting sections $18^{X}$ towards each other so that the thread sections $14^{X}$ (which angularly offset from the position shown in FIG. 21) can disengage from the thread section to thereby allow the pen needle $10^{X}$ to be slid off without unthreading or rotation. In embodiments, the thread sections $14^{X}$ are arranged at about 45 degrees relative to an axis passing through both slots $16^{X}$ and the slots $16^{X}$ are generally circumferentially aligned with the sections $18^{X}$. This embodiment can also otherwise utilize features similar to that shown in FIG. 1 such as features 3, 4 and 5.

Figure 31:
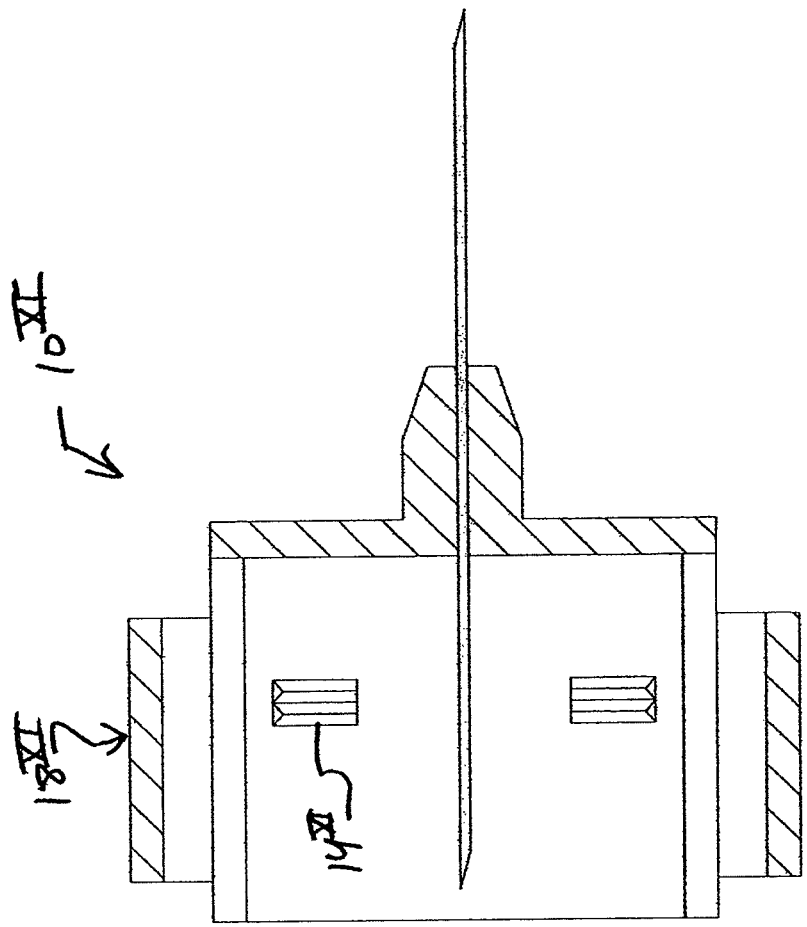
FIGS. 31 and 32 show another non-limiting embodiment of a pen needle or tip assembly in according to the invention.
Figure 32:
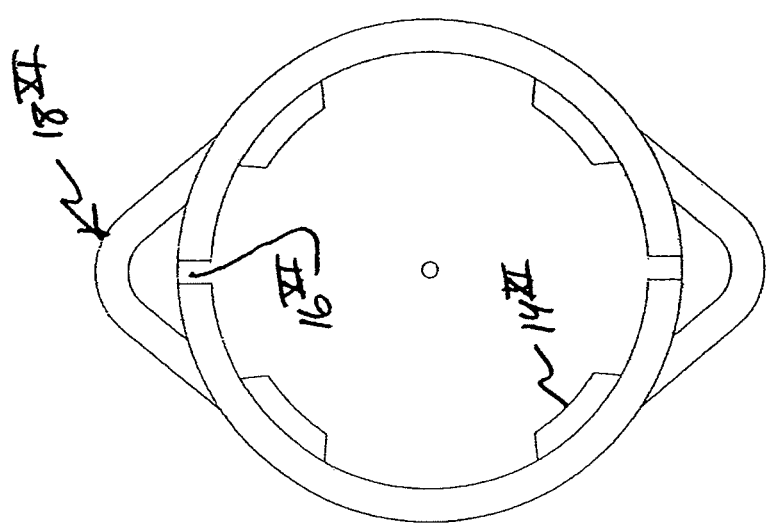

FIGS. 31-32 show another embodiment of a pen needle $10^{XI}$ As with the previous embodiment, the proximal end of the needle tip $10^{XI}$ includes a needle while the distal end is open and includes an interior space or opening which is sized to allow the needle tip $10^{XI}$ to be mounted onto the threaded proximal end of the injection device. The pen needle $10^{XI}$ also includes a proximal hub, a wall, a generally cylindrical sidewall, two oppositely arranged thread sections $14^{XI}$ and four generally oppositely arranged sidewall slots $16^{XI}$. In embodiments, the slots $16^{XI}$ are relatively narrow and extend all the way from the distal end to the distal end of the wall. The slots $16^{XI}$ allow the sidewall to deflect outwardly when a user forces integrally formed projecting sections $18^{XI}$ towards each other so that the thread sections $14^{XI}$ can disengage from the thread section to thereby allow the pen needle $10^{XI}$ to be slid off without unthreading or rotation. In embodiments, the thread sections $14^{XI}$ are arranged at about 45 degrees relative to an axis passing through both slots $16^{XI}$ and the slots $16^{XI}$ are generally circumferentially aligned with the sections $18^{XI}$. This embodiment can also otherwise utilize features similar to that shown in FIG. 1 such as features 3, 4 and 5.

Figure 33:
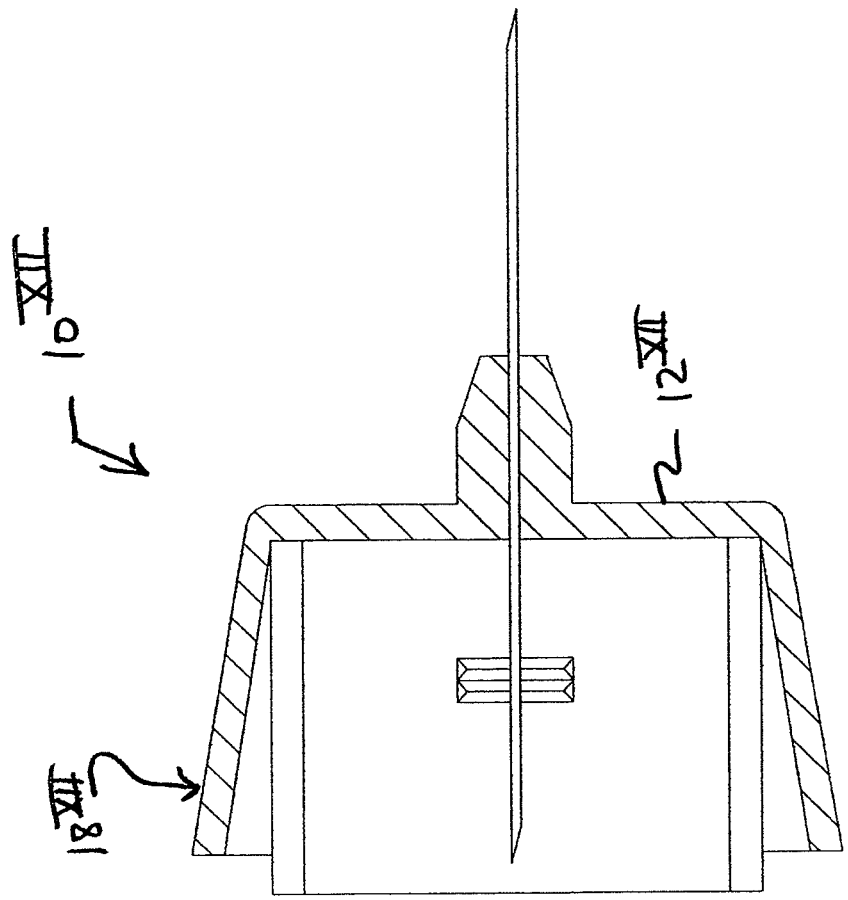
FIGS. 33 and 34 show another non-limiting embodiment of a pen needle or tip assembly in according to the invention.
Figure 34:
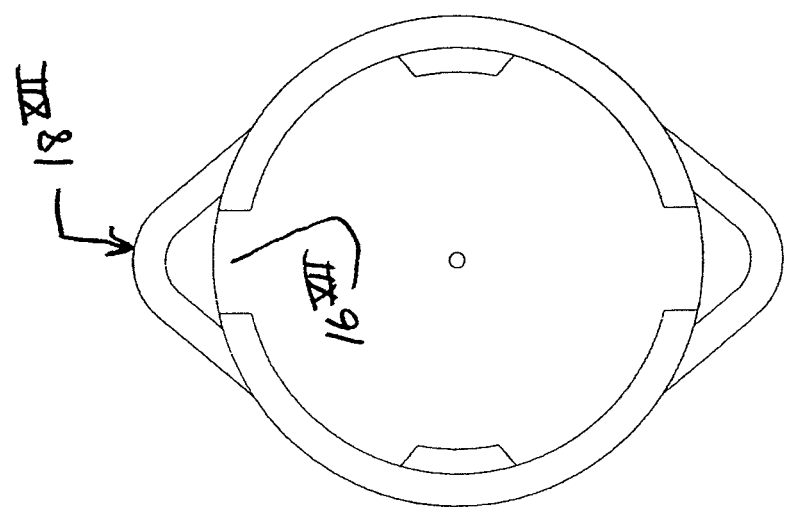

FIGS. 33-34 show another embodiment of a pen needle $10^{XII}$ As with the previous embodiment, the proximal end of the needle tip $10^{XII}$ includes a needle while the distal end is open and includes an interior space or opening which is sized to allow the needle tip $10^{XII}$ to be mounted onto the threaded proximal end of the injection device. The pen needle $10^{XII}$ also includes a proximal hub, a wall $12^{XII}$, a generally cylindrical sidewall, thread sections and plural, and preferably two generally equally spaced (circumferentially or angularly) sidewall slots $16^{XII}$. In embodiments, the slots $16^{XII}$ are relatively wide and extend all the way from the distal end to the distal end of the wall. The width of the slots $16^{XII}$ can be configured to allow for a pre-determined compression force requirement. The slots $16^{XII}$ allow the sidewall to deflect outwardly when a user forces integrally formed projecting sections $18^{XII}$ towards each other so that the thread sections can disengage from the thread section to thereby allow the pen needle $10^{XII}$ to be slid off without unthreading or rotation. Unlike the previous embodiments, however, the sections $18^{XII}$ are completely tapered and have closed proximal ends terminating at or extending to the wall $12^{XII}$. This embodiment can also otherwise utilize features similar to that shown in FIG. 1 such as features 3, 4 and 5.

Figure 35:
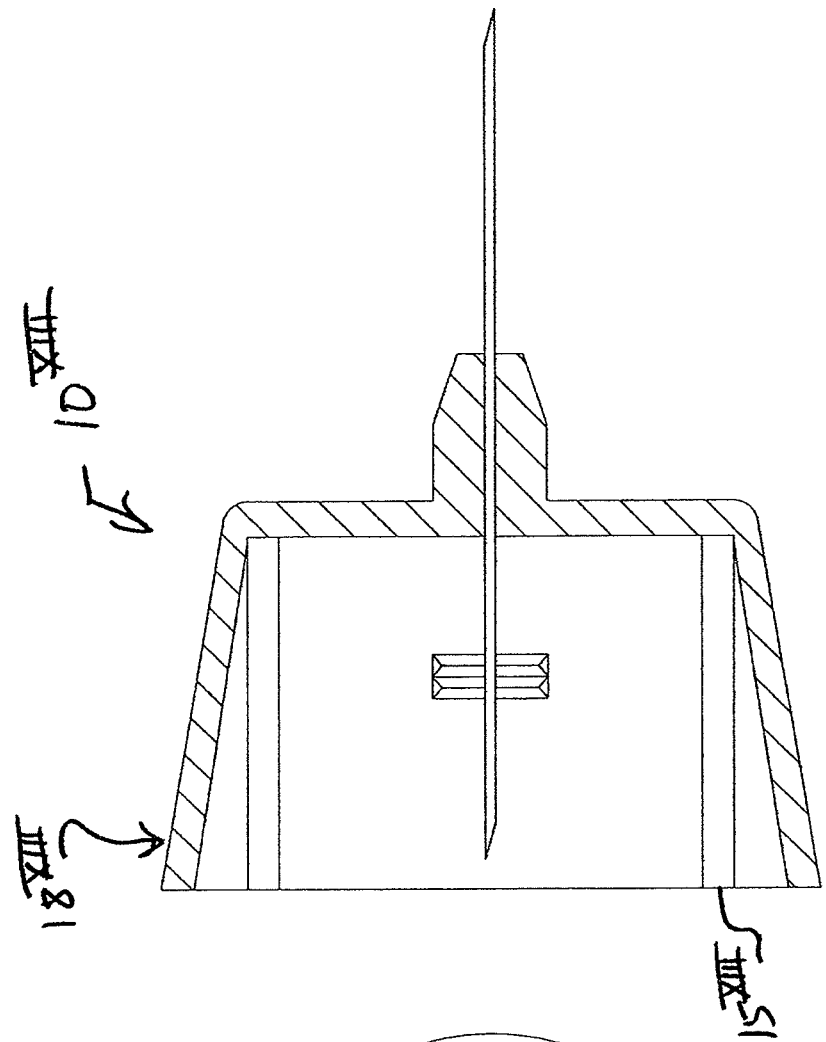
FIGS. 35 and 36 show another non-limiting embodiment of a pen needle or tip assembly in according to the invention.
Figure 36:
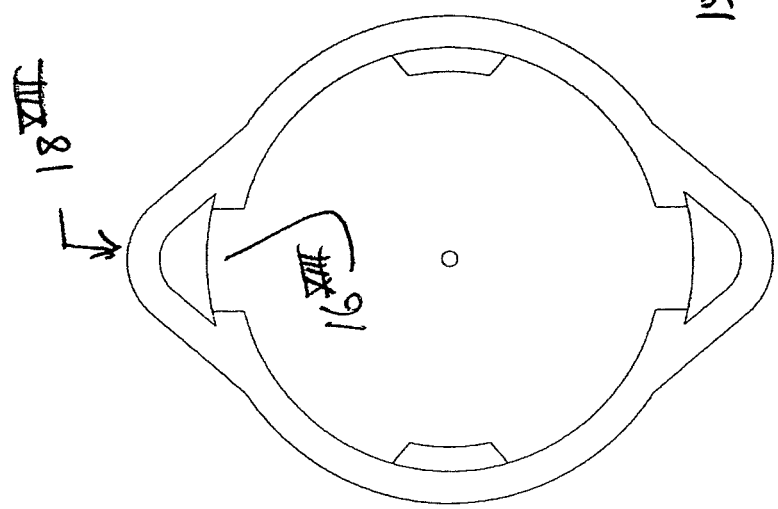

FIGS. 35-36 show another embodiment of a pen needle $10^{XIII}$ As with the previous embodiment, the proximal end of the needle tip $10^{XIII}$ includes a needle while the distal end is open and includes an interior space or opening which is sized to allow the needle tip $10^{XIII}$ to be mounted onto the threaded proximal end of the injection device. The pen needle $10^{XIII}$ also includes a proximal hub, a wall, a generally cylindrical sidewall, thread sections and plural, and preferably two generally equally spaced (circumferentially or angularly) sidewall slots $16^{XIII}$. In embodiments, the slots $10^{XIII}$ are relatively wide, have the configuration shown in FIG. 36, and extend all the way from the distal end $15^{XIII}$ to the distal end of the wall. The width of the slots $16^{XIII}$ can be configured to allow for a pre-determined compression force requirement. The slots $16^{XIII}$ allow the sidewall to deflect outwardly when a user forces integrally formed projecting sections $18^{XIII}$ towards each other so that the thread sections can disengage from the thread section to thereby allow the pen needle $10^{XIII}$ to be slid off without unthreading or rotation. Like the previous embodiments, the sections $18^{XIII}$ are completely tapered and have closed proximal ends terminating at or extending to the wall. This embodiment can also otherwise utilize features similar to that shown in FIG. 1 such as features 3, 4 and 5.

Figure 37:
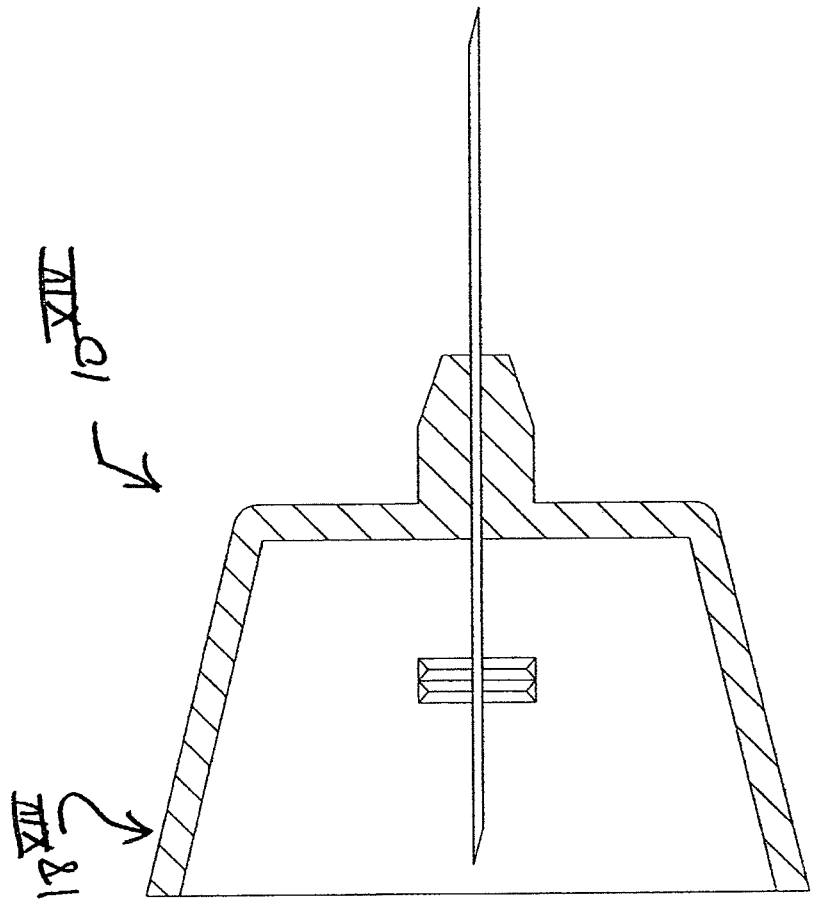
FIGS. 37 and 38 show another non-limiting embodiment of a pen needle or tip assembly in according to the invention.
Figure 38:
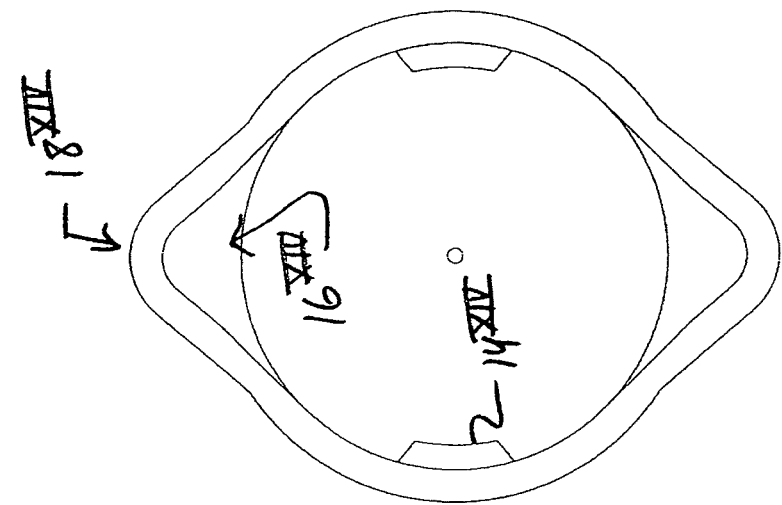
Figure 39:
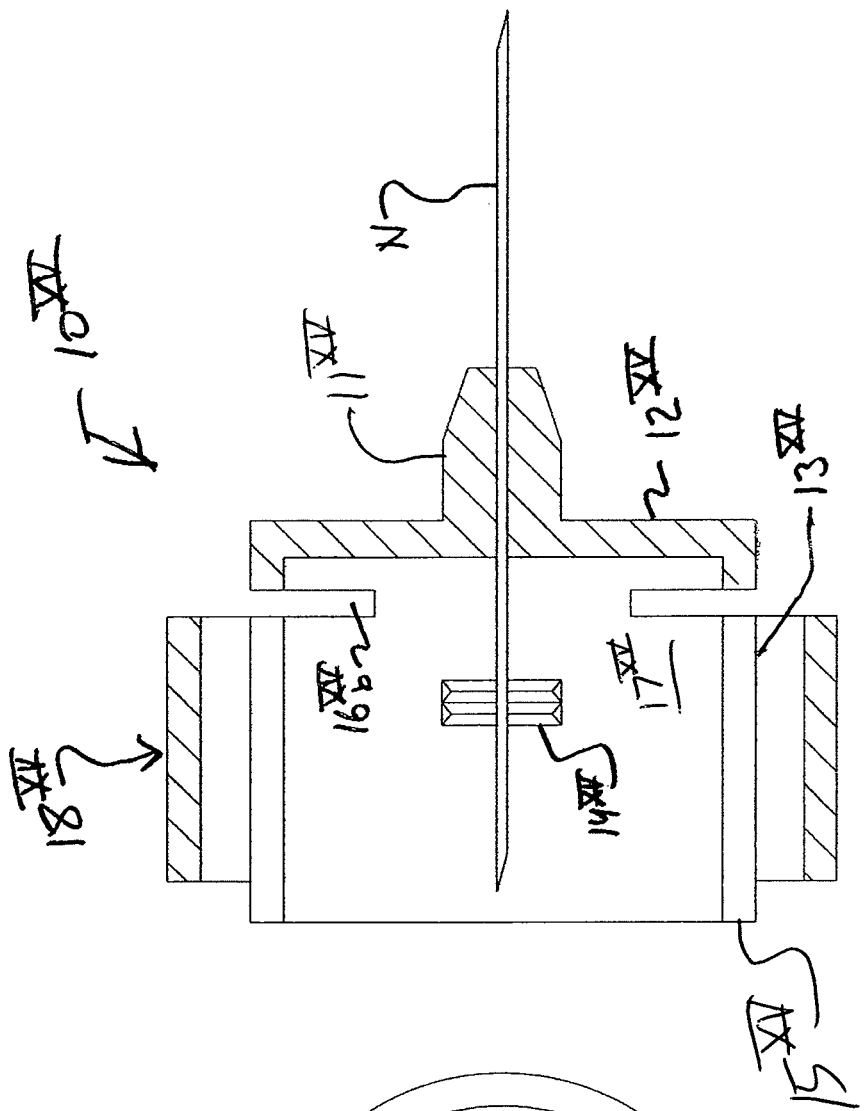
Figure 40:
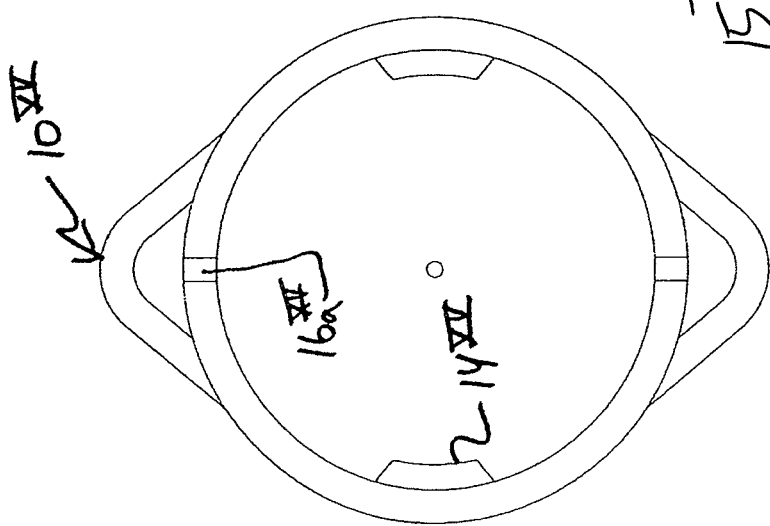
Figure 43:
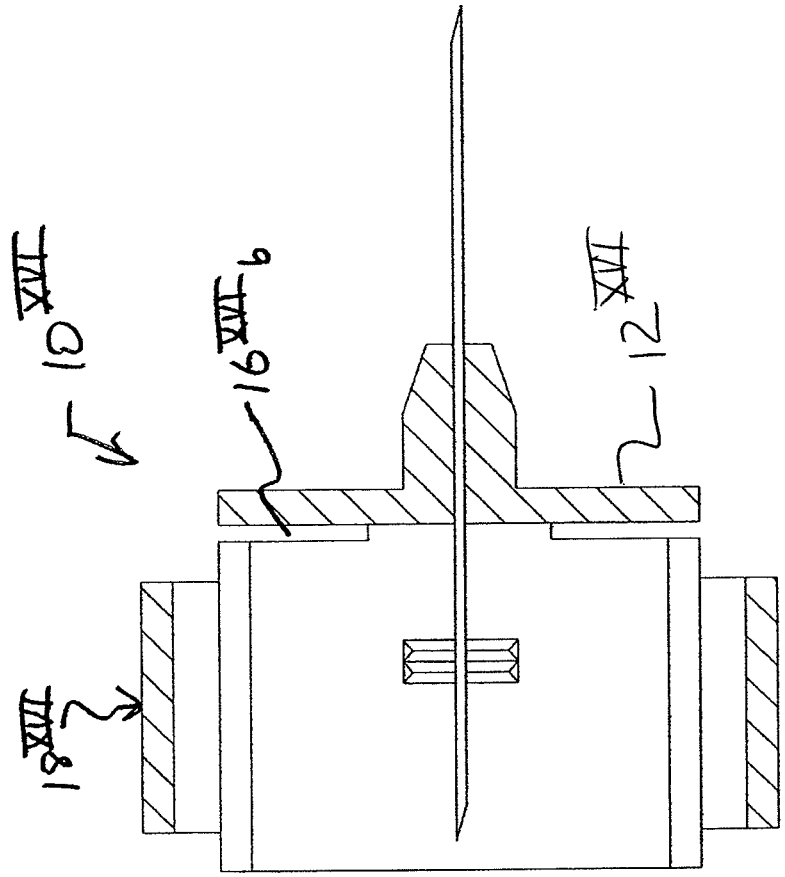
FIGS. 43-46 show another non-limiting embodiment of a pen needle or tip assembly in according to the invention.
Figure 44:
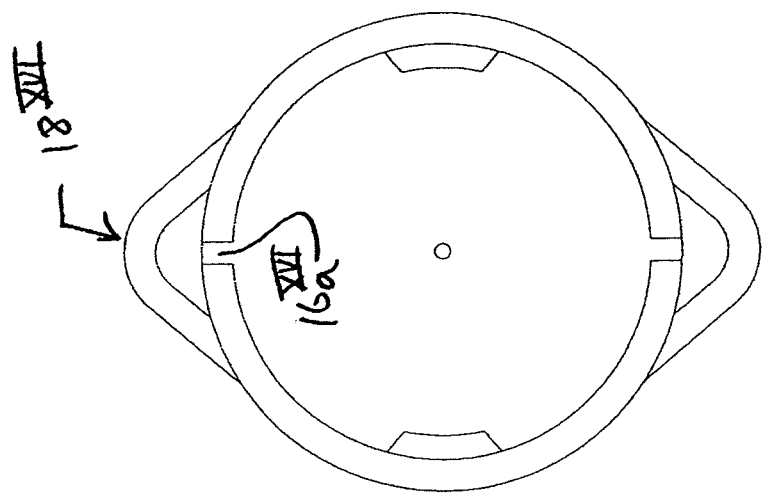
Figures 45, 46:
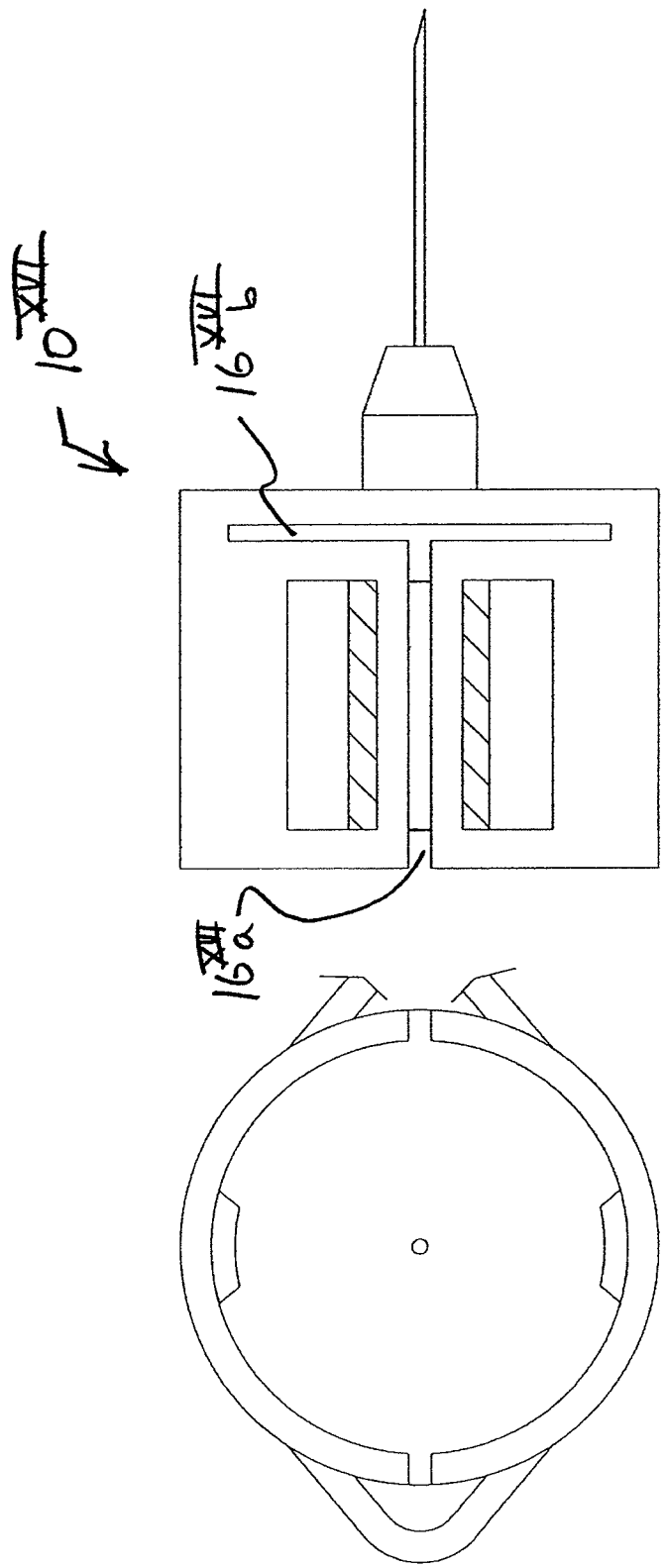

FIGS. 37-38 show another embodiment of a pen needle $10^{XIV}$. As with the previous embodiment, the proximal end of the needle tip $10^{XIV}$ includes a needle while the distal end is open and includes an interior space or opening which is sized to allow the needle tip $10^{XIV}$ to be mounted onto the threaded proximal end of the injection device. The pen needle $10^{XIV}$ also includes a proximal hub, a wall, a generally cylindrical sidewall, and thread sections $14^{XIV}$. Unlike previous embodiments, the two generally equally spaced (circumferentially or angularly) sidewall slots $16^{XIV}$ are made an integral or defining part of the gripping sections $18^{XIV}$. In embodiments, the slots $16^{XIV}$ are essentially a tapered space defined by the sections $18^{XIV}$ and are relatively wide so as to have the configuration shown in FIGS. 37 and 28, and extend all the way from the distal end to the distal end of the wall. The width of the slots $16^{XIV}$ are essentially maximized in relation to the sections $18^{XIV}$ and are configured to allow for a lower compression force requirement. The slots or spaces $16^{XIV}$ allow the sidewall to deflect outwardly when a user forces integrally formed projecting sections $18^{XIV}$ towards each other so that the thread sections can disengage from the thread section to thereby allow the pen needle $10^{XIV}$ to be slid off without unthreading or rotation. Like the previous embodiments, the sections $18^{XIV}$ are completely tapered and have closed proximal ends terminating at or extending to the wall. This embodiment can also otherwise utilize features similar to that shown in FIG. 1 such as features 3, 4 and 5.

FIGS. 39-42 show another embodiment of a pen needle $10^{XV}$ As with the previous embodiment, the proximal end of the needle tip $10^{XV}$ includes a needle N while the distal end $15^{XV}$ is open and includes an interior space or opening $17^{XV}$ which is sized to allow the needle tip $10^{XV}$ to be mounted onto the threaded proximal end of the pen needle injection device. The pen needle $10^{XV}$ also includes a proximal hub $11^{XV}$, a wall $12^{XV}$, a generally cylindrical sidewall $13^{XV}$, thread sections $14^{XV}$ and plural, and preferably two generally equally spaced (circumferentially or angularly) sidewall slots $16^{XV}a$. Each thread section $14^{XV}$ is arranged generally perpendicular to each sidewall slot $16^{XV}a$. In embodiments, the slots $16^{XV}a$ do not extend all the way from the distal end $15^{XV}$ to the distal end of the wall $12^{XV}$ and instead extend to partial circumferential slots $16^{XV}b$. The slots $16^{XV}a$ and $16^{XV}b$ allow the sidewall $13^{XV}$ to deflect outwardly more evenly than previous embodiments when a user forces integrally formed projecting sections $18^{XV}$ towards each other so that the thread sections can disengage from the thread section of the injection device to thereby allow the pen needle $10^{XV}$ to be slid off without unthreading or rotation. This embodiment can also otherwise utilize features similar to that shown in FIG. 1 such as features 3, 4 and 5.

FIGS. 43-46 show another embodiment of a pen needle $10^{XVI}$. As with the previous embodiment, the proximal end of the needle tip $10^{XVI}$ includes a needle while the distal end is open and includes an interior space or opening which is sized to allow the needle tip $10^{XVI}$ to be mounted onto the threaded proximal end of the pen needle injection device. The pen needle $10^{XVI}$ also includes a proximal hub, a wall $12^{XVI}$, a generally cylindrical sidewall, thread sections and plural, and preferably two generally equally spaced (circumferentially or angularly) sidewall slots $16^{XVI}a$. Each thread section is arranged generally perpendicular to each sidewall slot $16^{XVI}a$. In embodiments, the slots $16^{XVI}a$ extend nearly all the way from the distal end to the distal end of the wall $12^{XVI}$ and also to the partial circumferential slots $16^{XVI}b$. The slots $16^{XVI}a$ and $16^{XVI}b$ allow the sidewall to deflect outwardly more evenly than previous embodiments not utilizing the circumferential slots when a user forces integrally formed projecting sections $18^{XVI}$ towards each other so that the thread sections can disengage from the thread section of the injection device to thereby allow the pen needle $10^{XVI}$ to be slid off without unthreading or rotation. This embodiment can also otherwise utilize features similar to that shown in FIG. 1 such as features 3, 4 and 5.

Figure 49:
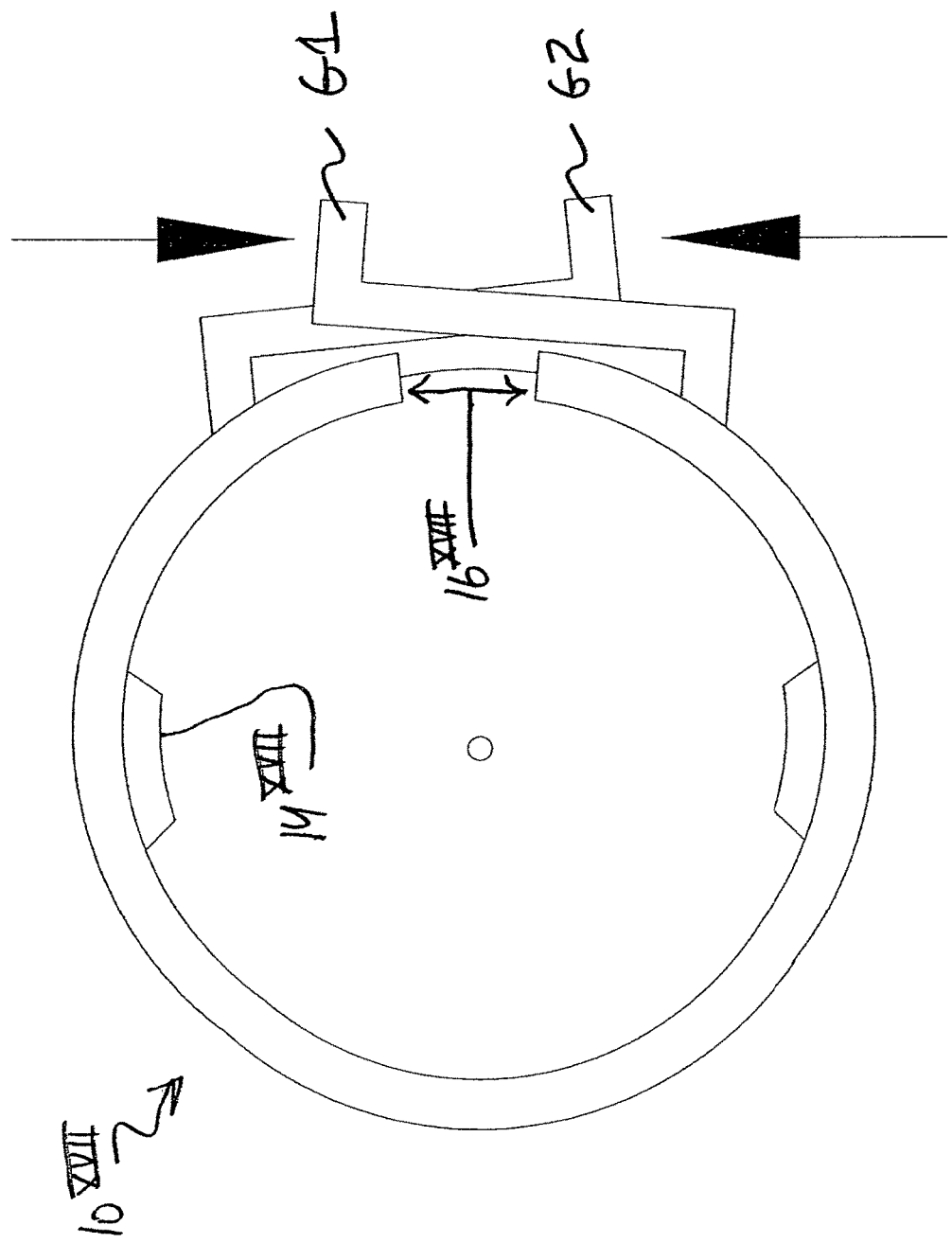

FIGS. 47-49 show another embodiment of a pen needle $10^{XVII}$. As with the previous embodiment, the proximal end of the needle tip $10^{XVII}$ includes a needle while the distal end is open and includes an interior space or opening which is sized to allow the needle tip $10^{XVII}$ to be mounted onto the threaded proximal end of the pen needle injection device. The pen needle $10^{XVII}$ also includes a proximal hub, a wall $12^{XVII}$, a generally cylindrical sidewall $13^{XVII}$, thread sections $14^{XVII}$ and a single sidewall slot $16^{XVII}a$. Each thread section $14^{XVII}$ is arranged generally perpendicular to the sidewall slot $16^{XVII}a$. In embodiments, the slot $16^{XVII}a$ extends nearly all the way from the distal end to the distal end of the wall $12^{XVII}$ and also to the single partial circumferential slot $16^{XVII}b$. The slots $16^{XVII}a$ and $16^{XVII}b$ allow the sidewall $13^{XVII}$ to deflect outwardly more evenly than certain previous embodiments when a user forces integrally formed projecting sections $18^{XVII}$ towards each other so that the thread sections can disengage from the thread section of the injection device to thereby allow the pen needle $10^{XVII}$ to be slid off without unthreading or rotation. To do so, a user moves gripping projections G1 and G2 towards each other (as indicated by arrows) as shown in FIG. 49 so as to cause a widening of the slot $16^{XVII}a$. This embodiment can also otherwise utilize features similar to that shown in FIG. 1 such as features 3, 4 and 5.

Figure 52:
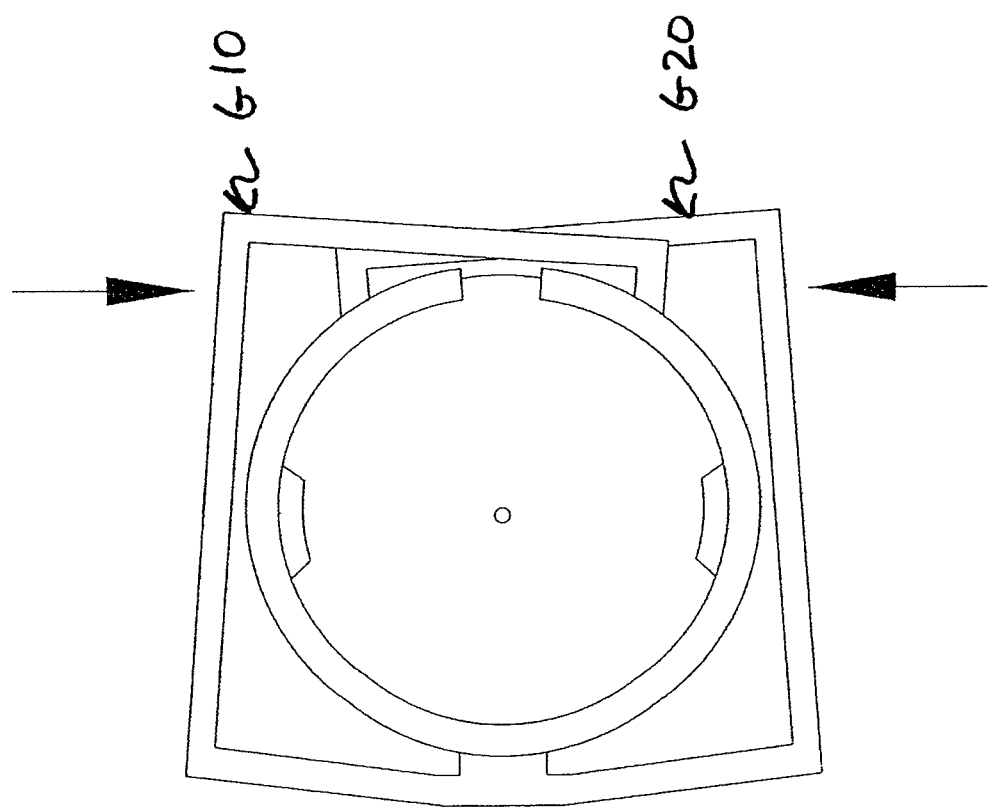

FIGS. 50-52 show another embodiment of a pen needle $10^{XVIII}$. As with the previous embodiment, the proximal end of the needle tip $10^{XVIII}$ includes a needle while the distal end is open and includes an interior space or opening which is sized to allow the needle tip $10^{XVIII}$ to be mounted onto the threaded proximal end of the pen needle injection device. The pen needle $10^{XVIII}$ also includes a proximal hub, a wall $12^{XVIII}$, a generally cylindrical sidewall, thread sections and a single sidewall slot $16^{XVIII}a$. Each thread section is arranged generally perpendicular to the sidewall slot $16^{XVIII}a$. In embodiments, the slot $16^{XVIII}a$ extends nearly all the way from the distal end to the distal end of the wall $12^{XVIII}$ and also to the single partial circumferential slot $16^{XVIII}b$. The slots $16^{XVIII}a$ and $16^{XVIII}b$ allow the sidewall to deflect outwardly more evenly than certain previous embodiments when a user forces integrally formed projecting sections $18^{XVIII}$ towards each other so that the thread sections can disengage from the thread section of the injection device to thereby allow the pen needle $10^{XVIII}$ to be slid off without unthreading or rotation. To do so, a user moves gripping projections G10 and G20 towards each other (as indicated by arrows) as shown in FIG. 52 so as to cause a widening of the slot $16^{XVIII}a$. This embodiment can also otherwise utilize features similar to that shown in FIG. 1 such as features 3, 4 and 5.

Figure 53:
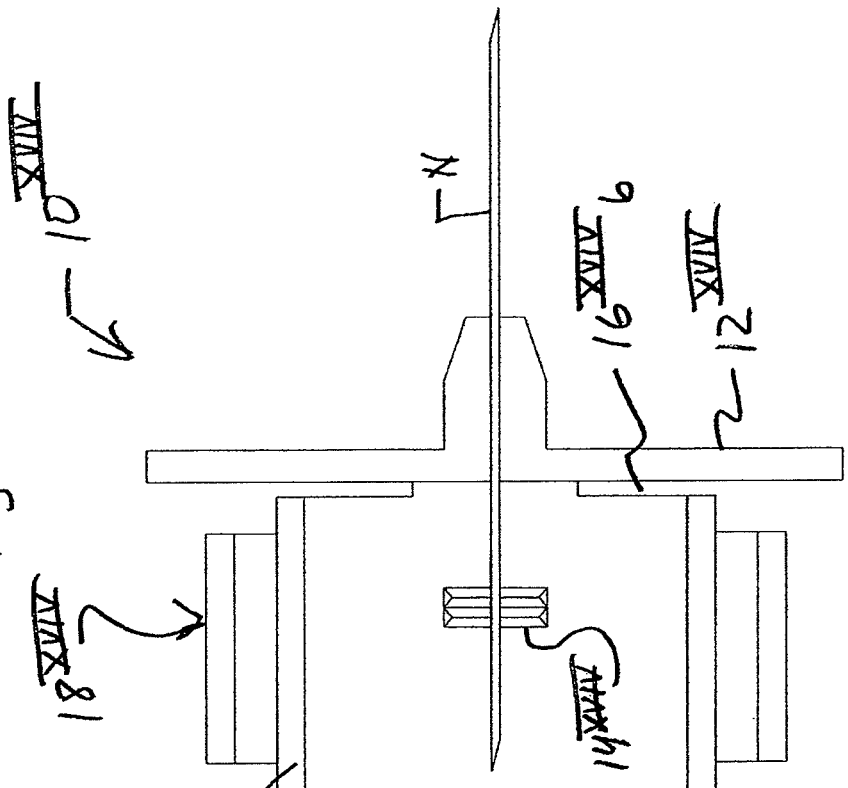
FIGS. 53 and 54 show another non-limiting embodiment of a pen needle or tip assembly in according to the invention.
Figure 54:
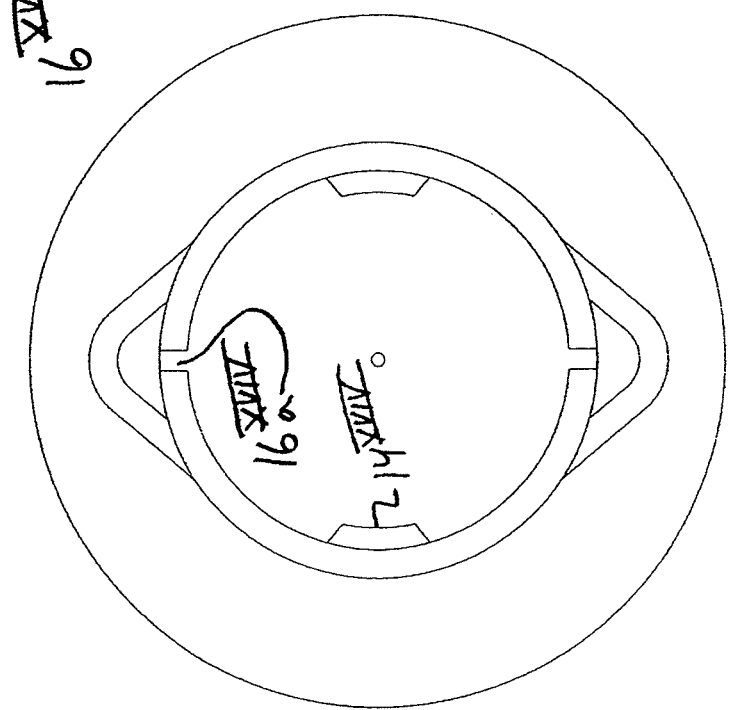

FIGS. 53-54 show another embodiment of a pen needle $10^{XVIV}$. As with the previous embodiment, the proximal end of the needle tip $10^{XVIV}$ includes a needle while the distal end is open and includes an interior space or opening which is sized to allow the needle tip $10^{XVIV}$ to be mounted onto the threaded proximal end of the pen needle injection device. The pen needle $10^{XVIV}$ also includes a proximal hub, a wall $12^{XVIV}$, which in this embodiment has an enlarged diameter to protect the user from the needle N when gripping the sections $18^{XVIV}$. A generally cylindrical sidewall, thread sections $14^{XVIV}$ and sidewall slots $16^{XVIV}a$ are also utilized. Each thread section $14^{XVIV}$ is arranged generally perpendicular to the sidewall slots $16^{XVIV}a$. In embodiments, the slots $16^{XVIV}a$ extend nearly all the way from the distal end to the distal end of the wall $12^{XVIV}$ and also to the partial circumferential slots $16^{XVIV}b$. The slots $16^{XVIV}a$ and $16^{XVIV}b$ allow the sidewall to deflect outwardly more evenly than certain previous embodiments when a user forces integrally formed projecting sections $18^{XVIV}$ towards each other so that the thread sections can disengage from the thread section of the injection device to thereby allow the pen needle $10^{XVIV}$ to be slid off without unthreading or rotation. To do so, a user moves projections or sections $18^{XVIV}$ towards each other so as to cause a widening of the slots $16^{XVIV}a$. This embodiment can also otherwise utilize features similar to that shown in FIG. 1 such as features 3, 4 and 5.

Figure 55:
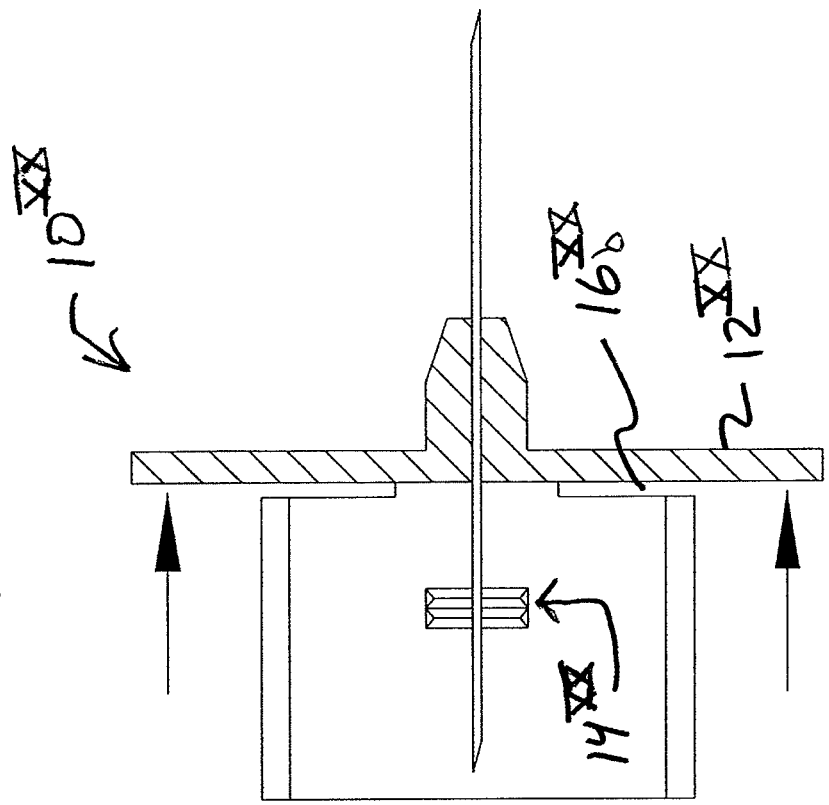
FIGS. 55 and 56 show another non-limiting embodiment of a pen needle or tip assembly in according to the invention.
Figure 56:
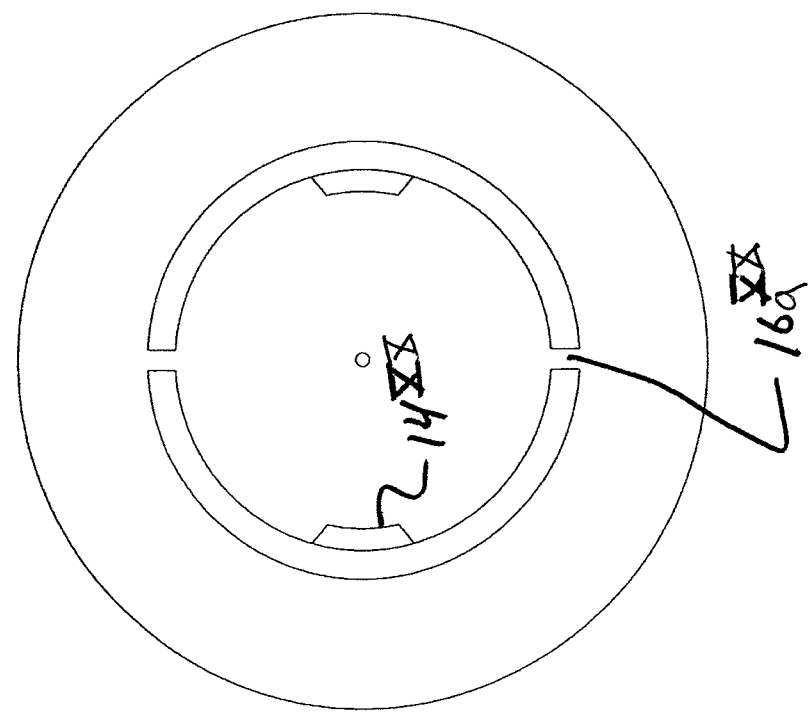

FIGS. 55-56 show another embodiment of a pen needle $10^{XX}$. As with the previous embodiment, the proximal end of the needle tip $10^{XX}$ includes a needle while the distal end is open and includes an interior space or opening which is sized to allow the needle tip $10^{XX}$ to be mounted onto the threaded proximal end of the pen needle injection device. The pen needle $10^{XX}$ also includes a proximal hub, a wall $12^{XX}$, which in this embodiment has an enlarged diameter to protect the user from the needle N when gripping the generally cylindrical sidewall. Thread sections $14^{XX}$ and sidewall slots $16^{XX}a$ are also utilized. Each thread section $14^{XX}$ is arranged generally perpendicular to the sidewall slots $16^{XX}a$. In embodiments, the slots $16^{XX}a$ extend nearly all the way from the distal end to the distal end of the wall $12^{XX}$ and also to the partial circumferential slots $16^{XX}b$. The slots $16^{XX}a$ and $16^{XX}b$ allow the sidewall to deflect outwardly more evenly than certain previous embodiments when a user axially pulls off pen needle $10^{XX}$ without unthreading or rotation. Unlike previous embodiments, a user need not move projections or sections (such as sections $18^{XVIV}$ of the previous embodiment) towards each other so as to cause a widening of the slots $16^{XX}a$. Instead, the pulling off motion (see arrows in FIG. 55) causes expansion of the slots $16^{XX}a$. This embodiment can also otherwise utilize features similar to that shown in FIG. 1 such as features 3, 4 and 5.

Figure 57:
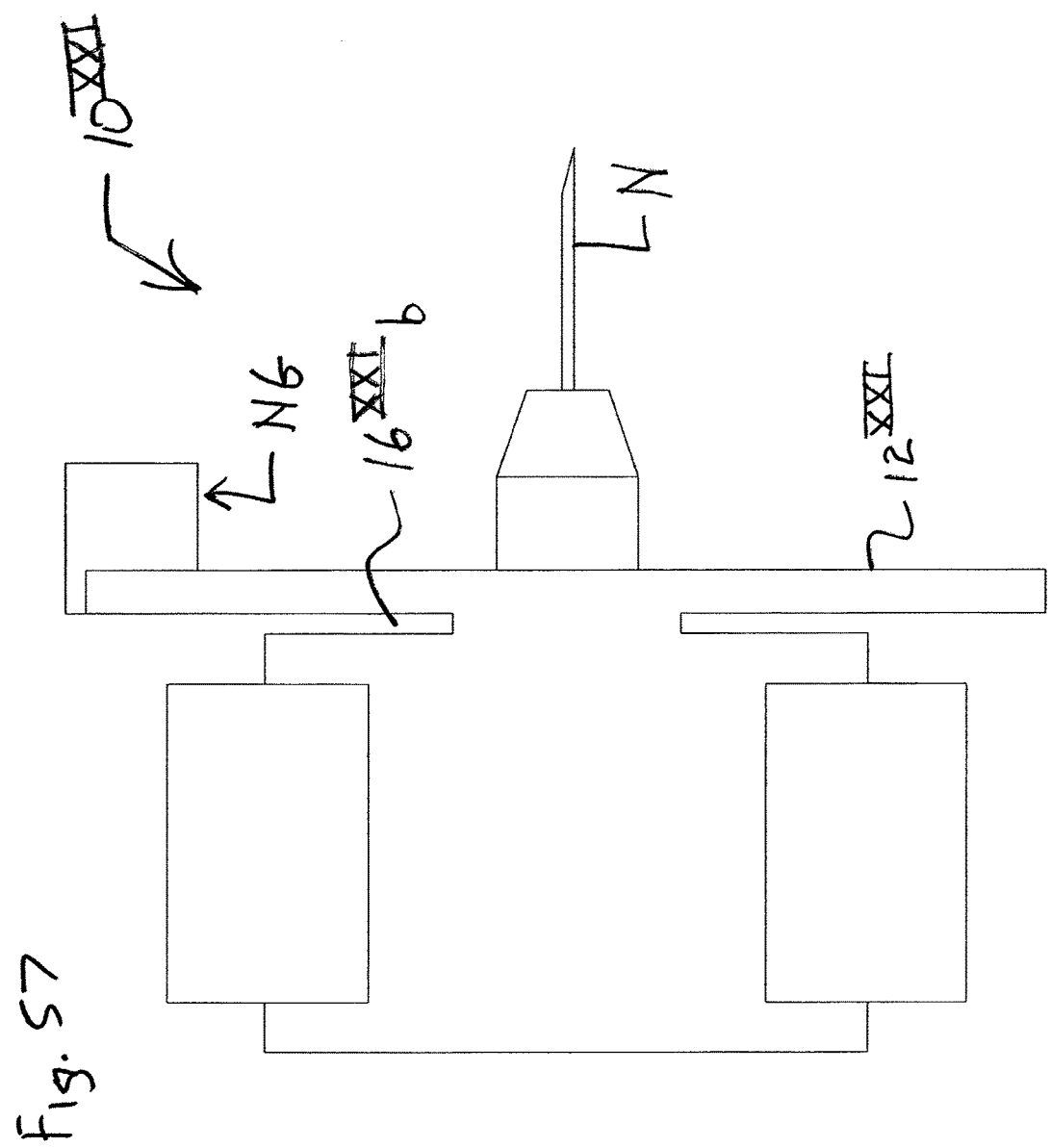
FIGS. 57-59 show another non-limiting embodiment of a pen needle or tip assembly in according to the invention.
Figure 58:
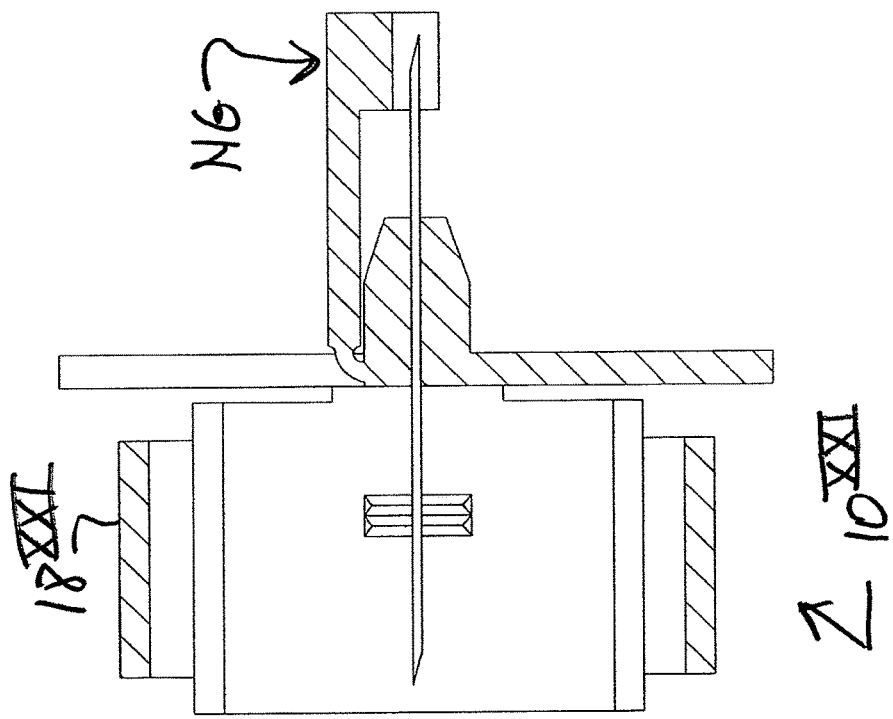
Figure 59:
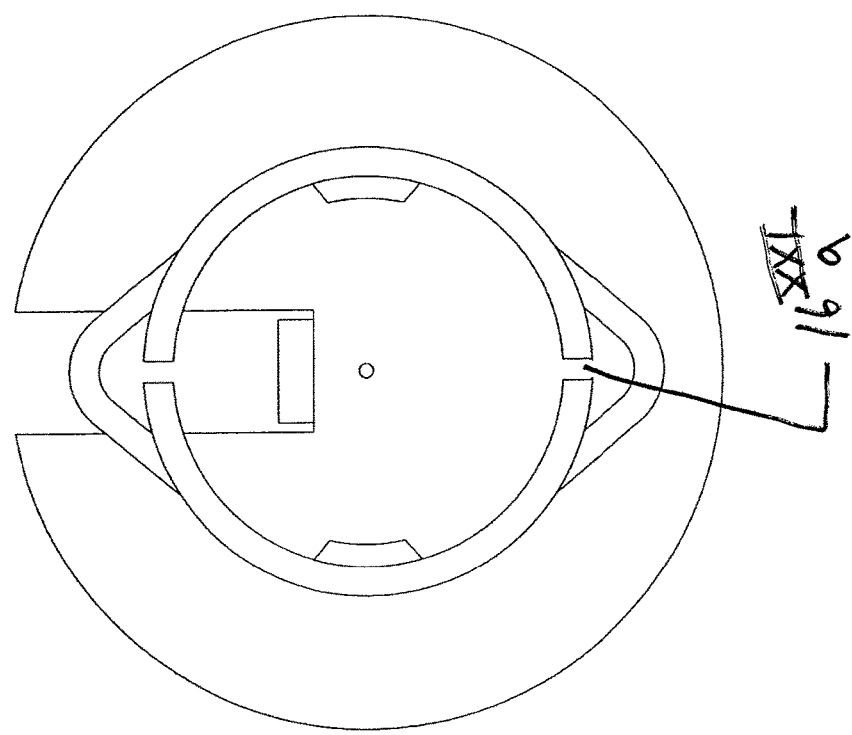

FIGS. 57-59 show another embodiment of a pen needle $10^{XXI}$. As with the previous embodiment, the proximal end of the needle tip $10^{XXI}$ includes a needle while the distal end is open and includes an interior space or opening which is sized to allow the needle tip $10^{XXI}$ to be mounted onto the threaded proximal end of the pen needle injection device. The pen needle $10^{XXI}$ also includes a proximal hub, a wall $12^{XXI}$, which in this embodiment has an enlarged diameter to protect the user from the needle N when gripping the generally cylindrical sidewall. Thread sections and sidewall slots $16^{XXI}a$ are also utilized. Each thread section is arranged generally perpendicular to the sidewall slots $16^{XXI}a$. In embodiments, the slots $16^{XXI}a$ extend nearly all the way from the distal end to the distal end of the wall $12^{XXI}$ and also to the partial circumferential slots $16^{XXI}b$. The slots $16^{XXI}a$ and $16^{XXI}b$ allow the sidewall to deflect outwardly more evenly than certain previous embodiments when a user moves sections $18^{XXI}$ towards each other and axially pulls off pen needle $10^{XXI}$ without unthreading or rotation. Unlike previous embodiments, a user can also move a needle guard NG from an original position shown in FIG. 57 to a position covering the needle N as shown in FIG. 58. This can preferably occur before the pen needle $10^{XXI}$ is pulled off. This embodiment can also otherwise utilize features similar to that shown in FIG. 1 such as features 3, 4 and 5.

FIGS. 60-61 show another embodiment of a pen needle $10^{XXII}$. This embodiment is similar to the previous embodiment and additionally includes a locking system LS for locking the needle guard NG' in the needle covering position shown in FIG. 60. In embodiments, the locking system LS can utilize a non-releasable locking engagement between a locking projection and a locking recess as shown in FIG. 61.

Figure 62:
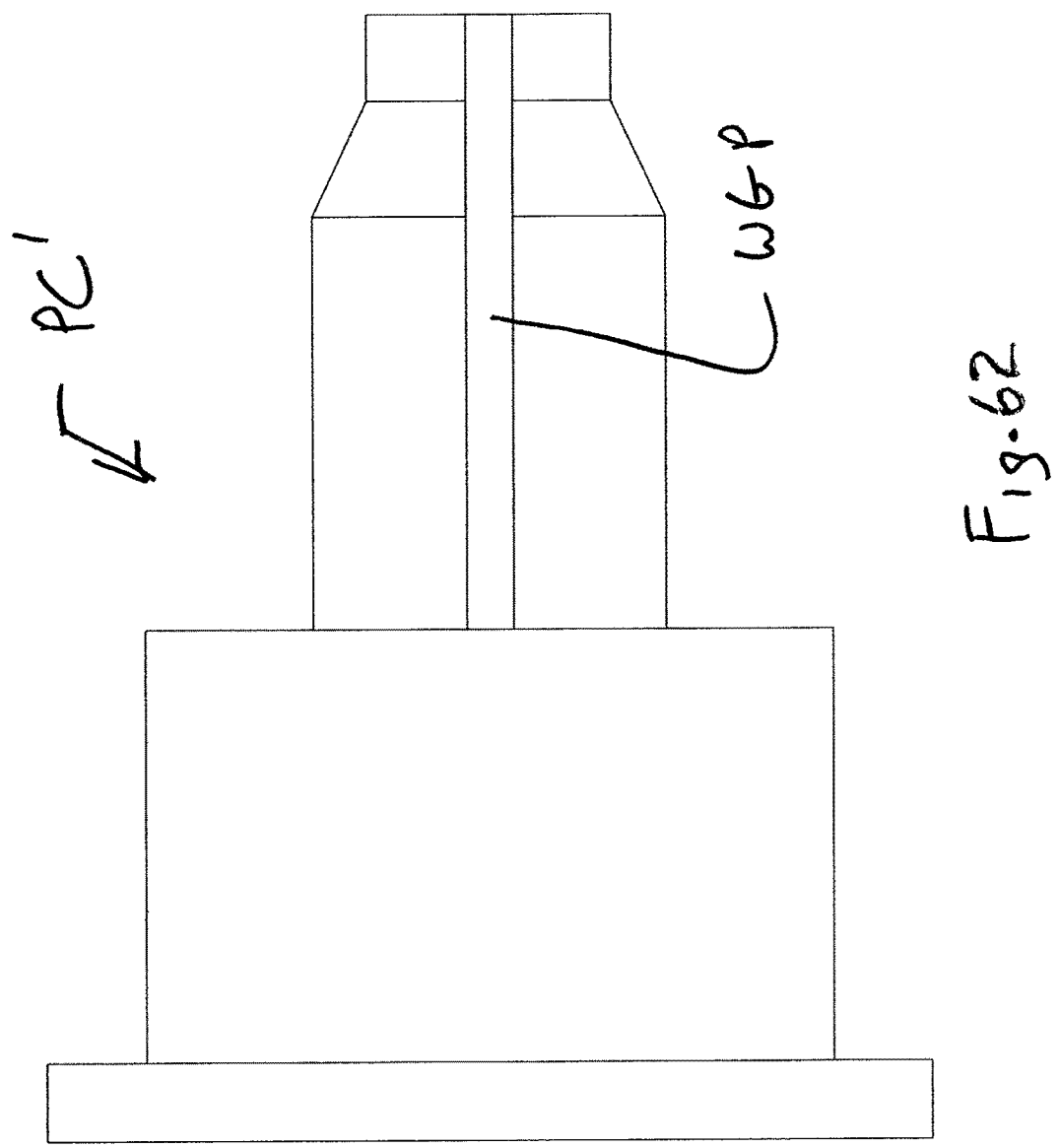
FIGS. 62 and 63 show a non-limiting embodiment of an outer cover in according to the invention.
Figure 63:
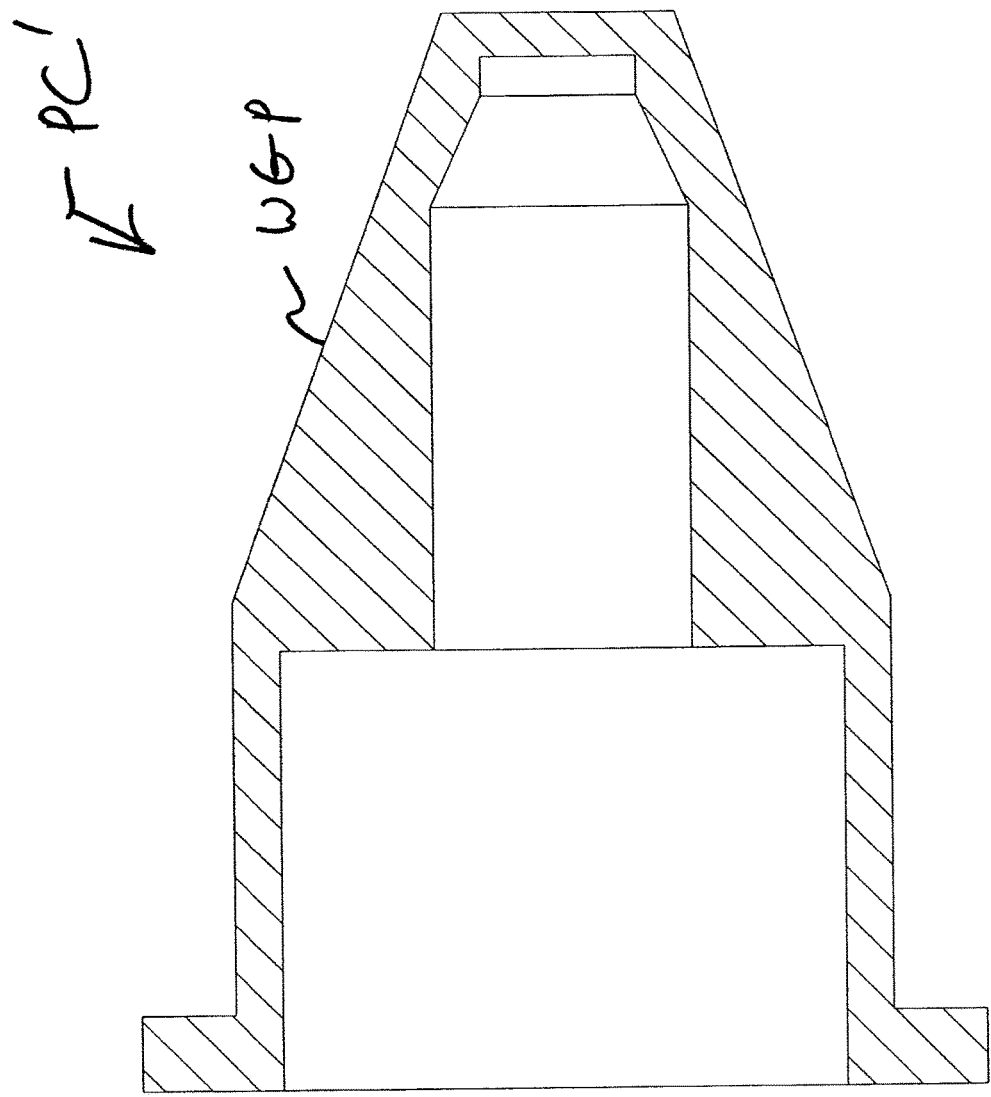

FIGS. 62-63 show an embodiment of an outer cap PC' which can be used with one or more pen needle disclosed herein. The cap PC' utilizes a wing type gripping projection WGP which can allow a user to more easily thread-on the pen needle.

Figure 64:
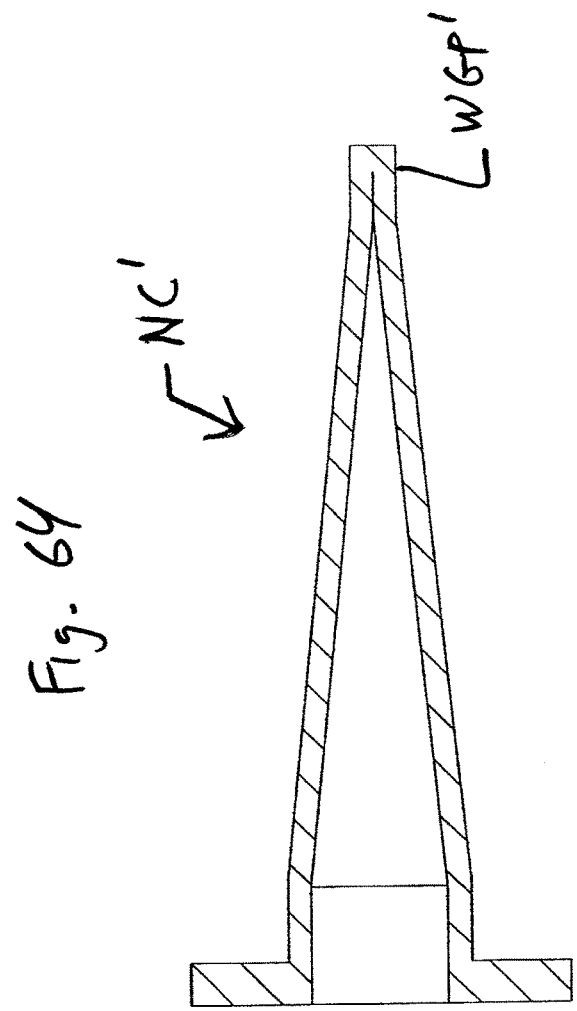
FIGS. 64 and 65 show a non-limiting embodiment of an inner or needle cover in according to the invention.
Figure 65:
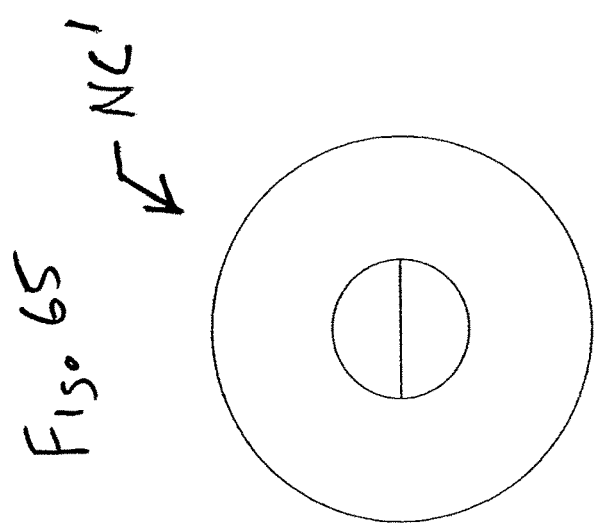

FIGS. 64-65 show an embodiment of a needle cap NC' which can be used with one or more pen needle disclosed herein. The cap NC' utilizes a wing type gripping projection WGP' which can allow a user to more easily remove the cap from the pen needle.

Figure 66:
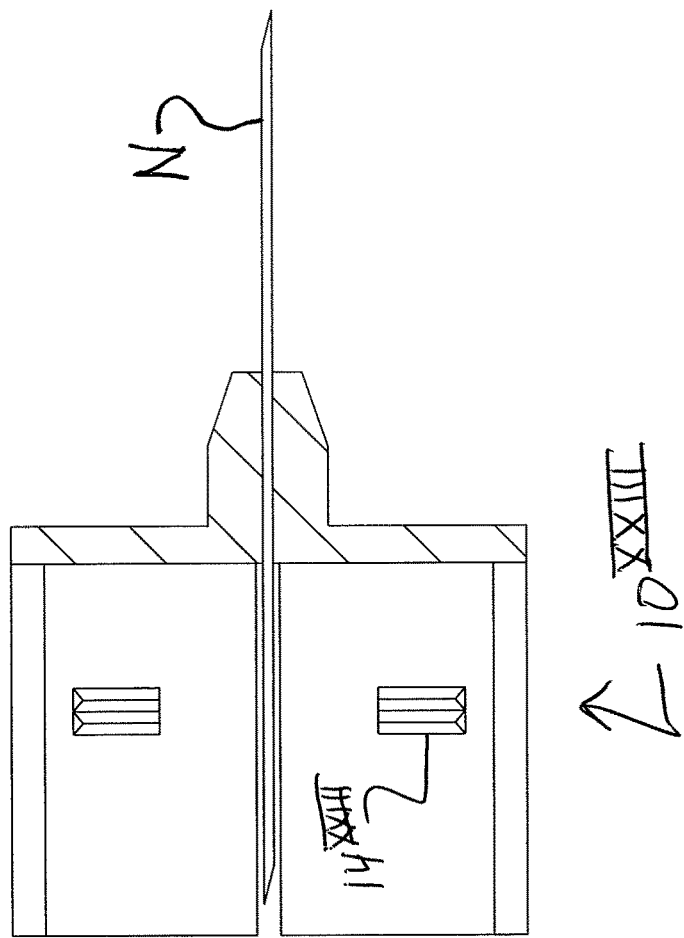
FIGS. 66 and 67 show another non-limiting embodiment of a pen needle or tip assembly in according to the invention.
Figure 67:
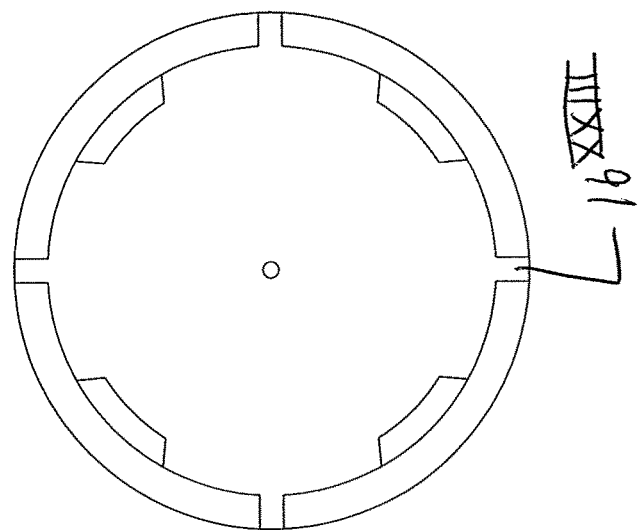

FIGS. 66-67 show another embodiment of a pen needle $10^{XXIII}$. As with previous embodiments, the proximal end of the needle tip $10^{XXIII}$ includes a needle while the distal end is open and includes an interior space or opening which is sized to allow the needle tip $10^{XXIII}$ to be mounted onto the threaded proximal end of the pen needle injection device. The pen needle $10^{XXIII}$ also includes a proximal hub, a wall, which in this embodiment has an enlarged diameter to protect the user from the needle N when gripping the generally cylindrical sidewall. Thread sections $14^{XXIII}$ and sidewall slots $16^{XXIII}$ are also utilized. Each thread section $14^{XXIII}$ is arranged generally offset 45 degree to the sidewall slots $16^{XXIII}$. In embodiments, the slots $16^{XXIII}$ extend all the way from the distal end to the distal end of the wall. The four equally angularly spaced slots $16^{XXIII}$ allow the sidewall to deflect outwardly more evenly than certain previous embodiments when a user axially pulls off pen needle $10^{XXIII}$ without unthreading or rotation. Unlike previous embodiments, a user need not move projections or sections towards each other so as to cause a widening of the slots $16^{XXIII}$. Instead, the pulling off motion causes expansion of the slots $16^{XXIII}$. This embodiment can also otherwise utilize features similar to that shown in FIG. 1 such as features 3, 4 and 5.

FIGS. 68-69 show another embodiment of a pen needle $10^{XXIV}$. As with previous embodiments, the proximal end of the needle tip $10^{XXIV}$ includes a needle while the distal end is open and includes an interior space or opening which is sized to allow the needle tip $10^{XXIV}$ to be mounted onto the threaded proximal end of the pen needle injection device. The pen needle $10^{XXIV}$ also includes a proximal hub, a wall, which in this embodiment has an enlarged diameter to protect the user from the needle N when gripping the generally cylindrical sidewall. Thread sections $14^{XXIV}$ and sidewall slots $16^{XXIV}$ are also utilized. Each thread section $14^{XXIV}$ is longer than the previous embodiments and is arranged generally offset 45 degree to the sidewall slots $16^{XXIV}$. In embodiments, the slots $16^{XXIV}$ extend all the way from the distal end to the distal end of the wall. The four equally angularly spaced slots $16^{XXIV}$ allow the sidewall to deflect outwardly more evenly than certain previous embodiments when a user axially pulls off pen needle $10^{XXIV}$ without unthreading or rotation. Unlike previous embodiments, a user need not move projections or sections towards each other so as to cause a widening of the slots $16^{XXIV}$. Instead, the pulling off motion causes expansion of the slots $16^{XXIV}$. This embodiment can also otherwise utilize features similar to that shown in FIG. 1 such as features 3, 4 and 5.

FIGS. 70 and 71 shows another non-limiting embodiment of the invention. In this embodiment, there is provided an injection device tip $10^{XXV}$ comprising a body configured to be removably connected to an injection device. The body includes at least one semi-cylindrical wall defining an internal space like other embodiments. A needle N has a first portion projecting out from a front wall of the body and a second portion projecting into the internal space. A device 20' is structured and arranged to prevent a user from being pricked by the second portion. The device 20' is at least one of (a) coupled to the body via a living hinge 19', (b) movable from an original position (similar to FIG. 17) to a position covering the second portion, (c) movable parallel to an axis of the needle N, movable between unlocked position (no engagement of locking system LS') and a locked position (engagement of locking system LS'), and an axially movable needle shield 20' that has at least a portion that moved within the internal space.

Figure 72:
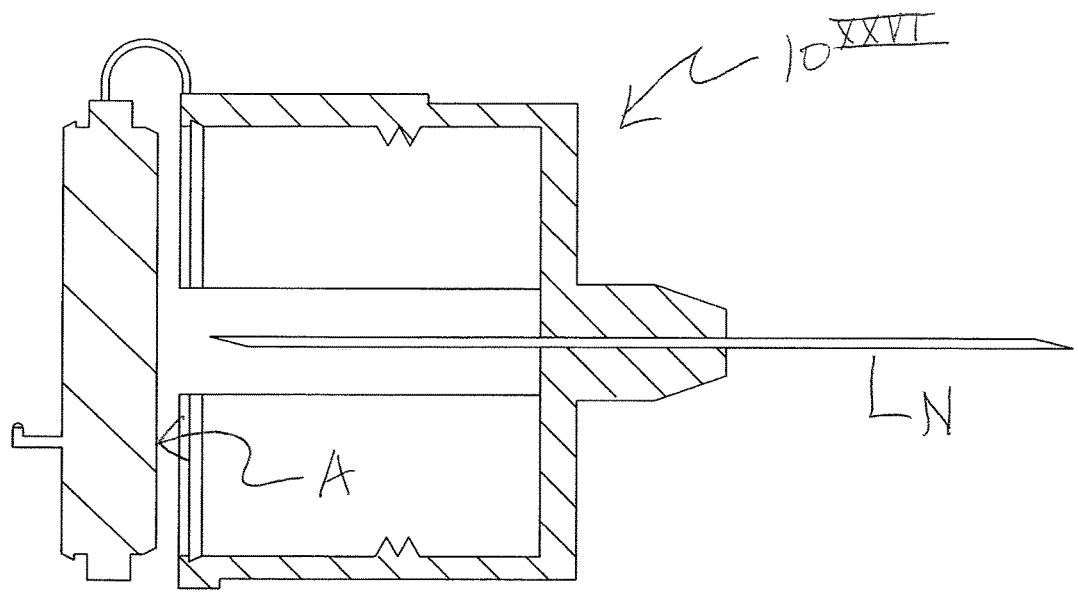
FIGS. 72 and 73 show another non-limiting embodiment of a pen needle or tip assembly in according to the invention.
Figure 73:
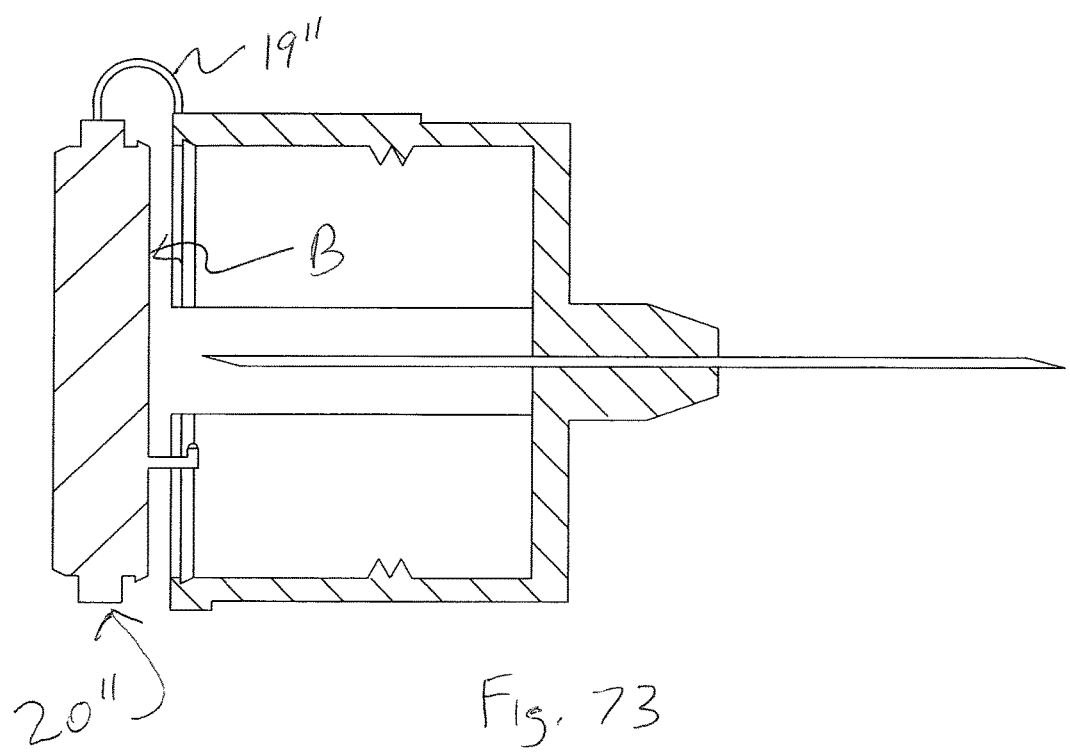

FIGS. 72 and 73 shows another non-limiting embodiment of the invention. In this embodiment, there is provided an injection device tip $10^{XXVI}$ comprising a body configured to be removably connected to an injection device. The body includes at least one semi-cylindrical wall defining an internal space like other embodiments. A needle N has a first portion projecting out from a front wall of the body and a second portion projecting into the internal space. A device 20" is structured and arranged to prevent a user from being pricked by the second portion. The device or back cap 20" is at least one of (a) optionally coupled to the body via a living hinge 19', (b) movable from an original non-lockable position, closed, or position closing off the back end of the body (in FIG. 72 the device 20" is shown in a position prior to closing off the body) to a position wherein it is non-removably locked to the body so as to permanently closing off the back end of body or pen needle and prevent reuse, (c) movable parallel to an axis of the needle N, (d) can be twisted between the positions shown in FIGS. 72 and 73. Side A can utilize indicia indicating that the pen needle is new, unused, unlocked, etc., and side B can utilize indicia indicating that the pen needle is used, old, locked, etc.

The devices described herein can also utilize one or more features disclosed in the following pen needle documents: U.S. Pat. No. 7,871,397 (Publication No. 2008/0154192) to SCHRAGA; U.S. 2010/0292654 to SCHRAGA; and U.S. 2011/0077615 to SCHRAGA. Each of these applications and the documents expressly incorporated therein are hereby expressly incorporated by reference in the instant application. Furthermore, one or more of the various parts of the device can preferably be made as one-piece structures by e.g., injection molding, when doing so reduces costs of manufacture. Non-limiting materials for most of the parts include synthetic resins such as those approved for syringes, blood collection devices, or other medical devices. Furthermore, the invention also contemplates that any or all disclosed features of one embodiment may be used on other disclosed embodiments, to the extent such modifications function for their intended purpose.

It is noted that the foregoing examples have been provided merely for the purpose of explanation and are in no way to be construed as limiting of the present invention. While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed:

1. An injection tip device comprising, in an uninstalled state:
   a body comprising a sidewall having two integrally formed and generally equally spaced sidewall slots extending through the sidewall, the sidewall slots separating two flexible sidewall portions from each other, and two integrally formed projecting sections each spanning across a corresponding one of the sidewall slots and connected between the flexible sidewall portions, an outer surface of the body having a generally oval cross-section and configured to be removably connected to an injection device;
   a needle having a first portion projecting out from the body and a second portion projecting into a space within the body, said second portion having a puncturing end; and
   where the integrally formed projecting sections can be forced together by a user, and where the flexible sidewall portions deflect outwardly to cause release of an engagement between the body and a proximal end of the injection device when the user forces the integrally formed projecting sections together.

2. The injection tip of claim 1, in combination with a main outer cover structured and arranged to receive therein or substantially cover the body and the first portion of the needle.

3. The injection device tip of claim 1, wherein the body comprises at least one internal thread section or partial thread section for engaging an external thread of the proximal end of the injection device.

4. The injection device tip of claim 1, wherein, once installed, the tip is capable of threadably engaging with the proximal end of the injection device.

5. The injection device tip of claim 1, wherein the body comprises at least one partial internal thread section for engaging an external thread of the proximal end of the injection device.

6. The injection device tip of claim 1, wherein the body comprises at least two oppositely arranged partial internal thread sections for engaging an external thread of the proximal end of the injection device.

7. The injection device tip of claim 1, wherein the outer surface of the body is generally oval shaped at least in an area of the body located closer to a rear end of the body than to a front end of the body.

8. The injection device tip of claim 1, further comprising at least one of:
   a safety shield adapted to cover the needle; and
   an enlarged diameter flange or member arranged between free ends of the first and second portions of the needle.

9. The injection device tip of claim 1, further comprising a safety shield movably mounted to the body and being adapted to cover the needle.

10. The injection device tip of claim 1, further comprising a safety shield or needle guard movably mounted to the body.

11. The injection device tip of claim 9, wherein the safety shield is movably mounted to the body by a living hinge coupled to the safety shield and the body.

12. An injection tip device comprising, in an uninstalled state:
    a body consisting essentially of a sidewall having two flexible portions separated by two generally equally spaced sidewall slots extending through the sidewall, two integrally formed projecting sections each spanning across a corresponding one of the sidewall slots and connected between the flexible portions of the sidewall, and a front wall at a front end of the body, where the sidewall slots separating the two flexible portions extend through the sidewall from the front wall to a rear end of the body, an outer surface of the flexible portions and integrally formed projecting sections has a generally oval cross-section, and the body is configured to be removably connected to an injection device;
    a needle having a first portion projecting out from the front wall of the body and a second portion projecting from the front wall into a space within the body, said second portion having a puncturing end; and
    wherein the integrally formed projecting sections can be forced together by a user, and where the flexible portions can be deflected outwardly to cause release of an engagement between the body and a proximal end of the injection device when the user forces the integrally formed projecting sections together.

13. The injection device tip of claim 12, wherein each flexible portion comprises at least one inner projection configured to engage the proximal end of the injection device.

14. The injection device tip of claim 13, wherein each flexible portion comprises a first inner projection and a second inner projection, where the first and second inner projections are configured to engage the proximal end of the injection device.

15. The injection device tip of claim 13, wherein the at least one inner projection is angularly offset from a center of the flexible portions.

16. The injection device tip of claim 13, wherein the at least one inner projection comprises an internal thread section or partial thread section for engaging an external thread of the proximal end of the injection device.

17. The injection device tip of claim 7, wherein the front end of the body is generally circular shaped.

18. The injection device tip of claim 8, wherein the enlarged diameter flange or member extends beyond the flexible sidewall portions of the body.

19. The injection device tip of claim 18, wherein the enlarged diameter flange or member extends beyond the integrally formed projecting sections of the body.

* * * * *